United States Patent
Clarke et al.

(10) Patent No.: US 6,667,342 B1
(45) Date of Patent: Dec. 23, 2003

(54) BENZENESULFONAMIDE-DERIVATIVES AND THEIR USE AS MEDICAMENTS

(75) Inventors: David S Clarke, Macclesfield (GB); Jeremy N Burrows, Macclesfield (GB); Paul Ro Whittamore, Macclesfield (GB); Roger J Butlin, Macclesfield (GB); Thorsten Nowak, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/622,678

(22) PCT Filed: Mar. 11, 1999

(86) PCT No.: PCT/GB99/00739
§ 371 (c)(1),
(2), (4) Date: Aug. 22, 2000

(87) PCT Pub. No.: WO99/47508
PCT Pub. Date: Sep. 23, 1999

(30) Foreign Application Priority Data

Mar. 17, 1998 (GB) .............................................. 9805520

(51) Int. Cl.$^7$ .............................................. A01N 41/06
(52) U.S. Cl. .................... 514/603; 514/604; 514/227.5; 514/231.2; 514/247; 514/256; 514/252.1; 514/269; 514/315; 514/347; 514/396; 514/408; 544/56; 544/159; 544/213; 544/297; 544/326; 544/358; 544/407; 546/244; 546/247; 546/248; 548/342.1; 548/570
(58) Field of Search .............................. 564/85, 86, 89; 544/56, 159, 213, 297, 326, 358, 407; 546/244, 247, 248; 548/342.1, 570; 514/603, 604, 227.5, 231.2, 256, 241, 247, 269, 252.1, 315, 347, 396, 401

(56) References Cited

U.S. PATENT DOCUMENTS

| | | | | |
|---|---|---|---|---|
| 4,537,618 A | * | 8/1985 | Schurter et al. | ............. 544/321 |
| 5,248,693 A | * | 9/1993 | Gerspacher et al. | ........ 548/511 |
| 5,486,515 A | | 1/1996 | Brown et al. | ................ 544/101 |
| 5,510,386 A | * | 4/1996 | Empfield et al. | ............. 546/89 |

FOREIGN PATENT DOCUMENTS

| | | |
|---|---|---|
| CA | 1 228 355 | 10/1987 |
| EP | 0 002 309 | 6/1979 |
| EP | 0 002 892 | 7/1979 |
| EP | 0 040 932 | 12/1981 |
| EP | 0 079 191 | 5/1983 |
| EP | 0 096 002 | 12/1983 |
| EP | 0 100 172 | 2/1984 |
| EP | 0 253 500 | 1/1988 |
| EP | 0 253 503 | 1/1988 |
| EP | 0 524 781 | 1/1993 |
| EP | 0 617 010 | 9/1994 |
| EP | 0 625 511 | 11/1994 |
| EP | 0 625 516 | * 11/1994 |
| GB | 2 278 054 | 11/1994 |
| WO | WO 93/10094 | 5/1993 |
| WO | WO 93/23358 | 5/1993 |
| WO | WO 94/26739 | 11/1994 |
| WO | WO 96/28151 | 9/1996 |
| WO | WO 97/38124 | 10/1997 |
| WO | WO 97/38235 | 10/1997 |
| WO | WO 99/44618 | 9/1999 |
| WO | WO 99/62506 | 12/1999 |
| WO | WO 99/62873 | 12/1999 |

OTHER PUBLICATIONS

Jackman et al. J. Pharm. Pharmacol. 12, 648–655, 1960.*
Bayles et al., "A Smiles Rearrangement Involving Non–Activated Aromatic Systems; the Facile Conversion of Phenols to Anilines", Synthesis, 1977, vol. 1. pp. 33–34.
Bayles et al.,, "The Smiles Rearrangement of 2–Aryloxy–2–methylpropanamides. Synthesis of N–Aryl–2–hydroxy–2–methyl–propanamides", Synthesis, 1977, vol. 1, pp, 31–33.
Furr et al., "A Novel Non–Steroidal, Peripherally Selective Antiandrogen", J. Endrocrinol., 1987, vol. 113 (3), R7–R9.
Glen et al., Structure–Activity Relationships among Non–steriodal Antiandrogens, Third SCI–RSC Medicinal Chemistry Symposium, 1986, vol. 55, pp. 345–361.
Grant et al., "Anilide Tertiary Carbinols: A New Structural Class Of Potent Potassium Channel Openers", Bioorg. Med. Chem. Lett., 1993, vol. 3 (12), pp. 2723–2724.
Howe et al., "ZENECA ZD6169: A Novel $K_{ATP}$ Channel Opener with In Vivo Selectivity for Urinary Bladder", J. Pharmacol. Exp. Ther. 1995, vol. 274 (2), pp, 884–890.
Jackman et al., "Studies In The Field of Diuretics", J. Pharm. And Pharmacol., 1960, vol. 12, pp. 648–655.
Li et al., "Zeneca ZD6169 and Its Analogs from a Novel Series of Anilide Tertiary Carbinols: in vitro $K_{ATP}$ Channel Opening Activity in Bladder Detrusor", Pharmacology, 1995, vol. 51, pp. 33–42.
Morris et al., "Hydrogen Bonding Parameters In The S.A.R. of Non–Steroidal Anti–Androgens", Phamacol. Libr., 1987, vol. 10, pp. 204–206.
Morris et al., "Non–Steroidal Antiandrogens. Design of Novel Compounds Based on an Infrared Study of the Dominant Conformationand Hydrogen–Bonding Properties of a Series of Anilide Antiandrogens", J. Med. Chem. 1991, vol. 34, pp, 447–455.

(List continued on next page.)

Primary Examiner—Richard L. Raymond
Assistant Examiner—Venkataraman Balasubramanian
(74) Attorney, Agent, or Firm—Morgan Lewis & Bockius LLP

(57) ABSTRACT

Compounds of formula (I), pharmaceutically acceptable salts or in vivo hydrolysable esters thereof, wherein: Ring X is phenyl or a six membered heteroaryl ring containing one or two ring nitrogens where said nitrogens are optionally oxidised to form the N-oxide; $R^1$ and $R^2$ are substituents as defined within; $R^3$ and $R^4$ are defined within and are alkyl or halo alkyl or together form a halocycloalkyl ring; $R^5$ is a substituent as defined within; Y—Z is a linking group as defined within; are useful in the production of a elevation of PDH activity in a warm-blooded animal such as a human being. Pharmaceutical compositions, methods and processes for preparation of compounds of formula (I) are described.

11 Claims, No Drawings

OTHER PUBLICATIONS

Ohnmacht et al., "N–Aryl–3,3,3–trifluoro–2–hydroxy–2–methylpropanamides: $K_{ATP}$ Potassium Channel Openers. Modifications on the Western Region", J. Med. Chem., 1996, vol. 39 (23), pp. 4592–4601.

Ohnmacht et al., "N–Aryl–3,3,3–trifluoro–2–hydroxy–2–methylpropanamides: $K_{ATP}$ Potassium Channel Openers. Modifications on the Western Region", J. Med. Chem., 1996, Additions and Corrections, vol. 40 (6), p. 1048.

Russell, "Crystal Receptor Models In Medicinal Chemistry: Application To The Generation of Highly Potent Channel Openers", Bioorg. Med. Chem. Lett. 1996, vol. 6(7), pp. 913–918.

Tenthorey et al.; "New Antiarrhythmic Agents. 3. Primary β–Amino Anilides", J. Med. Chem. 1979, vol. 22 (10), pp. 1182–1186.

Trivedi et al., "K–Channel Opening Activity of ZD6169 and Its Analogs: Effect on $^{86}$Rb Efflux and $^{3}$H–1075 Binding in Bladder Smooth Muscle", Pharmacology, 1995, vol. 50 (6), pp. 388–397.

Tucker et al., "Nonsteroidal Antiandrogens. Synthesis and Structure–Activity Relationships of 3–Substituted Derivatives of 2–Hydroxypropionanilides", J. Med. Chem., 1988, vol. 31, pp. 954–959.

Tucker et al., "Resolution of the Nonsteriodal Antiandrogen 4'–Cyano–3–[(4–fluorophenyl)sulfonyl]–2–hydroxy–2–methyl–3'–(trifluoromethyl)– propionanilide and the Determination of the Absolute Configuration of the Active Enantiomer", J. Med. Chem. 1988. Vol. 31 (4), pp. 885–887.

Wakeling et al., "Receptor Binding And Biological Actvity Of Steriodal and Nonsteriodal Antiandrogens", J. Steroid. Biochem., 1981, vol. 15, pp. 355–359.

Chemical Abstracts, vol. 55, No. 9, May 1, 1961, Columbus, Ohio, US; abstract No. 8336a, XP002107578 see abstract, col. 8336, lines 8–9 & G.B. Jackman et al: J. Pharm. and Pharmacol., vol. 12, 1960, pp. 648–655.

J.R. Empfield et al: Bioorg. Med. Chem. Lett., vol. 7, No. 7, 1997, pp. 775–778, XP004136128 see table I, compounds e, f.

* cited by examiner

BENZENESULFONAMIDE-DERIVATIVES AND THEIR USE AS MEDICAMENTS

The present invention relates to compounds which elevate pyruvate dehydrogenase (PDH) activity, processes for their preparation, pharmaceutical compositions containing them as active ingredient, methods for the treatment of disease states associated with reduced PDH activity, to their use as medicaments and to their use in the manufacture of medicaments for use in the elevation of PDH activity in warm-blooded animals such as humans.

Within tissues adenosine triphosphate (ATP) provides the energy for synthesis of complex molecules and, in muscle, for contraction. ATP is generated from the breakdown of energy-rich substrates such as glucose or long chain free fatty acids. In oxidative tissues such as muscle the majority of the ATP is generated from acetyl CoA which enters the citric acid cycle, thus the supply of acetyl CoA is a critical determinant of ATP production in oxidative tissues. Acetyl CoA is produced either by β-oxidation of fatty acids or as a result of glucose metabolism by the glycolytic pathway. The key regulatory enzyme in controlling the rate of acetyl CoA formation from glucose is PDH which catalyses the oxidation of pyruvate to acetyl CoA and carbon dioxide with concomitant reduction of nicotinamide adenine dinucleotide (NAD) to NADH.

In disease states such as both non-insulin dependent (NIDDM) and insulin-dependent diabetes mellitus (IDDM), oxidation of lipids is increased with a concomitant reduction in utilisation of glucose, which contributes to the hyperglycaemia. Reduced glucose utilisation in both IDDM and NIDDM is associated with a reduction in PDH activity. In addition, a further consequence of reduced PDH activity may be that an increase in pyruvate concentration results in increased availability of lactate as a substrate for hepatic gluconeogenesis. It is reasonable to expect that increasing the activity of PDH could increase the rate of glucose oxidation and hence overall glucose utilisation, in addition to reducing hepatic glucose output. Another factor contributing to diabetes mellitus is impaired insulin secretion, which has been shown to be associated with reduced PDH activity in pancreatic β-cells (in a rodent genetic model of diabetes mellitus Zhou et al. (1996) Diabetes 45: 580–586).

Oxidation of glucose is capable of yielding more molecules of ATP per mole of oxygen than is oxidation of fatty acids. In conditions where energy demand may exceed energy supply, such as myocardial ischaemia, intermittent claudication, cerebral ischaemia and reperfusion, (Zaidan et al., 1998; J. Neurochem. 70: 233–241), shifting the balance of substrate utilisation in favour of glucose metabolism by elevating PDH activity may be expected to improve the ability to maintain ATP levels and hence function.

An agent which is capable of elevating PDH activity may also be expected to be of benefit in treating conditions where an excess of circulating lactic acid is manifest such as in certain cases of sepsis.

The agent dichloroacetic acid (DCA) which increases the activity of PDH after acute administration in animals, (Vary et al., 1988; Circ. Shock, 24: 3–18), has been shown to have the predicted effects in reducing glycaemia, (Stacpoole et al., 1978; N. Engl. J. Med. 298: 526–530), and as a therapy for myocardial ischaemia (Bersin and Stacpoole 1997; American Heart Journal, 134: 841–855) and lactic acidaemia, (Stacpoole et al., 1983; N. Engl. J. Med. 309: 390–396).

PDH is an intramitochondrial multienzyme complex consisting of multiple copies of several subunits including three enzyme activities E1, E2 and E3, required for the completion of the conversion of pyruvate to acetyl CoA (Patel and Roche 1990; FASEB J., 4: 3224–3233). E1 catalyses the non-reversible removal of $CO_2$ from pyruvate; E2 forms acetyl CoA and E3 reduces NAD to NADH. Two additional enzyme activities are associated with the complex: a specific kinase which is capable of phosphorylating E1 at three serine residues and a loosely-associated specific phosphatase which reverses the phosphorylation. Phosphorylation of a single one of the three serine residues renders the E1 inactive. The proportion of the PDH in its active (dephosphorylated) state is determined by a balance between the activity of the kinase and phosphatase. The activity of the kinase may be regulated in vivo by the relative concentrations of metabolic substrates such as NAD/NADH, CoA/acetylCoA and adenine diphosphate (ADP)/ATP as well as by the availability of pyruvate itself.

European Patent Publication No. 625516 refers to compounds which are capable of relaxing bladder smooth muscle and which may be used in the treatment of urge incontinence. We have found, surprisingly, that compounds also containing a sulphonamide moiety disclosed in the present invention are very good at elevating PDH activity, a property nowhere disclosed in EP 625516.The present invention is based on the surprising discovery that certain compounds elevate PDH activity, a property of value in the treatment of disease states associated with disorders of glucose utilisation such as diabetes mellitus, obesity, (Curto et al., 1997; Int. J. Obes. 21: 1137–1142), and lactic acidaemia. Additionally the compounds may be expected to have utility in diseases where supply of energy-rich substrates to tissues is limiting such as peripheral vascular disease, (including intermittent claudication), cardiac failure and certain cardiac myopathies, muscle weakness, hyperlipidaemias and atherosclerosis (Stacpoole et al., 1978; N. Engl. J. Med. 298: 526–530). A compound that activates PDH may also be useful in treating Alzheimer disease (AD) (J Neural Transm (1998) 105: 855–870).

Accordingly, the present invention provides a compound of formula (I):

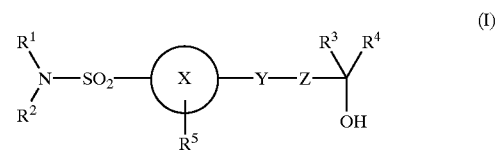

wherein:
  Ring X is phenyl or a six membered heteroaryl ring containing one or two ring nitrogens where said nitrogens are optionally oxidised to form the N-oxide;
  $R^1$ and $R^2$ are independently as defined in (a) or (b);
  $R^3$ and $R^4$ are as defined in (c) or (d);
  $R^5$ is as defined in (e) or (f);
  Y—Z is as defined in (g) or (h)
  wherein:
    (a) either $R^1$ and $R^2$ are each selected independently from hydrogen, $C_{1-3}$alkyl, pyridyl and phenyl which is unsubstituted or substituted by one or two substituents selected independently from $C_{1-4}$alkyl, $C_{1-4}$alkoxy, $C_{2-4}$alkenyloxy, hydroxy, halo and cyano,
      or $R^1$ and $R^2$ together with the nitrogen atom to which they are attached form morpholino, thiomorpholino, piperidinyl, pyrrolidinyl or imidazolyl;

(b) either $R^1$ and $R^2$ are each selected independently from phenyl substituted by one or more P (wherein P is as defined hereinbelow), phenyl substituted by one or more groups selected from $C_{1-4}$alkyl, $C_{1-4}$alkoxy, $C_{2-4}$alkenyloxy, hydroxy, halo and cyano and additionally substituted by one or more groups selected from P, a heterocyclic group other than unsubstituted pyridyl which is optionally substituted on a ring carbon by one or more Q (wherein Q is as defined hereinbelow) and wherein if said heterocyclic group contains an —NH— moiety that nitrogen may be optionally substituted by a group selected from D (wherein D is as defined hereinbelow), naphthyl optionally substituted by one or more Q, $C_{4-6}$alkyl, $C_{3-6}$cycloalkyl optionally substituted with one or more Q, $C_{2-6}$alkenyl, $C_{2-6}$alkynyl, $C_{1-6}$alkyl substituted by one or more V (wherein V is as defined hereinbelow), $R^6$T- (wherein $R^6$ and T are as defined hereinbelow) and $R^7C_{1-6}$alkylT- (where $R^7$ is as defined hereinbelow), or $R^1$ and $R^2$ together with the nitrogen atom to which they are attached form a heterocyclic group other than unsubstituted morpholino, unsubstituted thiomorpholino, unsubstituted piperidinyl, unsubstituted pyrrolidinyl or unsubstituted imidazolyl which is optionally substituted on a ring carbon by one or more Q (wherein Q is as defined hereinbelow) and wherein if said heterocyclic group contains an —NH— moiety that nitrogen may be optionally substituted by a group selected from D (wherein D is as defined hereinbelow);

(c) either $R^3$ and $R^4$ are independently $C_k$alkyl optionally substituted by from 1 to 2k+1 atoms selected from fluoro and chloro wherein k is 1–3, provided that $R^3$ and $R^4$ are not both methyl;
or $R^3$ and $R^4$ together with the carbon atom to which they are attached, form a $C_m$cycloalkyl ring optionally substituted by from 1 to 2m-2 fluorine atoms wherein m is 3–5;

(d) $R^3$ and $R^4$ are both methyl;

(e) $R^5$ is hydrogen, $C_{1-4}$alkyl, halo$C_{1-4}$alkyl, $C_{1-4}$alkoxy, halo$C_{1-4}$alkoxy, cyano, nitro, $C_{2-4}$alkenyloxy or trifluoromethylthio;

(f) $R^5$ is halo, hydroxy, amino, $C_{1-6}$alkylamino, $(C_{1-6}$alkyl$)_2$amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl(N—$C_{1-6}$alkyl)amino, thiol, $C_{1-6}$alkylsulphanyl, $C_{1-6}$alkylsulphinyl, $C_{1-6}$alkylsulphonyl, sulphanoyl, N-($C_{1-6}$alkyl)aminosulphonyl, N-($C_{1-6}$alkyl$)_2$aminosulphonyl, carboxy, carbamoyl, N-($C_{1-6}$alkyl)carbamoyl, N-($C_{1-6}$alkyl$)_2$carbamoyl, $C_{1-6}$alkoxycarbonyl, formyl, $C_{1-6}$alkanoyl, $C_{2-6}$alkenyl, $C_{2-6}$alkynyl, $C_{5-6}$alkyl, halo$C_{5-6}$alkyl, $C_{5-6}$alkoxy, halo$C_{5-6}$alkoxy or $C_{5-6}$alkenyloxy;

(g) Y—Z is —NHC(O)—, —OCH$_2$—, —SCH$_2$—, —NHCH$_2$—, trans-vinylene, and ethynylene;

(h) Y—Z is —NHC(S)—;

$R^1$ is selected from $C_{1-6}$alkyl (optionally substituted with one or more $R^8$), $C_{3-6}$cycloalkyl optionally substituted with one or more $R^8$, a heterocyclic group optionally substituted on a ring carbon by one or more $R^8$ and if said heterocyclic group contains an —NH— moiety that nitrogen may be optionally substituted by a group selected from D (wherein D is as defined hereinbelow), phenyl optionally substituted by one or more $R^8$, naphthyl optionally substituted by one or more $R^8$;

$R^7$ is a heterocyclic group optionally substituted on a ring carbon by one or more $R^8$ and if said heterocyclic group contains an —NH— moiety that nitrogen may be optionally substituted by a group selected from D (wherein D is as defined hereinbelow), phenyl optionally substituted by one or more $R^8$, naphthyl optionally substituted by one or more $R^8$;

$R^8$ is trifluoromethyl, $C_{1-6}$alkyl, halo, hydroxy, trifluoromethoxy, cyano, $C_{1-6}$alkoxy, formyl, $C_{1-6}$alkanoyl, $C_{1-6}$alkanoyloxy, amino, $C_{1-6}$alkylamino, ($C_{1-6}$alkyl$)_2$amino, $C_{1-6}$alkanoylamino, $C_{1-6}$alkanoyl(N—$C_{1-6}$alkyl)amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, sulphanoyl, N-($C_{1-6}$alkyl)aminosulphonyl, N-($C_{1-6}$alkyl aminosulphonyl carbamoyl$C_{1-6}$alkyl, N-($C_{1-6}$alkyl)carbamoyl$C_{1-6}$alkyl, N-($C_{1-6}$alalkyl, hydroxy-$C_{1-6}$alkyl, hydroxy$C_{1-6}$alkyl, $C_{1-6}$alkoxy$C_{1-6}$alkyl, phenyl$C_{1-6}$alkyl or phenyl$C_{1-6}$alkoxy;

P is selected from —$C_{2-6}$alkyl-M— substituted with one or more $R^9$, —$C_{2-6}$alkenyl-M— optionally substituted with one or more $R^9$, —$C_{2-6}$alkynyl-M— optionally substituted with one or more $R^9$ (with the proviso that in the three previous groups $R^9$ is not a substituent on the carbon atom attached to M), $R^{10}$—CH$_2$—M—, $R^{11}$—M—, thiol, $C_{1-6}$alkylsulphanyl, $C_{1-6}$alkylsulphinyl, $C_{1-6}$alkylsulphonyl, sulphamoyl, nitro, carboxy, $C_{1-6}$alkoxycarbonyl, amino, $C_{1-6}$alkylamino, ($C_{1-6}$alkyl$)_2$amino, carbamoyl, N-($C_{1-6}$alkyl)carbamoyl, N-($C_{1-6}$alkyl$)_2$carbamoyl, $C_{1-6}$alkanoylamino, $C_{1-6}$alkanoyl(N—$C_{1-6}$alkyl)amino, trifluoromethyl, trifluoromethoxy, formyl, $C_{1-6}$alkanoyl, $C_{5-6}$alkyl, $C_{2-6}$alkenyl, $C_{2-6}$alkynyl, N-($C_{1-6}$alkyl)aminosulphonyl, hydroxymethyl, hydroxyacetyl, N-($C_{1-6}$alkyl$)_2$aminosulphonyl, $C_{1-6}$alkanoylaminosulphonyl, $C_{1-6}$alkanoyl(N—$C_{1-6}$alkyl)aminosulphonyl, $C_{1-6}$alkylsulpbonylaminocarbonyl, $C_{1-6}$alkylsulphonyl (N—$C_{1-6}$alkyl)aminocarbonyl, $C_{5-6}$alkoxy, $C_{5-6}$alkenyloxy, phenyl optionally substituted by one or more $R^8$, naphthyl optionally substituted by one or more $R^8$ and a heterocyclic group optionally substituted on a ring carbon by one or more $R^8$ and if said heterocyclic group contains an —NH— moiety that nitrogen may be optionally substituted by a group selected from D (wherein D is as defined hereinbelow);

Q is selected from any of the values defined for P, $C_{1-4}$alkyl, $C_{1-4}$alkoxy, $C_{2-4}$alkenyloxy, hydroxy, halo and cyano;

V is selected from any of the values defined for Q, phenyl optionally substituted by one or more Q, naphthyl optionally substituted by one or more Q, a heterocyclic group optionally substituted on a ring carbon by one or more Q and if said heterocyclic group contains an —NH— moiety that nitrogen may be optionally substituted by a group selected from D (wherein D is as defined hereinbelow) or $C_{3-6}$cycloalkyl optionally substituted with one or more Q;

T is selected from —O—, —C(O)—, —NH—, —N(N—$C_{1-6}$alkyl)—, —C(O)NH—, —NHC(O)—, —C(O)N (N—$C_{1-6}$alkyl)—, —N(N—$C_{1-6}$alkyl)C(O)—, —SO$_2$—, —C(S)—, —C(S)NH—, —NHC(S)—, —C(S)N(N—$C_{1-6}$alkyl)— and —N(N—$C_{1-6}$alkyl)C(S)—;

M is selected from —O—, —N($R^{12}$)—, —C(O)—, —N($R^{12}$)C(O)—, —C(O)N($R^{12}$)—, —S(O)$_n$—, —OC (O)—, —C(O)O—, —N(R$^{12}$)C(O)O—, —OC(O)N(R$^{12}$)—, —C(S)N(R$^{12}$)—, —N(R$^{12}$)C(S)—, —SO$_2$N(R$^{12}$)—, —N(R$^{12}$)SO$_2$— and —N(R$^{12}$)C(O)N(R$^{12}$)—, —N(R$^{12}$)C(S)N(R$^{12}$)—, —SO$_2$NHC(O)—, —SO$_2$N(R$^{12}$)C(O)—, —C(O)NHSO$_2$—, —C(O)N(R$^{12}$)SO$_2$— or M is a direct bond;

D is selected from C$_{1-6}$alkyl, C$_{1-6}$alkanoyl, C$_{1-6}$alkylsulphonyl, C$_{1-6}$alkoxycarbonyl, carbamoyl, N-(C$_{1-6}$alkyl)carbamoyl, N,N-(C$_{1-6}$alkyl)$_2$carbamoyl, benzoyl, (heterocyclic group)carbonyl, phenylsulphonyl, (heterocyclic group)sulphonyl, phenyl or a carbon linked heterocyclic group, and wherein any C$_{1-6}$alkyl group may be optionally substituted by one or more R$^9$, and wherein any phenyl or heterocyclic group may be optionally substituted on a ring carbon by one or more groups selected from R$^8$ and if a heterocyclic group contains an —NH— moiety that nitrogen may be optionally substituted by a group selected from E;

E is selected from C$_{1-6}$alkyl, C$_{1-6}$alkanoyl, C$_{1-6}$alkylsulphonyl, C$_{1-6}$alkoxycarbonyl, carbamoyl, N-(C$_{1-6}$alkyl)carbamoyl, N,N-(C$_{1-6}$alkyl)$_2$carbamoyl, C$_{1-6}$alkoxyC$_{1-6}$alkanoyl, phenylC$_{1-6}$alkyl, benzoyl, phenylC$_{1-6}$alkanoyl, phenylC$_{1-6}$alkoxycarbonyl and phenylsulphonyl.

R$^9$ is selected from hydroxy, amino, C$_{1-6}$alkylamino, (C$_{1-6}$alkyl)$_2$amino, carboxy, C$_{1-6}$alkoxy, carbamoyl, N-(C$_{1-6}$alkyl)carbamoyl, N-(C$_{1-6}$alkyl)$_2$carbamoyl, formyl, sulphamoyl, N—C$_{1-6}$alkylaminosulphonyl, N-(C$_{1-6}$alkyl)$_2$aminosulphonyl, C$_{1-6}$alkylsulphonylamino, C$_{1-6}$alkanoylamino, a heterocyclic group optionally substituted on a ring carbon by one or more R$^8$ and if said heterocyclic group contains an —NH— moiety that nitrogen may be optionally substituted by a group selected from D (wherein D is as defined hereinabove), phenyl optionally substituted by one or more R$^8$, naphthyl optionally substituted by one or more R$^8$, C$_{1-6}$alkylsulphanyl, C$_{1-6}$alkylsulphinyl and C$_{1-6}$alkylsulphonyl;

R$^{10}$ is carboxy, carbamoyl, N-(C$_{1-6}$alkyl)carbamoyl, N-(C$_{1-6}$alkyl)$_2$carbamoyl, sulphamoyl, N-(C$_{1-6}$alkyl)aminosulphonyl, N-(C$_{1-6}$alkyl)$_2$aminosulphonyl, C$_{1-6}$alkylsulphanyl, C$_{1-6}$alkylsulphinyl, C$_{1-6}$alkylsulphonyl, C$_{1-6}$alkoxycarbonyl, C$_{1-6}$alkanoylamino, a heterocyclic group optionally substituted on a ring carbon by one or more R$^8$ and if said heterocyclic group contains an —NH— moiety that nitrogen may be optionally substituted by a group selected from D (wherein D is as defined hereinabove), phenyl optionally substituted by one or more R$^8$ or naphthyl optionally substituted by one or more R$^8$;

R$^{11}$ is a heterocyclic group optionally substituted on a ring carbon by one or more R$^8$ and if said heterocyclic group contains an —NH— moiety that nitrogen may be optionally substituted by a group selected from D (wherein D is as defined hereinabove), phenyl optionally substituted by one or more R$^8$, C$_{3-6}$cycloalkyl optionally substituted by one or more R$^8$, or naphthyl optionally substituted by one or more R$^8$;

R$^{12}$ is hydrogen or C$_{1-6}$alkyl optionally substituted with R$^{13}$ with the proviso that R$^{13}$ is not a substituent on the carbon attached to the nitrogen atom of M;

R$^{13}$ is halo, hydroxy, amino, cyano, nitro, trifluoromethyl, trifluoromethoxy, C$_{1-6}$alkyl, C$_{2-6}$alkenyl, C$_{2-6}$alkynyl, C$_{1-6}$alkylamino, (C$_{1-6}$alkyl)$_2$amino, C$_{1-6}$alkanoylamino, C$_{1-6}$alkanoyl(N—C$_{1-6}$alkyl)amino, C$_{1-6}$alkylsulphonylamino, C$_{1-6}$alkylsulphonyl(N—C$_{1-6}$alkyl)amino, thiol, C$_{1-6}$alkylsulphanyl, C$_{1-6}$alkylsulphinyl, C$_{1-6}$alkylsulphonyl, sulphamoyl, N-(C$_{1-6}$alkyl)aminosulphonyl, N-(C$_{1-6}$alkyl)$_2$aminosulphonyl, carboxy, carbamoyl, N-(C$_{1-6}$alkyl)carbamoyl, N-(C$_{1-6}$alkyl)$_2$carbamoyl, C$_{1-6}$alkoxycarbonyl, C$_{1-6}$alkanoyl or formyl;

n is 0–2;

with the proviso that where R$^1$ and R$^2$ are both as defined in (a), R$^3$ and R$^4$ are both as defined in (c), R$^5$ is as defined in (e) and Ring X is phenyl, Y—Z must be —NHC(S)—;

and pharmaceutically acceptable salts or in vivo hydrolysable esters thereof, and with the proviso that when R$^3$ and R$^4$ are both methyl, R$^5$ is hydrogen, fluoro or chloro, Y—Z is ethynylene, X is phenyl and one of R$^1$ and R$^2$ is hydrogen and the other is pyrimidyl-NH—C(O)— or triazinyl-NH—C(O)— (wherein said triazine or pyrimidine is substituted by methyl, methoxy or dimethylamino) then the —SO$_2$NR$^1$R$^2$ moiety cannot be ortho to Y—Z; and provided said compound is not:

4-(3-hydroxy-3-methyl-1-butynyl)-N-(3-methyl-2-pyridinyl)-benzenesulphonamide,

N-{4-[N,N-bis-(sec-butyl)aminosulphonyl]phenyl}-2-hydroxy-2-methyl-3,3,3-trifluoropropanamide, or N-{4-[N,N-bis-(iso-butyl)aminosulphonyl]phenyl}-2-hydroxy-2-methyl-3,3,3-trifluoropropanamide.

In this specification the term "alkyl" includes both straight and branched chain alkyl groups but references to individual alkyl groups such as "propyl" are specific for the straight chain version only. For example, "C$_{1-4}$alkyl" includes propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "haloC$_{1-4}$alkyl" includes 1-chloroethyl and 2-fluoroethyl. The term "halo" refers to fluoro, chloro, bromo and iodo. Where a phrase such as "any C$_{1-6}$alkyl group may be optionally substituted by one or more groups" for the avoidance of doubt, it is to be understood that this refers to all groups that contains a C$_{1-6}$alkyl group, for example this phrase would also relate to a C$_{1-6}$alkanoyl group if that was listed in the paragraph.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —CH$_2$— group can optionally be replaced by a —C(O)—, a ring nitrogen atom may optionally bear a C$_{1-6}$alkyl group and form a quaternary compound or a ring nitrogen and/or sulphur atom may be optionally oxidised to form the N-oxide and or the S-oxides. Examples and suitable values of the term "heterocyclic group" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide.

A "six membered heteroaryl ring containing one or two ring nitrogens where said nitrogens are optionally oxidised to form the N-oxide" is an unsaturated monocyclic ring containing six atoms. Examples are pyridine, pyrimidine, pyrazine and pyridine-N-oxide.

Suitable values when $R^1$ and $R^2$ together with the nitrogen atom to which they are attached form a heterocyclic group are morpholino, piperidyl, piperazinyl, indolinyl, thiazolidinyl, pyrrolidinyl, thiomorpholino, pyrrolinyl, homopiperazinyl, pyrrolyl, imidazolyl, pyrazolyl, pyrazolinyl, pyrazolidinyl, triazolyl, indolyl, isoindolyl and benzimidazolyl. Especially morpholino, piperidyl, piperazinyl, indolinyl, thiazolidinyl, pyrrolidinyl, thiomorpholino, pyrrolinyl and homopiperazinyl.

An example of "$C_{1-6}$alkanoyloxy" is acetoxy. Examples of "$C_{1-6}$alkoxycarbonyl" include methoxycarbonyl, ethoxycarbonyl, n- and t-butoxycarbonyl. Examples of "$C_{1-6}$alkoxy" include methoxy, ethoxy and propoxy. Examples of "$C_{1-6}$alkanoylamino" include formamido, acetamido and propionylamino. Examples of "$C_{1-4}$alkylsulphanyl" include methylthio and ethylthio. Examples of "$C_{1-4}$alkylsulphinyl" include methylsulphinyl and ethylsulphinyl. Examples of "$C_{1-4}$alkylsulphonyl" include mesyl and ethylsulphonyl. Examples of "$C_{1-6}$ alkanoyl" include propionyl and acetyl. Examples of "$C_{1-6}$ alkylamino" include methylamino and ethylamino. Examples of "$(C_{1-6}alkyl)_2amino$" include di-N-methylamino, di-(N-ethyl)amino and N-ethyl-N-methylamino. Examples of "$C_{1-6}alkoxyC_{1-6}alkyl$" methoxymethyl and propoxyethyl. Examples of "carbanoyl$C_{1-6}$ alkyl" are carbamoylmethyl and 2-carbanoylethyl. Examples of "N-($C_{1-6}$alkyl)carbamoyl$C_{1-6}$alkyl" are N-(methyl)aminocarbonylethyl and N-(ethyl)aminocarbonylpropyl. Examples of "N-($C_{1-6}$alkyl)$_2$carbamoyl$C_{1-6}$alkyl" are N,N-(dimethyl)aminocarbonylethyl and N-(methyl)N-(ethyl)aminocarbonylpropyl. Examples of "$C_{2-4}$alkenyloxy" are vinyloxy and allyloxy. Examples of "$C_{3-6}$cycloalkyl" are cyclopropyl and cyclohexyl. Examples of "$C_{2-6}$alkenyl" are vinyl, allyl and 1-propenyl. Examples of "$C_{2-6}$alkynyl" are ethynyl, 1-propynyl and 2-propynyl. Examples of "halo$C_{1-4}$ alkoxy" are 2-fluoroethoxy and 1-bromopropoxy. Examples of "$C_{1-6}$alkanoyl(N—$C_{1-6}$alkyl)amino" are (N-methyl)formamido and (N-propyl)acetamido. Examples of "$C_{1-6}$ alkylsulphonylamino and ethylsulphonylamino. Examples of "$C_{1-6}$alkylsulphonyl(N—$C_{1-6}$alkyl)amino" are methylsulphonyl-(N-ethyl)-amino and ethylsulphonyl-(N-butyl)-amino. Examples of "N-($C_{1-6}$ alkyl)aminosulphonyl" are N-(methyl)aminosulphonyl and N-(ethyl)aminosulphonyl. Examples of "N-($C_{1-6}$alkyl)$_2$ aminosulphonyl" are N,N-(dimethyl)aminosulphonyl and N-(methyl)-N-(ethyl)aminosulphonyl. Examples of "N-($C_{1-6}$alkyl)carbamoyl" are methylaminocarbonyl and ethylaminocarbonyl. Examples of "N—($C_{1-6}$alkyl)$_2$carbamoyl" are dimethylaminocarbonyl and methylethylaminocarbonyl. Examples of "phenyl$C_{1-6}$alkyl" are benzyl and phenethyl. Examples of "phenyl$C_{1-6}$alkoxy" are benzyloxy and phenylethoxy. Examples of "$C_{1-6}$ alkanoylaminosulphonyl" are acetylaminosulphonyl and propionylaminosulphonyl. Examples of "$C_{1-6}$alkanoyl(N—$C_{1-6}$alkyl)aminosulphonyl" are acetyl(N-methyl)aminosulphonyl and propionyl(N-ethyl)aminosulphonyl. Examples of "$C_{1-6}$ alkylsulphonylaminocarbonyl" are mesylaminocarbonyl and ethanesulphonylaminocarbonyl. Examples of "$C_{1-6}$ alkylsulphonyl(N—$C_{1-6}$alkyl)aminocarbonyl" are N-(methyl)mesylaminocarbonyl and N-(methyl) ethanesulphonylaminocarbonyl. Examples of "$C_{1-6}$ alkoxy$C_{1-6}$alkanoyl" are methyoxyacetyl and ethoxypropionyl. Examples of "phenyl$C_{1-6}$alkanoyl" are phenylacetyl and phenylpropionyl. Examples of "(heterocyclic group) carbonyl" are pyrid-3-ylcarbonyl and pyrimid-2-ylcarbonyl. Examples of "(heterocyclic group)$C_{1-6}$alkanoyl" are pyrid-3-ylacetyl and pyrimid-2-ylpropionyl.

Examples of "phenyl$C_{1-6}$alkoxycarbonyl" are benzyloxycarbonyl and phenethyloxycarbonyl.

Another aspect of the invention provides a compound of formula (I) as depicted above wherein:

Ring X is phenyl or a six membered heteroaryl ring containing one or two ring nitrogens where said nitrogens are optionally oxidised to form the N-oxide;

$R^1$ and $R^2$ are independently as defined in (a) or (b);

$R^3$ and $R^4$ are as defined in (c) or (d);

$R^5$ is as defined in (e) or (f);

Y—Z is as defined in (g) or (h)

wherein:

(a) either $R^1$ and $R^2$ are each selected independently from hydrogen, $C_{1-3}$alkyl, pyridyl and phenyl which is unsubstituted or substituted by one or two substituents selected independently from $C_{1-4}$alkyl, $C_{1-4}$alkoxy, $C_{2-4}$alkenyloxy, hydroxy, halo and cyano, or $R^1$ and $R^2$ together with the nitrogen atom to which they are attached form morpholino, thiomorpholino, piperidinyl, pyrrolidinyl or imidazolyl;

(b) either $R^1$ and $R^2$ are each selected independently from phenyl substituted by one or more P (wherein P is as defined hereinbelow), a heterocyclic group other than unsubstituted pyridyl which is optionally substituted by one or more Q (wherein Q is as defined hereinbelow), naphthyl optionally substituted by one or more Q, $C_{4-6}$alkyl, $C_{3-6}$cycloalkyl, $C_{2-6}$alkenyl, $C_{2-6}$alkynyl, $C_{1-6}$alkyl substituted by one or more V (wherein V is as defined hereinbelow), $R^6$T-(wherein $R^6$ and T are as defined hereinbelow) and $R^7C_{1-6}$alkylT- (where $R^7$ is as defined hereinbelow), or $R^1$ and $R^2$ together with the nitrogen atom to which they are attached form a heterocyclic group other than morpholino, thiomorpholino, piperidinyl, pyrrolidinyl or imidazolyl;

(c) either $R^3$ and $R^4$ are independently $C_k$alkyl optionally substituted by from 1 to 2k+1 atoms selected from fluoro and chloro wherein k is 1–3, provided that $R^3$ and $R^4$ are not both methyl;

or $R^3$ and $R^4$ together with the carbon atom to which they are attached, form a $C_m$ cycloalkyl ring optionally substituted by from 1 to 2m–2 fluorine atoms wherein m is 3–5;

(d) $R^3$ and $R^4$ are both methyl;

(e) $R^5$ is hydrogen, $C_{1-4}$alkyl, halo$C_{1-4}$alkyl, $C_{1-4}$alkoxy, halo$C_{1-4}$alkoxy, cyano, nitro, $C_{2-4}$alkenyloxy or trifluoromethylthio;

(f) $R^5$ is halo, hydroxy, amino, $C_{1-6}$alkylamino, ($C_{1-6}$ alkyl)$_2$amino, $C_{1-6}$alkanoylamino, $C_{1-6}$alkanoyl(N—$C_{1-6}$alkyl)amino, $C_{1-6}$alkylsulphonamido, $C_{1-6}$alkylsulphonyl(N—$C_{1-6}$alkyl)amino thiol, $C_{1-6}$alkylsulphanyl, $C_{1-6}$alkylsulphinyl, $C_{1-6}$alkylsulphonyl, sulphamoyl, N-($C_{1-6}$alkyl) aminosulphonyl, N-($C_{1-6}$alkyl)$_2$aminosulphonyl, carboxy, carbamoyl, N-($C_{1-6}$alkyl)carbamoyl, N-($C_{1-6}$alkyl)$_2$carbamoyl, $C_{1-6}$alkyloxycarbonyl, $C_{1-6}$akanoyl, $C_{2-6}$alkenyl, $C_{2-6}$alkynyl, $C_{5-6}$alkyl, halo$C_{5-6}$alkyl, $C_{5-6}$alkoxy, halo$C_{5-6}$alkoxy or $C_{5-6}$alkenyloxy;

(g) Y—Z is —NHC(O)—, —OCH$_2$—, —SCH$_2$—, —NHCH$_2$—, <u>trans</u>-vinylene, and ethynylene;

(h) Y—Z is —NHC(S)—;

$R^6$ is selected from $C_{1-6}$alkyl, $C_{3-6}$cycloalkyl, a heterocyclic group optionally substituted by one or more $R^8$, phenyl optionally substituted by one or more $R^8$, naphthyl optionally substituted by one or more $R^8$;

$R^1$ is a heterocyclic group optionally substituted by one or more $R^8$, phenyl optionally substituted by one or more $R^8$, naphthyl optionally substituted by one or more $R^8$;

$R^1$ is trifluoromethyl, $C_{1-6}$alkyl, halo, hydroxy, trifluoromethoxy, cyano, $C_{1-6}$alkoxy, $C_{1-6}$alkanoyl, $C_{1-6}$alkanoyloxy, amino, $C_{1-6}$alkylamino, $(C_{1-6}$alkyl$)_2$amino, $C_{1-6}$alkanoylamino, $C_{1-6}$alkanoyl(N—$C_{1-6}$alkyl)amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, sulphamoyl, N-($C_{1-6}$alkyl)aminosulphonyl, N-($C_{1-6}$alkyl$)_2$aminosulphonyl, carbamoyl$C_{1-6}$alkyl, N-($C_{1-6}$alkyl)carbamoyl$C_{1-6}$alkyl, N-($C_{1-6}$alkyl$)_2$carbamoyl-$C_{1-6}$alkyl, hydroxy$C_{1-6}$alkyl or $C_{1-6}$alkoxy$C_{1-6}$alkyl;

P is selected from $R^9$—$C_{2-6}$alkyl-M—, $R^9$—$C_{2-6}$alkenyl—M—, $R^9$—$C_2$ alkynyl-M—, $R^{10}$—$CH_2$—M—, $R^{11}$—M—, thiol, $C_{1-6}$alkylsulphanyl, $C_{1-6}$alkylsulphinyl, $C_{1-6}$alkylsulphonyl, sulphamoyl, nitro, carboxy, $C_{1-6}$alkoxycarbonyl, amino, $C_{1-6}$alkylamino, $(C_{1-6}$alkyl$)_2$amino, carbamoyl, N-($C_{1-6}$alkyl)carbamoyl, N-($C_{1-6}$alkyl$)_2$carbamoyl, $C_{1-6}$alkanoylamino, $C_{1-6}$alkanoyl(N—$C_{1-6}$alkyl)amino, trifluoromethyl, trifluoromethoxy, $C_{1-6}$alkanoyl, $C_{5-6}$alkyl, $C_{2-6}$alkenyl, $C_{2-6}$alkynyl, N-($C_{1-6}$alkyl)aminosulphonyl, N-($C_{1-6}$alkyl$)_2$aminosulphonyl, $C_{5-6}$alkyl, $C_{5-6}$alkenyloxy, phenyl optionally substituted by one or more $R^8$, naphthyl optionally substituted by one or more $R^8$, and a heterocyclic group optionally substituted by one or more $R^8$;

Q is selected from any of the values defined for P, $C_{1-4}$alkyl, $C_{1-4}$alkoxy, $C_{2-4}$alkenyloxy, hydroxy, halo and cyano;

V is selected from any of the values defined for Q, phenyl optionally substituted by one or more Q, naphthyl optionally substituted by one or more Q or a heterocyclic group optionally substituted by one or more Q;

T is selected from —O—, —C(O)—, —NH—, —N(N—$C_{1-6}$alkyl)—, —C(O)NH—, —C(O)N(N—$C_{1-6}$alkyl)—, —SO$_2$—, —C(S)—, —C(S)NH—, —C(S)N(N—$C_{1-6}$alkyl)—;

M is selected from O, —N($R^{12}$)—, —N($R^{12}$)C(O)—, —C(O)N($R^{12}$)—, —S(O)$_n$—, —OC(O)—, —C(O)O—, —N($R^{12}$)C(O)O—, —OC(O)N($R^{12}$)—, —C(S)N($R^{12}$)—, —N($R^{12}$)C(S)—, —SO$_2$N($R^{12}$)—, —N($R^{12}$)SO$_2$— and —N($R^{12}$)C(O)N($R^{12}$)—, —N($R^{12}$)C(S)N($R^{12}$)—, —SO$_2$NHC(O)—, —C(O)NHSO$_2$— or M is a direct bond;

$R^9$ is selected from hydroxy, amino, $C_{1-6}$alkylamino, $(C_{1-6}$alkyl$)_2$amino, carboxy, $C_{1-6}$alkoxy, carbamoyl, N-($C_{1-6}$alkyl)carbamoyl, N-($C_{1-6}$alkyl$)_2$carbamoyl, sulphamoyl, N—$C_{1-6}$alkylaminosulphonyl, N-($C_{1-6}$alkyl$)_2$aminosulphonyl, a heterocyclic group optionally substituted by one or more $R^8$, phenyl optionally substituted by one or more $R^8$, naphthyl optionally substituted by one or more $R^8$, $C_{1-6}$alkylsulphanyl, $C_{1-6}$alkylsulphinyl and $C_{1-6}$alkylsulphonyl;

$R^{10}$ is carboxy, carbamoyl, N-($C_{1-6}$alkyl)carbamoyl, N-($C_{1-6}$alkyl$)_2$carbamoyl, sulphamoyl, N-($C_{1-6}$alkyl)aminosulphonyl, N-($C_{1-6}$alkyl$)_2$aminosulphonyl, $C_{1-6}$alkylsulphonyl, a heterocyclic group optionally substituted by one or more $R^8$, phenyl optionally substituted by one or more $R^8$ or naphthyl optionally substituted by one or more $R^8$;

$R^{11}$ is a heterocyclic group optionally substituted by one or more $R^8$, phenyl optionally substituted by one or more $R^8$ or naphthyl optionally substituted by one or more $R^8$;

$R^{12}$ is hydrogen or $C_{1-6}$alkyl;

n is 0–2;

with the proviso that where $R^1$ and $R^2$ are both as defined in (a), $R^3$ and $R^4$ are both as defined in (c), $R^5$ is as defined in (e) and Ring X is phenyl, Y—Z must be —NHC(S)—;

and pharmaceutically acceptable salts or in vivo hydrolysable esters thereof, provided said compound is not 4-(3-hydroxy-3-methyl-1-butynyl)-N-(3-methyl-2-pyridinyl)-benzenesulphonamide;

N-{4-[N,N-bis-(sec-butyl)aminosulphonyl]phenyl}-2-hydroxy-2-methyl-3,3,3-trifluoropropanamide, or N-{4-[N,N-bis-(iso-butyl)aminosulphonyl]phenyl}-2-hydroxy-2-methyl-3,3,3-trifluoropropanamide.

A further aspect of the invention provides a compound of formula (I) as depicted above wherein:

Ring X is phenyl or a six membered heteroaryl ring containing one or two ring nitrogens where said nitrogens are optionally oxidised to form the N-oxide;

either $R^1$ and $R^2$ are each selected independently from hydrogen, $C_{1-6}$alkyl, phenyl optionally substituted by one or more P, a heterocyclic group optionally substituted on a ring carbon by one or more P and wherein if said heterocyclic group contains an —NH— moiety that nitrogen may be optionally substituted by a group selected from D, naphthyl optionally substituted by one or more P, $C_{3-6}$cycloalkyl optionally substituted with one or more P, $C_{2-6}$alkenyl, $C_{2-6}$alkynyl, $C_{1-6}$alkyl substituted by one or more V, $R^6$T- and $R^7C_{1-6}$alkylT-, or $R^1$ and $R^2$ together with the nitrogen atom to which they are attached form a heterocyclic group optionally substituted on a ring carbon by one or more P and wherein if said heterocyclic group contains an —NH— moiety that nitrogen may be optionally substituted by a group selected from D;

either $R^3$ and $R^4$ are independently $C_k$alkyl optionally substituted by from 1 to 2k+1 atoms selected from fluoro and chloro wherein k is 1–3, or $R^3$ and $R^4$ together with the carbon atom to which they are attached, form a $C_m$cycloalkyl ring optionally substituted by from 1 to 2m-2 fluorine atoms wherein m is 3–5;

$R^5$ is halo, hydroxy, amino, $C_{1-6}$alkylamino, $(C_{1-6}$alkyl$)_2$amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl(N—$C_{1-6}$alkyl)amino, thiol, $C_{1-6}$alkylsulphanyl, $C_{1-6}$alkylsulphinyl, $C_{1-6}$alkylsulphonyl, sulphamoylsulphonamido, N-($C_{1-6}$alkyl)aminosulphonyl, N-($C_{1-6}$alkyl$)_2$aminosulphonyl, carboxy, carbamoyl, N-($C_{1-6}$alkyl)carbamoyl, N-($C_{1-6}$alkyl$)_2$carbamoyl, $C_{1-6}$alkoxyalkyloxycarbonyl, formyl, $C_{1-6}$alkanoyl, $C_{2-6}$alkenyl, $C_{2-6}$alkynyl, $C_{5-6}$alkyl, halo$C_{5-6}$alkyl, $C_{5-6}$alkoxy, halo$C_{5-6}$alkoxy or $C_{5-6}$alkenyloxy;

Y—Z is —NHC(O)—, —NHC(S)—, —OCH$_2$—, —SCH$_2$—, —NHCH$_2$—, trans-vinylene, and ethynylene;

$R^6$ is selected from $C_{1-6}$alkyl (optionally substituted with one or more $R^8$), $C_{3-6}$cycloalkyl optionally substituted with one or more $R^8$, a heterocyclic group optionally substituted on a ring carbon by one or more $R^8$ and if said heterocyclic group contains an —NH— moiety that nitrogen may be optionally substituted by a group selected from D, phenyl optionally substituted by one or more $R^8$, naphthyl optionally substituted by one or more $R^8$;

$R^7$ is a heterocyclic group optionally substituted on a ring carbon by one or more $R^8$ and if said heterocyclic group contains an —NH— moiety that nitrogen may be optionally substituted by a group selected from D, phenyl optionally substituted by one or more $R^8$, naphthyl optionally substituted by one or more $R^8$;

$R^8$ is trifluoromethyl, $C_{1-6}$alkyl, halo, hydroxy, trifluoromethoxy, cyano, $C_{1-6}$alkoxy, formyl, $C_{1-6}$alkanoyl, $C_{1-6}$alkanoyloxy, amino, $C_{1-6}$alkylamino, $(C_{1-6}$alkyl$)_2$amino, $C_{1-6}$alkanoyl amino, $C_{1-6}$alkanoyl(N—$C_{1-6}$alkyl) amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, sulphamoyl, N-($C_{1-6}$alkyl) aminosulphonyl, N-($C_{1-6}$alkyl$)_2$aminosulphonyl, carbamoyl$C_{1-6}$alkyl, N-($C_{1-6}$alkyl)carbamoyl$C_{1-6}$alkyl, N-($C_{1-6}$alkyl$)_2$carbamoyl-C, alkyl, hydroxy$C_{1-6}$alkyl, $C_{1-6}$alkoxy$C_{1-6}$alkyl, phenyl$C_{1-6}$alkyl or phenyl$C_{1-6}$alkoxy;

P is selected from $C_{2-6}$alkyl-M— substituted with one or more $R^9$, $C_{2-6}$alkenyl-M— optionally substituted with one or more $R^9$, $C_{2-6}$alkynyl-M— optionally substituted with one or more $R^9$ (with the proviso that in the three previous groups $R^9$ is not a substituent on the carbon atom attached to M), $R^1$—$CH_2$—M—, $R^{11}$—M—, thiol, $C_{1-6}$alkylsulphanyl, $C_{1-6}$alkylsulphinyl, $C_{1-6}$alkylsulphonyl, sulphamoyl, nitro, carboxy, hydroxy, halo, cyano $C_{1-6}$alkoxycarbonyl, amino, $C_{1-6}$alkylamino, $(C_{1-6}$alkyl amino, carbamoyl, N-($C_{1-6}$alkyl)carbamoyl, N-($C_{1-6}$alkyl$)_2$carbamoyl, $C_{1-6}$alkanoylamino, $C_{1-6}$alkanoyl(N—$C_{1-6}$alkyl) amino, trifluoromethyl, trifluoromethoxy, formyl, $C_{1-6}$alkanoyl, $C_{1-6}$alkyl, $C_{2-6}$alkenyl, $C_{2-6}$alkynyl, N-($C_{1-6}$alkyl)aminosulphonyl, hydroxymethyl, hydroxyacetyl, N-($C_{1-6}$alkyl$)_2$aminosulphonyl, $C_{1-6}$alkanoylaminosulphonyl, $C_{1-6}$alkanoyl(N—$C_{1-6}$ alkyl)aminosulphonyl, $C_{1-6}$alkylsulphonylaminocarbonyl, $C_{1-6}$alkylsulphonyl(N—$C_{1-6}$alkyl)aminocarbonyl, $C_{1-6}$alkoxy, $C_{2-6}$alkenyloxy, phenyl optionally substituted by one or more $R^8$, naphthyl optionally substituted by one or more $R^8$ and a heterocyclic group optionally substituted on a ring carbon by one or more $R^8$ and if said heterocyclic group contains an —NH— moiety that nitrogen may be optionally substituted by a group selected from D;

V is selected from any of the values defined for P, phenyl optionally substituted by one or more P, naphthyl optionally substituted by one or more P, a heterocyclic group optionally substituted on a ring carbon by one or more P and if said heterocyclic group contains an —NH— moiety that nitrogen may be optionally substituted by a group selected from D or $C_{3-6}$cycloalkyl optionally substituted with one or more P;

T is selected from —O—, —C(O)—, —NH—, —N(N—$C_{1-6}$alkyl)—, —C(O)NH—, —NHC(O)—, —C(O)N(N—$C_{1-6}$alkyl)—, —N(N—$C_{1-6}$alkyl)C(O)—, —SO$_2$—, —C(S)—, —C(S)NH—, —NHC(S)—, —C(S)N(N—$C_{1-6}$alkyl)— and —N(N—$C_{1-6}$alkyl)C(S)—;

M is selected from —O—, —N($R^{12}$)—, —C(O)—, —N($R^{12}$)C(O)—, —C(O)N($R^{12}$)—, —S(O)$_n$—, —OC(O)—, —C(O)O—, —N($R^{12}$)C(O)O—, —OC(O)N($R^{12}$)—, —C(S)N($R^{12}$—, —N($R^{12}$)C(S)—, —SO$_2$N($R^{12}$)—, —N($R^{12}$)SO$_2$— and —N($R^{12}$)C(O)N($R^{12}$)—, —N($R^{12}$)C(S)N($R^{12}$)—, —SO$_2$NHC(O)—, —SO$_2$N($R^{12}$)C(O)—, —C(O)NHSO$_2$—, —C(O)N($R^{12}$)SO$_2$— or M is a direct bond;

D is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl$)_2$carbamoyl, benzoyl, (heterocyclic group)carbonyl, phenylsulphonyl, (heterocyclic group)sulphonyl, phenyl or a carbon linked heterocyclic group, and wherein any $C_{1-6}$alkyl group may be optionally substituted by one or more $R^9$, and wherein any phenyl or heterocyclic group may be optionally substituted on a ring carbon by one or more groups selected from $R^8$ and if a heterocyclic group contains an —NH— moiety that nitrogen may be optionally substituted by a group selected from E;

E is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl$)_2$carbamoyl, $C_{1-6}$alkoxy$C_{1-6}$alkanoyl, phenyl$C_{1-6}$alkyl, benzphenylhenyl$C_{1-6}$alkanoyl, phenyl$C_{1-6}$alkoxycarbonyl and phenylsulphonyl.

$R^9$ is selected from hydroxy, amino, $C_{1-6}$alkylamino, $(C_{1-6}$alkyl$)_2$amino, carboxy, $C_{1-6}$alkoxy, carbamoyl, N-($C_{1-6}$alkyl)carbamoyl, N-($C_{1-6}$alkyl$)_2$carbamoyl, formyl, sulphamoyl, N—$C_{1-6}$alkylaminosulphonyl, N-($C_{1-6}$alkyl$)_2$aminosulphonyl, $C_{1-6}$alkylsulphonylamino, $C_{1-6}$alkanoylamino, a heterocyclic group optionally substituted on a ring carbon by one or more $R^8$ and if said heterocyclic group contains an —NH— moiety that nitrogen may be optionally substituted by a group selected from D, phenyl optionally substituted by one or more $R^8$, naphthyl optionally substituted by one or more $R^8$, $C_{1-6}$alkylsulphanyl, $C_{1-6}$alkylsulphinyl and $C_{1-6}$alkylsulphonyl;

$R^{10}$ is carboxy, carbamoyl, N-($C_{1-6}$alkyl)carbamoyl, N-($C_{1-6}$alkyl$)_2$carbamoyl, sulphamoyl, N-($C_{1-6}$alkyl)aminosulphonyl, N-($C_{1-6}$alkyl$)_2$aminosulphonyl, $C_{1-6}$alkylsulphanyl, $C_{1-6}$alkylsulphinyl, $C_{1-6}$alkylsulphonyl, $C_{1-6}$alkoxycarbonyl, $C_{1-6}$alkanoylamino, a heterocyclic group optionally substituted on a ring carbon by one or more $R^8$ and if said heterocyclic group contains an —NH— moiety that nitrogen may be optionally substituted by a group selected from D, phenyl optionally substituted by one or more $R^8$ or naphthyl optionally substituted by one or more $R^8$;

$R^{11}$ is a heterocyclic group optionally substituted on a ring carbon by one or more $R^8$ and if said heterocyclic group contains an —NH— moiety that nitrogen may be optionally substituted by a group selected from D, phenyl optionally substituted by one or more $R^8$, $C_{3-6}$cycloalkyl optionally substituted by one or more $R^8$, or naphthyl optionally substituted by one or more $R^8$;

$R^{12}$ is hydrogen or $C_{1-6}$alkyl optionally substituted with $R^{13}$ with the proviso that $R^{13}$ is not a substituent on the carbon attached to the nitrogen atom of M;

$R^{13}$ is halo, hydroxy, amino, cyano, nitro, trifluoromethyl, trifluoromethoxy, $C_{1-6}$alkyl, $C_{2-6}$alkenyl, $C_{2-6}$alkynyl, $C_{1-6}$alkylamino, $(C_{1-6}$alkyl$)_2$amino, $C_{1-6}$alkanoylamino, $C_{1-6}$alkanoyl(N—$C_{1-6}$alkyl) amino, $C_{1-6}$alkylsulphonylamino, $C_{1-6}$alkylsulphonyl (N—$C_{1-6}$alkyl)amino, thiol, $C_{1-6}$alkylsulphanyl, $C_{1-6}$alkylsulphinyl, $C_{1-6}$alkylsulphonyl, sulphamoyl, N-($C_{1-6}$alkyl)aminosulphonyl, N-($C_{1-6}$alkyl)$_2$ aminosulphonyl, carboxy, carbamoyl, N-($C_{1-6}$alkyl) carbamoyl, N-($C_{1-64}$alkyl)$_2$carbamoyl, $C_{1-6}$alkoxycarbonyl, $C_{1-6}$alkanoyl or formyl;

n is 0–2;

and pharmaceutically acceptable salts or in vivo hydrolysable esters thereof.

Preferred values for $R^1$, $R^2$, $R^3$, $R^4$, $R^5$, X and Y—Z are as follows Preferably $R^1$ and $R^2$ are each independently selected from hydrogen, $C_{1-6}$alkyl, $C_{2-6}$alkenyl, $C_{3-6}$cycloalkyl, $C_{1-6}$alkyl substituted by a heterocyclic group, $C_{1-6}$alkyl substituted by phenyl (which phenyl is optionally substituted by one or more substituents selected from halo, trifluoromethoxy, a heterocyclic group and trifluoromethyl), and phenyl which is optionally substituted by one or more substituents selected from halo, $C_{1-4}$alkoxy, carbamoyl, trifluoromethyl, $C_{1-4}$alkyl, nitro, hydroxy, cyano, $C_{1-6}$alkanolyamino, $C_{1-6}$alkylsulphonyl, $C_{1-6}$alkanoyl and sulphamoyl, or $R^1$ and $R^2$ together with the nitrogen group to which they are attached form morpholino or piperazine.

More preferably $R^1$ and $R^2$ are each independently selected from hydrogen, $C_{1-5}$alkyl, $C_3$alkenyl, $C_{3-6}$cycloalkyl, pyridyl$CH_2$—, thienyl$CH_2$—, 1,3-benzodioxyl$CH_2$—, phenyl$CH_2$— (which phenyl is optionally substituted by one or more substituents selected from fluoro, chloro, trifluoromethoxy, thiadiazole, and trifluoromethyl) and phenyl which is optionally substituted by one or more substituents selected from fluoro, chloro, bromo, iodo, methoxy, hydroxy, carbamoyl, $C_{1-4}$alkyl, trifluoromethyl, nitro, cyano, sulphamoyl, $C_{1-2}$alkanolyamino, mesyl and $C_{1-2}$alkanoyl, or $R^1$ and $R^2$ together with the nitrogen group to which they are attached form morpholino or piperazine.

Particularly $R^1$ and $R^2$ are each independently selected from hydrogen, methyl, ethyl, propenyl and phenyl which is substituted by one substituent selected from methoxy, chloro, iodo, hydroxy, carbamoyl, cyano, acetylamino, mesyl, acetyl and sulphamoyl, or $R^1$ and $R^2$ together with the nitrogen group to which the are attached form morpholino.

More particularly $R^1$ and $R^2$ are each independently selected from hydrogen and phenyl which is substituted by one substituent selected from methoxy, hydroxy, carbamoyl, cyano, acetyl, mesyl and sulphamoyl.

Preferred combinations of $R^1$ and $R^2$ are as follows.

Preferably $R^1$ and $R^2$ are both methyl or ethyl, or one of $R^1$ and $R^2$ is methyl, ethyl or optionally substituted phenyl and the other is hydrogen, or $R^1$ and $R^2$ together with the nitrogen to which they are attached form morpholino.

More preferably one of $R^1$ and $R^2$ is hydrogen and the other is phenyl substituted with one substituent selected from methoxy, hydroxy, carbamoyl, cyano, acetyl, mesyl and sulphamoyl.

In another aspect of the invention, preferably $R^1$ and $R^2$ are each independently selected from i) hydrogen;

ii) $C_{1-6}$alkyl optionally substituted with one or more hydroxy, halo, $C_{1-6}$alkoxy (optionally substituted with one or more hydroxy), $C_{1-6}$alkoxycarbonyl, $C_{1-6}$alkanoylamino, N,N-($C_{1-6}$alkyl)$_2$amino, $C_{1-6}$alkylsulphanyl, N-($C_{1-6}$alkyl)carbamoyl (optionally substituted with one or more $C_{1-6}$alkoxycarbonyl), phenyl (optionally substituted with one or more halo, trifluoromethyl, $C_{1-6}$alkoxy, $C_{1-6}$alkyl, trifluoromethoxy, thiadiazolyl or sulphamoyl), pyridyl, thienyl, 1,3-benzodioxolyl, morpholino, piperidinyl, tetrahydrofuran and imidazolyl;

iii) phenyl optionally substituted with one or more halo, trifluoromethyl, nitro, cyano, hydroxy, sulphamoyl, carbamoyl, amino, formyl, carboxy, $C_{1-4}$alkyl (optionally substituted with one or more hydroxy), $C_{1-4}$alkoxy (optionally substituted with one or more phenyl), $C_{1-6}$alkanoyl, $C_{1-6}$alkoxycarbonyl, $C_{1-6}$alkanoylamino, $C_{1-6}$alkylsulphanyl (optionally substituted with one or more hydroxy or $C_{1-6}$alkoxy), $C_{1-6}$alkylsulphonyl (optionally substituted with one or more hydroxy or $C_{1-6}$alkoxy), N-($C_{1-6}$alkyl)amino (optionally substituted with one or more hydroxy), N-($C_{1-6}$alkyl)carbamoyl (optionally substituted with one or more $C_{1-6}$alkoxy, N,N-($C_{1-6}$alkyl)$_2$amino, hydroxy or tetrahydrofuran), N,N-($C_{1-6}$alkyl)$_2$carbamoyl (optionally substituted with one or more hydroxy or $C_{1-6}$alkoxy), N-($C_{2-6}$alkenyl) carbamoyl, N-($C_{3-6}$cycloalkyl)carbamoyl (optionally substituted with one or more hydroxy), N-($C_{2-6}$alkenyl) aminosulphonyl, N-($C_{3-6}$cycloalkyl)aminosulphonyl (optionally substituted with one or more hydroxy), N-($C_{1-6}$alkyl)aminosulphonyl (optionally substituted with one or more hydroxy, amino or N,N-($C_{1-6}$alkyl)$_2$ amino), N,N-($C_{1-6}$alkyl)$_2$aminosulphonyl (optionally substituted with one or more hydroxy), $C_{1-6}$alkanoylaminosulphonyl, $C_{1-6}$alkylsulphonylaminocarbonyl, morpholinosulphonyl, piperazinylcarbonyl (optionally substituted on a ring nitrogen by $C_{1-6}$alkyl), morpholinocarbonyl, pyrrolidinylsulphonyl (optionally substituted with one or more hydroxy);

iv) $C_{3-6}$cycloalkyl (optionally substituted with one or more hydroxy);

v) $C_{2-6}$alkenyl, vi) $C_{1-6}$alkanoyl [optionally substituted with one or more amino or phenyl (wherein said phenyl is optionally substituted with one or more halo)];

vii) benzoyl (optionally substituted with one or more halo, $C_{1-6}$alkylsulphanyl, $C_{1-6}$alkylsulphonyl, cyano, benzyloxy, $C_{1-6}$alkoxy, trifluoromethyl, N,N-($C_{1-6}$alkyl)$_2$aminosulphonyl, hydroxy);

viii) N-phenylcarbamoyl; or ix) a heterocyclic group selected from tetrahydrofuran, piperidinyl (optionally substituted on a ring nitrogen with $C_{1-6}$alkyl), pyridyl (optionally substituted with one or more trifluoromethyl, $C_{1-6}$alkyl or halo), pyrimidinyl (optionally substituted with one or more $C_{1-6}$alkyl or N,N-($C_{1-6}$alkyl)$_2$amino), thienyl (optionally substituted with one or more carbamoyl), isoxazolyl (optionally substituted with one or more $C_{1-6}$alkyl) and pyrazinyl (optionally substituted with one or more $C_{1-6}$alkyl);

or $R^1$ and $R^2$ together with the nitrogen atom to which they are attached form morpholino, piperidinyl [optionally substituted with one or more hydroxy, $C_{1-6}$alkyl (wherein said $C_{1-6}$alkyl is optionally substituted with hydroxy) or pyrrolidinyl], piperazinyl [optionally substituted on a ring nitrogen by $C_{1-6}$alkoxycarbonyl, $C_{1-6}$alkanoyl (wherein said $C_{1-6}$alkanoyl is optionally substituted with one or more $C_{1-6}$alkoxy, $C_{1-6}$alkanoylamino, hydroxy or amino), $C_{1-6}$alkyl (wherein said $C_{1-6}$alkyl is optionally substituted with one or more hydroxy), $C_{1-6}$alkylsulphonyl, phenylsulphonyl (wherein said phenylsulphonyl is optionally substituted with one or more $C_{1-6}$alkylsulphonyl) morpholinocarbonyl or tetrahydrofurylcarbonyl], indolinyl, pyrrolyl, thiazolidinyl, pyrrolidinyl (optionally substituted with one or more hydroxy), thiomorpholino, 3-pyrrolinyl or homopiperazinyl (optionally substituted on a ring nitrogen with $C_{1-6}$alkyl).

More preferably $R^1$ and $R^2$ are each independently selected from:

i) hydrogen;

ii) $C_{1-6}$alkyl optionally substituted with one or more hydroxy, halo, $C_{1-6}$alkoxy (optionally substituted with one or more hydroxy), $C_{1-6}$alkoxycarbonyl, N,N-$(C_{1-6}$alkyl$)_2$amino, $C_{1-6}$alkylsulphanyl, N-$(C_{1-6}$alkyl)carbamoyl (optionally substituted with one or more $C_{1-6}$alkoxycarbonyl), phenyl (optionally substituted with one or more halo or sulphamoyl), pyridyl, thienyl, 1,3-benzodioxolyl, morpholino, piperidinyl, tetrahydrofuran and imidazolyl;

iii) phenyl optionally substituted with one or more halo, trifluoromethyl, nitro, cyano, hydroxy, sulphamoyl, carbamoyl, amino, formyl, carboxy, $C_{1-4}$alkyl (optionally substituted with one or more hydroxy), $C_{1-4}$alkoxy (optionally substituted with one or more phenyl), $C_{1-6}$alkanoyl, $C_{1-6}$alkoxycarbonyl, $C_{1-6}$alkanoylamino, $C_{1-6}$alkylsulphanyl (optionally substituted with one or more hydroxy or $C_{1-6}$alkoxy), $C_{1-6}$alkylsulphonyl (optionally substituted with one or more hydroxy or $C_{1-6}$alkoxy), N-$(C_{1-6}$alkyl)amino (optionally substituted with one or more hydroxy), N-$(C_{1-6}$alkyl)carbamoyl (optionally substituted with one or more $C_{1-6}$alkoxy, N,N-$(C_{1-6}$alkyl$)_2$amino, hydroxy or tetrahydrofuran), N,N-$(C_{1-6}$alkyl$)_2$carbamoyl (optionally substituted with one or more hydroxy or $C_{1-6}$alkoxy), N-$(C_{2-6}$alkenyl)carbamoyl, N-$(C_{3-4}$cycloalkyl)carbamoyl (optionally substituted with one or more hydroxy), N-$(C_{2-6}$alkenyl)aminosulphonyl, N-$(C_{3-6}$cycloalkyl)aminosulphonyl (optionally substituted with one or more hydroxy), N-$(C_{1-6}$alkyl)aminosulphonyl (optionally substituted with one or more hydroxy, or N,N-$(C_{1-6}$alkyl$)_2$amino), N,N-$(C_{1-6}$alkyl$)_2$aminosulphonyl (optionally substituted with one or more hydroxy), $C_{1-6}$alkanoylaminosulphonyl, $C_{1-6}$alkylsulphonylaminocarbonyl, morpholinosulphonyl, piperazinylcarbonyl (optionally substituted on a ring nitrogen by $C_{1-6}$alkyl), morpholinocarbonyl, pyrrolidinylsulphonyl (optionally substituted with one or more hydroxy);

iv) $C_{3-6}$cycloalkyl (optionally substituted with one or more hydroxy);

v) $C_{2-6}$alkenyl, vi) $C_{1-6}$alkanoyl [optionally substituted with one or more phenyl (wherein said phenyl is optionally substituted with one or more halo)];

vii) benzoyl (optionally substituted with one or more halo, $C_{1-6}$alkylsulphanyl, $C_{1-6}$alkylsulphonyl, cyano, $C_{1-6}$alkoxy, trifluoromethyl, N,N-$(C_{1-6}$alkyl$)_2$aminosulphonyl, hydroxy);

viii) a heterocyclic group selected from tetrahydrofuran, pyridyl (optionally substituted with one or more trifluoromethyl, $C_{1-6}$alkyl or halo), pyrimidinyl (optionally substituted with one or more $C_{1-6}$alkyl or N,N-$(C_{1-6}$alkyl$)_2$amino), thienyl (optionally substituted with one or more carbamoyl), isoxazolyl (optionally substituted with one or more $C_{1-6}$alkyl) and pyrazinyl (optionally substituted with one or more $C_{1-6}$alkyl);

or $R^1$ and $R^2$ together with the nitrogen atom to which they are attached form morpholino, piperidinyl [optionally substituted with one or more hydroxy, $C_{1-6}$alkyl (wherein said $C_{1-6}$alkyl is optionally substituted with hydroxy) or pyrrolidinyl], piperazinyl [optionally substituted on a ring nitrogen by $C_{1-6}$alkoxycarbonyl, $C_{1-6}$alkanoyl (wherein said $C_{1-6}$alkanoyl is optionally substituted with one or more $C_{1-6}$alkoxy, $C_{1-6}$alkanoylamino, hydroxy or amino), $C_{1-6}$alkyl (wherein said $C_{1-6}$alkyl is optionally substituted with one or more hydroxy), $C_{1-6}$alkylsulphonyl, phenylsulphonyl (wherein said phenylsulphonyl is optionally substituted with one or more $C_{1-6}$alkylsulphonyl) or morpholinocarbonyl], indolinyl, thiazolidinyl, pyrrolidinyl (optionally substituted with one or more hydroxy), thiomorpholino or 3-pyrrolinyl.

Particularly $R^1$ and $R^2$ are each independently selected from:

i) hydrogen;

ii) $C_{1-6}$alkyl optionally substituted with one or more hydroxy, $C_{1-6}$alkoxy, $C_{1-6}$alkoxycarbonyl, $C_{1-6}$alkylsulphanyl, N-$(C_{1-6}$alkyl)carbamoyl (optionally substituted with one or more $C_{1-6}$alkoxycarbonyl), phenyl (optionally substituted with one or more sulphamoyl), morpholino and tetrahydrofuran;

iii) phenyl optionally substituted with one or more halo, trifluoromethyl, hydroxy, sulphamoyl, amino, $C_{1-4}$alkyl, $C_{1-4}$alkoxy, $C_{1-6}$alkoxycarbonyl, $C_{1-6}$alkylsulphanyl (optionally substituted with one or more hydroxy or $C_{1-6}$alkoxy), $C_{1-6}$alkylsulphonyl (optionally substituted with one or more hydroxy or $C_{1-6}$alkoxy), N-$(C_{1-6}$alkyl)amino (optionally substituted with one or more hydroxy), N-$(C_{1-6}$alkyl)carbamoyl (optionally substituted with one or more $C_{1-6}$alkoxy, hydroxy or tetrahydrofuran), N,N-$(C_{1-6}$alkyl$)_2$carbamoyl (optionally substituted with one or more hydroxy), N-$(C_{2-6}$alkenyl)carbamoyl, N-$(C_{2-6}$alkenyl)aminosulphonyl, N-$(C_{1-6}$alkenyl)aminosulphonyl (optionally substituted with one or more hydroxy or N,N-$(C_{1-6}$alkyl$)_2$amino), N,N-$(C_{1-6}$alkyl$)_2$aminosulphonyl, $C_{1-6}$alkylsulphonylaminocarbonyl, morpholinosulphonyl, pyrrolidinylsulphonyl (optionally substituted with one or more hydroxy);

iv) $C_{3-6}$cycloalkyl (optionally substituted with one or more hydroxy);

v) $C_{2-6}$alkenyl, vi) $C_{1-6}$alkanoyl [optionally substituted with one or more phenyl vii) benzoyl (optionally substituted with one or more halo, cyano, $C_{1-6}$alkoxy, hydroxy);

viii) a heterocyclic group selected from pyridyl (optionally substituted with one or more trifluoromethyl, $C_{1-6}$alkyl or halo), pyrimidinyl (optionally substituted with one or more $C_{1-6}$alkyl or N,N-$(C_{1-6}$alkyl$)_2$amino), thienyl (optionally substituted with one or more carbamoyl), isoxazolyl (optionally substituted with one or more $C_{1-6}$alkyl) and pyrazinyl (optionally substituted with one or more $C_{1-6}$alkyl);

or $R^1$ and $R^2$ together with the nitrogen atom to which they are attached form morpholino, piperidinyl

[optionally substituted with one or more hydroxy or $C_{1-6}$alkyl (wherein said $C_{1-6}$alkyl is optionally substituted with hydroxy)], piperazinyl [optionally substituted on a ring nitrogen by $C_{1-6}$alkoxycarbonyl, $C_{1-6}$alkanoyl (wherein said $C_{1-6}$alkanoyl is optionally substituted with one or more $C_{1-6}$alkoxy, $C_{1-6}$alkanoylamino, hydroxy or amino), $C_{1-6}$alkylsulphonyl or morpholinocarbonyl], indolinyl or 3-pyrrolinyl.

More particularly $R^1$ and $R^2$ are each independently selected from hydrogen, methyl, cyclopropyl, 4-hydroxycyclohexyl, 2-hydroxyethyl, 2-hydroxypropyl, 2,3-dihydroxypropyl, 4-(morpholinosulphonyl)phenyl, pyrid-3-yl, 2-carbamoylthien-3-yl, 2-chloropyrid-3-yl, 5-chloropyrid-2-yl, 5-methylpyrid-2-yl, pyrimid-2-yl, 4,6-dimethylpyrimid-2-yl or 5,6-dimethylpyrazin-2-yl;

or $R^1$ and $R^2$ together with the nitrogen atom to which they are attached form 4-hydroxypiperidinyl or 1-(hydroxyacetyl)piperazin-4-yl.

In a further aspect of the invention, preferably $R^1$ and $R^2$ are independently selected from i) hydrogen;

ii) $C_{1-6}$alkyl or $C_{3-6}$cycloalkyl optionally substituted with one or more $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, $C_{1-6}$alkoxycarbonyl, amino, $C_{1-6}$alkylamino, $(C_{1-6}alkyl)_2$amino, carbamoyl, N-$(C_{1-6}$alkyl)carbamoyl, N-$(C_{1-6}alkyl)_2$carbamoyl, $C_{1-6}$alkanoylamino, $C_{1-6}$alkanoyl(N—$C_{1-6}$alkyl)amino, $C_{1-6}$alkanoyl, $C_{2-6}$alkenyl, $C_{2-6}$alkynyl, N-$(C_{1-6}$alkyl)aminosulphonyl, hydroxymethyl, hydroxyacetyl or N—$(C_{1-6}alkyl)_2$aminosulphonyl;

iii) a heterocyclic group selected from pyridyl, pyrimidyl, pyridazinyl or pyrazinyl, wherein said heterocyclic group is optionally substituted with one or more $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, C1–6alkoxycarbonyl, amino, $C_{1-6}$alkylamino, $(C_{1-6}alkyl)_2$amino, carbamoyl, N-$(C_{1-6}$alkyl)carbamoyl, N-$(C_{1-6}alkyl)_2$carbamoyl, $C_{1-6}$alkanoylamino, $C_{1-6}$alkanoyl(N—$C_{1-6}$alkyl)amino, trifluoromethyl, trifluoromethoxy, $C_{1-6}$alkanoyl, $C_{2-6}$alkenyl, $C_{2-6}$alkynyl, N-$(C_{1-6}$alkyl)aminosulphonyl, hydroxymethyl, hydroxyacetyl or N-$(C_{1-6}alkyl)_2$aminosulphonyl;

or $R^1$ and $R^2$ together with the nitrogen atom to which they are attached form piperidinyl or piperazinyl; wherein said piperidinyl and piperazinyl may be optionally substituted on a ring carbon by one or more groups selected from $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, $C_{1-6}$alkoxycarbonyl, amino, $C_{1-6}$alkylamino, $(C_{1-6}alkyl)_2$amino, carbamoyl, N-$(C_{1-6}$alkyl)carbamoyl, N-$(C_{1-6}alkyl)_2$carbamoyl, $C_{1-6}$alkanoylamino, $C_{1-6}$alkanoyl(N—$C_{1-6}$alkyl)amino, $C_{1-6}$alkanoyl, $C_{2-6}$alkenyl, $C_{2-6}$alkynyl, N-$(C_{1-6}$alkyl) aminosulphonyl, hydroxymethyl, hydroxyacetyl or N-$(C_{1-6}alkyl)_2$aminosulphonyl; and said piperazinyl may be optionally substituted on the ring nitrogen by a group selected from $C_{1-6}$alkanoyl, $C_{1-6}$alkylsulphonyl, $C_{1-6}$alkoxycarbonyl, carbamoyl, N-$(C_{1-6}$alkyl)carbamoyl and N,N-$(C_{1-6}alkyl)_2$carbamoyl; and wherein any $C_{1-6}$alkyl group may be optionally substituted by one or more groups selected from hydroxy, amino, $C_{1-6}$alkylamino, $(C_{1-6}alkyl)_2$amino, carboxy, $C_{1-6}$alkoxy, carbamoyl, N-$(C_{1-6}$alkyl)carbamoyl, N-$(C_{1-6}alkyl)_2$carbamoyl, sulphamoyl, N—$C_{1-6}$alkylaminosulphonyl, N-$(C_{1-6}alkyl)_2$aminosulphonyl, $C_{1-6}$alkylsulphonylamino, $C_{1-6}$alkanoylamino, $C_{1-6}$alkylsulphanyl, $C_{1-6}$alkylsulphinyl and $C_{1-6}$alkylsulphonyl.

Preferably the $R^1R^2NSO_2$— group is para to Y—Z.

In one aspect of the invention $R^3$ and $R^4$ are independently $C_k$alkyl optionally substituted by from 1 to 2k+1 atoms selected from fluoro and chloro wherein k is 1–3.

Preferably $R^3$ and $R^4$ are independently $C_k$alkyl optionally substituted by from 1 to 2k+1 atoms selected from fluoro and chloro, wherein k is 1–3, or $R^3$ and $R^4$, together with the carbon atom to which they are attached, form a cyclopropane ring optionally substituted by from 1 to 4 fluorine atoms.

More preferably $R^3$ and $R^4$ are independently $C_k$alkyl optionally substituted by from 1 to 2k+1 fluorine atoms, wherein k is 1–2, or $R^3$ and $R^4$, together with the carbon atom to which they are attached, form a cyclopropane ring optionally substituted by from 1 to 4 fluorine atoms.

Particularly $R^3$ and $R^4$ are independently methyl, fluoromethyl, difluoromethyl, trifluoromethyl, 2,2,2-trifluoroethyl and perfluoroethyl, or $R^3$ and $R^4$, together with the carbon atom to which they are attached, form a cyclopropane ring optionally substituted by from 1 to 4 fluorine atoms.

More particularly $R^3$ and $R^4$ are independently methyl, fluoromethyl, difluoromethyl and trifluoromethyl, or $R^3$ and $R^4$, together with the carbon atom to which they are attached, form a cyclopropane ring optionally substituted by from 1 to 4 fluorine atoms.

Preferred combinations of $R^3$ and $R^4$ are as follows.

Preferably $R^3$ and $R^4$ are both methyl or one of $R^3$ and $R^4$ is methyl and the other is trifluoromethyl.

More preferably one of $R^3$ and $R^4$ is methyl and the other is trifluoromethyl.

Where applicable, the R-configuration generally represents a preferred stereochemistry for compounds of formula (I).

Preferably $R^1$ is ortho to Y—Z.

Preferably $R^5$ is selected from halo, nitro, $C_{1-4}$alkyl, $C_{1-4}$alkoxy, hydroxy, hydrogen, amino, carboxy and sulphamoyl.

More preferably $R^5$ is selected from fluoro, chloro, bromo, nitro, methyl, ethyl, methoxy, ethoxy, hydroxy, hydrogen, amino, carboxy and sulphamoyl.

Particularly $R^5$ is selected from fluoro, chloro, nitro and methyl.

More particularly $R^5$ is selected from fluoro and chloro.

Particularly preferred $R^5$ is chloro ortho to Y—Z.

In another aspect of the invention preferably $R^5$ is selected from halo, nitro, $C_{1-4}$alkyl, $C_{1-4}$alkoxy, $C_{2-4}$alkenyl, $C_{2-4}$alkynyl, hydroxy, hydrogen, amino, carboxy and sulphamoyl.

More preferably $R^5$ is selected from fluoro, chloro, bromo, nitro, methyl, ethyl, methoxy, ethoxy, ethenyl, ethynyl, hydroxy, hydrogen, amino, carboxy and sulpharmoyl.

Particularly $R^5$ is selected from fluoro, chloro, nitro, methyl, ethenyl and ethynyl.

Preferably X is phenyl.

Preferably Y—Z is selected from —NHC(O)—, —NHC(S)—, trans-vinylene and ethynylene.

More preferably Y—Z is selected from —NHC(O)— and —NHC(S)—.

Particularly Y—Z is —NHC(O)—.

In a particular embodiment of the present invention there is provided a compound of formula (I) or a pharmaceutically acceptable salt or an in vivo hydrolysable ester thereof (as herein before defined). Particular and preferred values are those mentioned above.

According to another aspect of the present invention there is provided a compound of the formula (Ia)

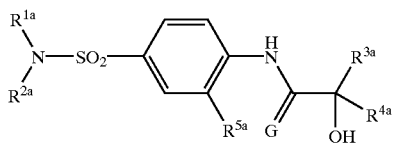

(Ia)

wherein
$R^{1a}$ and $R^{2a}$ are independently selected from hydrogen, $C_{1-6}$alkyl, $C_{2-6}$alkenyl, $C_{3-6}$Cycloalkyl, $C_{1-6}$alkyl substituted by a heterocyclic group, $C_{1-6}$alkyl substituted by phenyl (which phenyl is optionally substituted by one or more halo, trifluoromethoxy, a heterocyclic group or trifluoromethyl) and phenyl which is optionally substituted by one or more halo, $C_{1-4}$alkoxy, carbamoyl, trifluoromethyl, $C_{1-4}$alkyl, nitro, hydroxy, cyano, $C_{1-6}$alkanolyamino, $C_{1-6}$alkylsulphonyl, $C_{1-6}$alkanoyl or sulphamoyl, or $R^{1a}$ and $R^{2a}$ together with the nitrogen group to which the are attached form morpholino or piperazine;

$R^{3a}$ and $R^{4a}$ are independently methyl optionally substituted by from 1–3 fluoro;

$R^{5a}$ is selected from halo, nitro, $C_{1-6}$alkyl, $C_{1-6}$alkoxy, hydroxy, hydrogen, amino, carboxy and sulphamoyl;

G is O or S.;

with the proviso that where $R^{1a}$ and $R^{2a}$ are selected from hydrogen, $C_{1-3}$alkyl or phenyl (which phenyl is optionally substituted by one or two substituents selected from halo, $C_{1-4}$alkoxy, $C_{1-4}$alkyl, hydroxy or cyano), $R^{5a}$ is nitro, $C_{1-4}$alkyl, $C_{1-4}$alkoxy or hydrogen and $R^{3a}$ and $R^{4a}$ are not both methyl, G must be S;

and pharmaceutically acceptable salts or in vivo hydrolysable esters thereof.

Where applicable, the R-configuration generally represents a preferred stereochemistry for compounds of formula (Ia).

A further preferred class of compounds is that of formula (Ib):

(Ib)

wherein
$R^{1b}$ and $R^{2b}$ are independently selected from hydrogen, methyl, ethyl, $C_3$alkenyl or phenyl which is substituted by one of methoxy, chloro, iodo, hydroxy, carbamoyl, cyano, acetylamino, mesyl, acetyl or sulphamoyl, or $R^{1b}$ and $R^{2b}$ together with the nitrogen group to which the are attached form morpholino.

and pharmaceutically acceptable salts or in vivo hydrolysable esters thereof.

In a further aspect of the invention there is provided a compound of formula (Ib) wherein $R^{1b}$ and $R^{2b}$ are independently selected from:

i) hydrogen;

ii) $C_{1-6}$alkyl or $C_{3-6}$cycloalkyl optionally substituted with one or more $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, $C_{1-6}$alkoxycarbonyl, amino, $C_{1-6}$alkylamino, $(C_{1-6}$alkyl$)_2$amino, carbamoyl, N-$(C_{1-6}$alkyl$)$carbamoyl, N-$(C_{1-6}$alkyl$)_2$carbamoyl, $C_{1-6}$alkanoylamino, $C_{1-6}$alkanoyl(N—$C_{1-6}$alkyl)amino, $C_{1-6}$alkanoyl, $C_{2-6}$alkenyl, $C_{2-6}$alkynyl, N-$(C_{1-6}$alkyl$)$aminosulphonyl, hydroxymethyl, hydroxyacetyl or N-$(C_{1-6}$alkyl$)_2$aminosulphonyl;

iii) a heterocyclic group selected from pyridyl, pyrimidyl, pyridazinyl or pyrazinyl, wherein said heterocyclic group is optionally substituted with one or more $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, $C_{1-6}$alkoxycarbonyl, amino, $C_{1-6}$alkylamino, $(C_{1-6}$alkyl$)_2$amino, carbamoyl, N-$(C_{1-6}$alkyl$)$carbamoyl, N-$(C_{1-6}$alkyl$)_2$carbamoyl, $C_{1-6}$alkanoylamino, $C_{1-6}$alkanoyl(N—$C_{1-6}$alkyl)amino, trifluoromethyl, trifluoromethoxy, $C_{1-6}$alkanoyl, $C_{2-6}$alkenyl, $C_{2-6}$alkynyl, N-$(C_{1-6}$alkyl$)$aminosulphonyl, hydroxymethyl, hydroxyacetyl or N-$(C_{1-6}$alkyl$)_2$aminosulphonyl;

or $R^{1b}$ and $R^{2b}$ together with the nitrogen atom to which they are attached form piperidinyl or piperazinyl; wherein said piperidinyl and piperazinyl may be optionally substituted on a ring carbon by one or more groups selected from $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulpharmoyl, carboxy, $C_{1-6}$alkoxycarbonyl, amino, $C_{1-6}$alkylamino, $(C_{1-6}$alkyl$)_2$amino, carbamoyl, N-$(C_{1-6}$alkyl$)$carbamoyl, N-$(C_{1-6}$alkyl$)_2$carbamoyl, $C_{1-6}$alkanoylamino, $C_{1-6}$alkanoyl(N—$C_{1-6}$alkyl)amino, $C_{1-6}$alkanoyl, $C_{2-6}$alkenyl, $C_{2-6}$alkynyl, N-$(C_{1-4}$alkyl$)$aminosulphonyl, hydroxymethyl, hydroxyacetyl or N-$(C_{1-6}$alkyl$)_2$aminosulphonyl; and said piperazinyl may be optionally substituted on the ring nitrogen by a group selected from $C_{1-6}$alkanoyl, $C_{1-6}$alkylsulphonyl, $C_{1-6}$alkoxycarbonyl, carbamoyl, N-$(C_{1-6}$alkyl$)$carbamoyl and N,N-$(C_{1-6}$alkyl$)_2$carbamoyl; and wherein any $C_{1-6}$alkyl group may be optionally substituted by one or more groups selected from hydroxy, amino, $C_{1-6}$alkylamino, $(C_{1-6}$alkyl$)_2$amino, carboxy, $C_{1-6}$alkoxy, carbamoyl, N-$(C_{1-6}$alkyl$)$carbamoyl, N-$(C_{1-6}$alkyl$)_2$carbamoyl, sulphamoyl, N—$C_{1-6}$alkylaminosulphonyl, N-$(C_{1-6}$alkyl$)_2$aminosulphonyl, $C_{1-6}$alkylsulphonylamino, $C_{1-6}$alkanoylamino, $C_{1-6}$alkylsulphanyl, $C_{1-6}$alkylsulphinyl and $C_{1-6}$alkylsulphonyl.

and pharmaceutically acceptable salts or in vivo hydrolysable esters thereof.

Where applicable, the R-configuration generally represents a preferred stereochemistry for compounds of formula (Ib).

A further preferred class of compounds is that of formula (Ic):

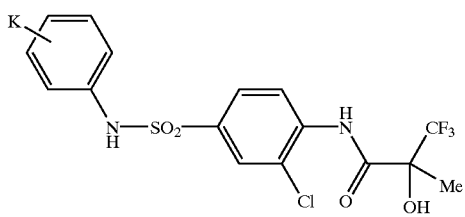

wherein:

K is methoxy, hydroxy, carbamoyl, cyano, acetyl, mesyl, or sulphamoyl, and pharmaceutically acceptable salts or in vivo hydrolysable esters thereof.

Where applicable, the R-configuration generally represents a preferred stereochemistry for compounds of formula (Ic).

Preferred compounds having formula (I) are Examples 1–37, 61–94 and 270 and pharmaceutically acceptable salts or in vivo hydrolysable esters thereof.

Most preferred compounds having formula (I) are Examples 17, 34, 35, 36, 62, 78, 81 and 270 and pharmaceutically acceptable salts or in vivo hydrolysable esters thereof.

In another aspect of the invention, preferred compounds of the invention are any one of Examples 1–272 and pharmaceutically acceptable salts or in vivo hydrolysable esters thereof.

In a further aspect of the invention preferred compounds of the invention are Examples 27, 43, 44, 123, 143, 144, 145, 150, 166, 251, 252, 253, 255, 258, 259, 263 and 261 and pharmaceutically acceptable salts or in vivo hydrolysable esters thereof.

In an additional aspect of the invention preferred compounds of the invention are Examples 143, 145, 251, 252 and 258 and pharmaceutically acceptable salts or in vivo hydrolysable esters thereof.

Preferred aspects of the invention are those which relate to the compound or a pharmaceutically acceptable salt thereof.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which elevates PDH activity and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (I) contain one or more asymmetrically substituted carbon and/or sulphur atoms, and accordingly may exist in, and be isolated as enantiomerically pure, a mixture of diastereoisomers or as a racemate-. Some compounds may exhibit polymorphism. It is to be understood that the present invention encompasses any racemic, optically-active, enantiomerically pure, mixture of diastereoisomers, polymorphic or stereoisomeric form, or mixtures thereof, which form possesses properties useful in the elevation of PDH activity, it being well known in the art how to prepare optically-active forms (for example, by resolution of the racemic form by recrystallisation techniques, by synthesis from optically-active starting materials, by chiral synthesis, by enzymatic resolution, (for example WO 9738124), by biotransformation, or by chromatographic separation using a chiral stationary phase) and how to determine efficacy for the elevation of PDH activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which elevate PDH activity.

A compound of the formula (I), or salt thereof, and other compounds of the invention (as hereinafter defined) may be prepared by any process known to be applicable to the preparation of chemically-related compounds. Such processes include, for example, those illustrated in European Patent Applications, Publication Nos. 0524781, 0617010, 0625516, and in GB 2278054, WO 9323358 and WO 9738124.

Another aspect of the present invention provides a process for preparing a compound of formula (I) or a pharmaceutically acceptable salt or an in vivo hydrolysable ester thereof, which process (in which variable groups are as defined for formula (I) unless otherwise stated) comprises of:

(a) deprotecting a protected compound of formula (II)

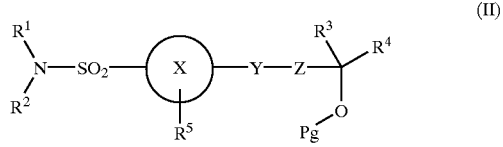

where Pg is an alcohol protecting group;

(b) for a compound of formula (I) in which Y—Z is —NHC(O)—, by coupling an aniline of formula (III):

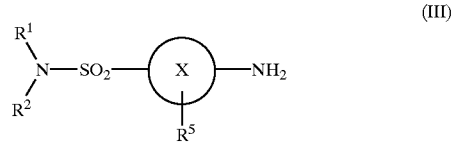

with an acid of formula (IV):

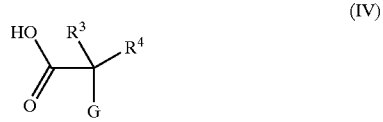

wherein G is a hydroxyl group;

(c) by coupling an aniline of formula (III) with an activated acid derivative of formula (IV) wherein G is a hydroxyl group which may be protected as an ester or ether;

(d) for a compound of formula (I) in which Y—Z is ethynylene, by reacting a alkyne of formula (V):

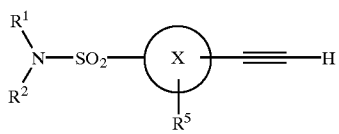
(V)

with a base, followed by treatment with a ketone of formula (VI):

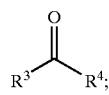
(VI)

(e) for a compound of formula (I) in which Y—Z is trans-vinylene, by reducing a compound of formula (I) in which Y—Z is ethynylene;

(f) for a compound of formula (I) in which Y—Z is trans-vinylene, by dehydration of a diol of formula (VII):

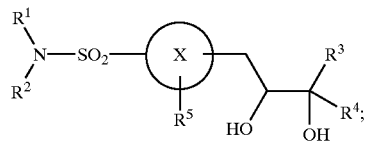
(VII)

(g) for a compound of formula (I) in which Y—Z is trans-vinylene, by base catalysed opening of an epoxide of formula (VIII):

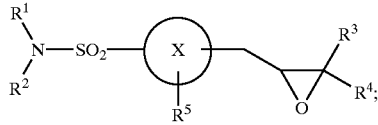
(VIII)

(h) for a compound of formula (I) in which Y—Z is —NHCH$_2$—, by reducing a compound of formula (I) in which Y—Z is —NHC(O)—;

(i) for a compound of formula (I) in which Y—Z is —OCH$_2$—, —SCH$_2$— or —NHCH$_2$— by reacting an ethylene oxide of formula (IX):

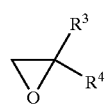
(IX)

with a compound of formula (III) or a compound of formula (X):

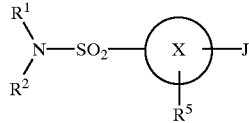
(X)

where J is —OH, —NH$_2$ or —SH;

(j) by reacting a compound of formula (XI):

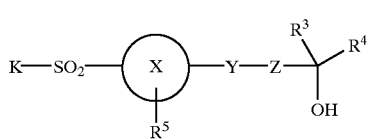
(XI)

where K is a leaving atom or group, and in which Y—Z is OCH$_2$, SCH$_2$ or NHCH$_2$ or —NHC(O)— with an amine of formula R$^1$R$^2$NH;

(k) for a compound of formula (I) in which Y—Z is —NHC(S)—, by reacting a compound of formula (I) in which Y—Z is —NHC(O)— with a sulphur reagent; and thereafter if necessary:
  i) converting a compound of the formula (I) into another compound of the formula (I);
  ii) removing any protecting groups; or
  iii) forming a pharmaceutically acceptable salt or in vivo hydrolysable ester.

Suitable values for Pg are a benzyl group, a silyl group or an acetyl protecting group.

K is a leaving atom or group, suitable values for K are for example a halogen atom such as fluoro or chloro.

Specific conditions of the above reactions are as follows:
a) Suitable reagents for deprotecting an alcohol of formula (II) are for example:
  1) when Pg is benzyl:
    (i) hydrogen in the presence of palladium/carbon catalyst, i.e. hydrogenolysis; or
    (ii) hydrogen bromide or hydrogen iodide;
  2) when Pg is a silyl protecting group:
    (i) tetrabutylammonium fluoride; or
    (ii) aqueous hydrofluoric acid;
  3) when Pg is acetyl:
    i) mild aqueous base for example lithium hydroxide.

The reaction can be conducted in a suitable solvent such as ethanol, methanol, acetonitrile, or dimethylsulphoxide and may conveniently be performed at a temperature in the range of −40 to 100° C.

(b) An aniline of formula (III) and an acid of formula (IV) may be coupled together in the presence of a suitable coupling reagent. Standard peptide coupling reagents known in the art can be employed as suitable coupling reagents, for example thionyl chloride (or oxalyl chloride), carbonyldiimidazole and dicyclohexylcarbodiimide, optionally in the presence of a catalyst such as dimethylaminopyridine or 4-pyrrolidinopyridine, optionally in the presence of a base for example triethylamine, pyridine, or 2,6-dialkyl-pyridines such as 2,6-lutidine or 2,6-di-tert-butylpyridine. Suitable solvents include dimethylacetamide, dichloromethane, benzene, tetrahydrofuran, and dimethylformamide. The coupling reaction may conveniently be performed at a temperature in the range of −40 to 40° C.

(c) An aniline of formula (III) may be coupled with an activated acid derivative of formula (IV) for example acid chlorides, acid anhydrides, or phenyl esters, wherein G is a hydroxyl group which may be suitably protected as a stable ester or ether. This coupling may be achieved optionally in the presence of a base for example triethyl amine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran, and dimethylformamide. The coupling reaction may conveniently be performed at a temperature in the range of −40 to 40° C.;

(d) suitable bases for reacting with a corresponding alkyne of formula (V) are for example lithium diisopropylamide (LDA), n-butyllithium or tert-butyllithium. The reaction with a ketone of formula (IV) may be performed at a temperature in the range of −100 to −40° C. preferably at a temperature in the range of −70 to −40° C. and in a solvent such as tetrahydrofuran, diethyl ether, or 1,2-dimethoxyethane.

(e) A suitable reducing agent for a compound of formula (I) in which Y—Z is trans-vinylene is, for example, lithium aluminium hydride or sodium bis (methoxyethoxy)aluminium hydride. The reaction can be conducted in a suitable solvent such as tetrahydrofuran or diethyl ether, and at a temperature in the range of 0 to 50° C.

(f) Dehydration of a diol of formula (VII) may be conducted in the presence of an acid catalyst (for example p-toluenesulphonic acid), neat or with a solvent such as toluene or dichloromethane at a temperature in the range of 0 to 200° C. preferably a temperature in the range of 20 to 100° C.

(g) Base catalysed opening of an epoxide of formula (VIII) may be carried out in a suitable organic solvent for example, ethers or toluene. Ethers such as tetrahydrofuran are preferred. Suitable bases include potassium tert-butoxide or sodium hydride. The opening may be carried out at a temperature in the range of −50 to 100° C., preferably at a temperature in the range of 0 to 50° C. for example room temperature.

(h) A compound of formula (I) in which Y—Z is —NHC(O)— may be reduced with a suitable reducing agent such as lithium aluminium hydride or borane. The reaction can conveniently be carried out at a temperature in the range of 0° C. to reflux, in solvents such as for example diethyl ether, tetrahydrofuran, or 1,2-dimethoxyethane.

(i) An ethylene oxide of formula (IX) may be reacted with a corresponding compound of formula (III) or a compound of formula (X) in the presence of a base for example sodium hydride or triethylamine. The reaction can be conducted at reflux in a solvent such as dichloromethane, tetrahydrofuran, or diethyl ether.

(j) A compound of formula (XI) where K is a leaving atom or group, for example a halogen atom such as fluoro or chloro and in which Y—Z is OCH$_2$, SCH$_2$ or NHCH$_2$ or —NHC(O)— may be reacted with an amine of formula R$^1$R$^2$NH in the presence of a base, for example a tertiary amine such as triethylamine and in the presence of a catalyst for example dimethylaminopyridine. Suitable solvents for the reaction include nitriles such as acetonitrile and amides such as dimethylformamide. The reaction is conveniently performed at a temperature in the range of from 0 to 120° C.

(k) A compound of formula (I) in which Y—Z is —NHC(O)— may be reacted with a reagent such as for example phosphorus pentasulphide or Lawesson's reagent (2,4-bis(4-methoxyphenyl)-1,3-dithia-2,4-diphosphetane-2,4-disulphide), optionally in the presence of a suitable base such as for example pyridine or triethylamine. Suitable solvents for the reaction include for example toluene, tetrahydrofuran, 1,3-dioxane or acetonitrile. The reaction is conveniently performed at a temperature in the range of from 0 to reflux.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

For example, it will be appreciated that certain of the optional aromatic substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by, for example, catalytic hydrogenation with a nickel catalyst or treatment with iron in the presence of hydrochloric acid with heating; oxidation of alkylthio to alkylsulphinyl or alkylsulphonyl using, for example, hydrogen peroxide in acetic acid with heating or 3-chloroperbenzoic acid.

Specific examples of the techniques used to make that starting materials described above are illustrated, but not limited by, the following examples in which variable groups are as defined for formula (I) unless otherwise stated.

1) Preparation of Compounds of Formula (II)

a) compounds of formula (II) in which Y—Z is OCH$_2$, SCH$_2$ or NHCH$_2$ may be made by treating the corresponding compound of formula (X) wherein J is —OH, —SH, —NH2 or a compound of formula (III) with a compound of formula (XII):

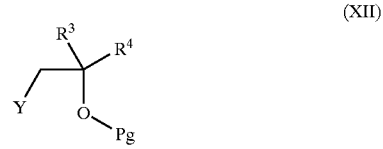

where Y is a leaving group for example mesylate; in the presence of a base such as an alkali metal hydride (e.g. sodium hydride), in a solvent such as tetrahydrofuran, N,N-dimethylformamide, dimethyl sulphoxide, or 1,3-Dimethyl-3,4,5,6tetrahydro-2(1H)pyrimidinone, and at a temperature of 20° C. to reflux.

b) A compound of formula (II), wherein Y—Z is —NHC(O)—, may be made by coupling a compound of formula (III) with a compound of formula (IV) (where G is hydroxy protected with a protecting group) in a manner analogous to that described for procedure (b) of preparations of a compound of formula (I) above.

Compounds of formula (IV) where G is hydroxy protected with a protecting group may be made by conventional procedures. For example, cleavage of the ester group of a compound of formula (XII):

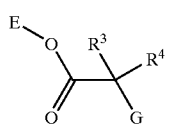

(XIII)

where E is a carboxy protecting group (e.g. Me);
under standard conditions such as mild alkaline conditions, for example, aqueous lithium hydroxide.

Compounds of formula (XIII) where G is protected hydroxy are prepared by protecting a compound of formula (XIII) where G is hydroxy by reaction with a compound such as benzyl chloride or benzyl bromide (in the presence of a suitable base such as sodium hydride and optionally with a catalyst such as sodium iodide, to provide a benzyl protecting group) or any of the conventional silylating agents known and used for such purpose (for example 2-trimethylsilylethoxymethyl chloride, in the presence of a suitable base such as triethylamine optionally in the presence of a catalyst such as dimethylaminopyridine).

Compounds of formula (XIII) where G is hydroxy are prepared by esterifying an acid of formula (IV) by a conventional esterification procedure such as reaction with a $C_{1-6}$alcohol (e.g. methanol) in the presence of an acid catalyst (for example sulphuric acid).

c) A compound of formula (II), wherein Y—Z is ethynylene, may be made by reacting a compound of formula (XIV):

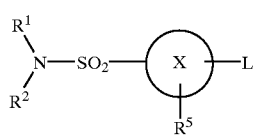

(XIV)

wherein L is a leaving group such as bromo, iodo, or triflate, with an acetylene of formula (XV)

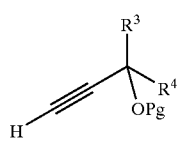

(XV)

in the presence of a catalyst such as a combination of copper (I) iodide and bis(triphenylphosphine) palladium dichloride or palladium (II) acetate. The reaction can be conducted in an inert solvent such as tetrahydrofuran, benzene, or toluene, or in a basic solvent such as diethylamine or triethylamine, and at a temperature in the range of −20 to 110° C.

A compound of formula (XV) may be made by reacting a compound of formula (XVI)

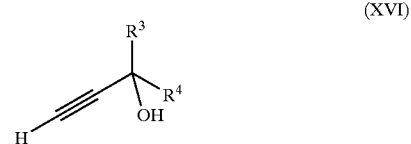

(XVI)

with an agent such as:
i) benzyl bromide (to provide a benzyl protecting group), this reaction may conveniently be conducted in the presence of a base such as sodium hydride and optionally in the presence of a catalyst such as sodium iodide in a solvent such as tetrahydrofuran at a temperature of about −78 to about 100° C.; or
ii) any of the conventional silylating agents known and used for such purpose (such as for example tert-butyl dimethylsilylchloride or triflate, in the presence of a suitable base such as 1,8-Diazabicyclo[5.4.0]undec-7-ene or triethylamine optionally in the presence of a catalyst such as dimethylaminopyridine) at a temperature of about −78 to about 100° C.

d) A compound of formula (II), wherein Y—Z is trans-vinylene, may be made by reacting a compound of formula (XVII):

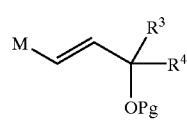

(XVII)

where M is an alkylmetal group such as a trialkyltin (for example tributyl- or trimethyl-tin) or a bisalkyloxyborane (for example catecholborane);
with a compound of formula (X), wherein J may be a leaving group for example iodide, bromide or triflate in the presence of a catalyst such as bis(triphenylphosphine)palladium dichloride or tetrakis(triphenylphosphine)palladium (0). The reaction may conveniently be conducted in a suitable inert solvent such as a tetrahydrofuran or dimethylformamide at a temperature of 0–150° C.

A compound of formula (XVII) may be made by a reaction of a compound of formula (XV)
i) with an agent such as catecholborane, to form the vinylborane compound; or
ii) a trialkyltinhydride in the presence of a catalytic amount of a radical chain initiator such as, for example, aza-bis-isobutyronitrile or by using trialkyltinhydride pre-treated with a strong base (such as an alkyllithium) and copper (I) cyanide, or by using a transition metal catalyst such as, for example, tetrakis(triphenylphosphine)palladium(0) to form a compound of formula (XVII) where M is trialkyltin.

These reactions may conveniently be conducted in a suitable inert solvent such as tetrahydrofuran, toluene or xylene at a temperature of from 0–150° C.

Compounds of formula (XVI) may be made by reacting a compound of formula (VI) with an alkali metal acetylide (for example lithium acetylide) or alkaline earth metal acetylide (for example magnesium acetylide). The reaction may be conducted in a solvent such as tetrahydrofuran, diethyl ether, or 1,2-dimethoxyethane and at a temperature of −100 to 25° C.

2) Preparation of Compounds of Formula (III)

A compound of formula (III) may be prepared:

i) from a compound of formula (XVIII)

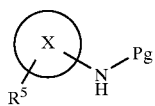

(XVIII)

wherein Pg is a protective group such as for example acetyl;
a) by treatment with chlorosulphonic acid under standard conditions, and then
b) formation of the sulphonamide under standard conditions as described above in process (j) for preparation of a compound of formula (I) and then
c) cleavage of the protecting group under mild alkaline conditions (for example when Pg is acetyl with a base such as aqueous sodium hydroxide); or ii) by reducing a compound of formula (XIX):

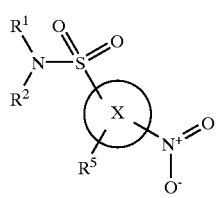

(XIX)

under standard conditions for example by a reducing agent such as tin (II) chloride or iron dust in conjunction with concentrated acid to give a compound of formula (III).

A compound of formula (XIX) may be made by reacting a compound of formula (XX):

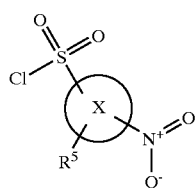

(XX)

with an amine of formula $R^1R^2NH$— in a procedure analogous to that used in process (j) for preparation of a compound of formula (I) above.

A compound of formula (XX) may be prepared:
a) by oxidising a compound of formula (XXI):

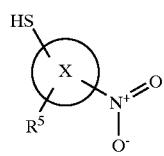

(XXI)

under standard conditions for example with chlorine in a suitable solvent such as acetic acid at a temperature of −78 to about 100° C.; or b) by diazotizing a compound of formula (XXII):

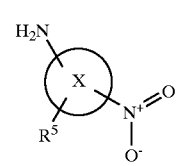

(XXII)

under standard conditions for example with nitrous acid and sulphuric acid followed by reaction with a mixture of sulphur dioxide and copper (II) chloride in a suitable solvent such as water or a water/acetic acid solution.

3) Resolution of Compounds of Formula (IV)

If the resolved acid is required it may be prepared by any of the known methods for preparation of optically-active forms (for example, by recrystallisation of the chiral salt {for example WO 9738124}, by enzymatic resolution, by biotransformation, or by chromatographic separation using a chiral stationary phase). For example if an (R)-(+) resolved acid is required it may be prepared by the method of Scheme 2 in World Patent Application Publication No. WO 9738124 for preparation of the (S)-(−) acid, i.e. using the classical resolution method described in European Patent Application Publication No. EP 0524781, also for preparation of the (S)-(−) acid, except that (1S,2R)-norephedrine may be used in place of (S)-(−)-1-phenylethylamine.

4) Preparation of Compounds of Formula (V)

A compound of formula (V) may be prepared by reacting a compound of formula (XIV), wherein L is bromo, iodo or triflate with trimethylsilylacetylene in the presence of a catalyst such as a combination of bis(triphenylphosphine) palladium dichloride and copper(I) iodide in diethylamine or triethylamine, followed by treatment with a base (for example potassium carbonate) in a $C_{1-6}$alcohol (such as methanol) as the solvent to remove the trimethylsilyl group.

5) Preparation of Compounds of Formula (VII)

A compound of formula (VII) may be prepared from a compound of formula (XXIII):

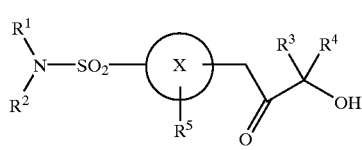

(XXIII)

by reduction under standard conditions for example by using a hydride, such as sodium borohydride.

A compound of formula (XXIII) may be prepared by deprotonation of a compound of formula (XXIV),

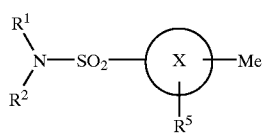

(XXIV)

with a strong base, for example lithium diisopropyl amide in an organic solvent, for example tetrahydrofuran at a temperature of −78 to 100° C. followed by addition of an amide of formula (XXV):

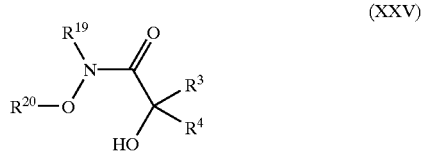

(XXV)

in which $R^{19}$ and $R^{20}$ are each independently $C_{1-6}$alkyl or together with the atoms to which they are attached form a 5–7 membered ring.

An amide of formula (XXV) may be prepared from an acid of formula (IV), or a reactive derivative thereof, by reaction with an amine of formula $R^{19}(R^{20}O)NH$ under standard conditions such as those described in process (b) for preparation of a compound of formula (I) above.

6) Preparation of Compounds of Formula (VIII)

A compound of formula (VIII) may be prepared from a diol of formula (VII) using a suitable dehydrating agent, for example bis[α,α-bis(trifluoromethyl)benzenemethanolato] diphenyl sulphur.

7) Preparation of Compounds of Formula (IX)

A compound of formula (IX) may be made by treating a compound of formula (VI) with a trimethylsulphonium salt (such as trimethylsulphonium iodide) and a base (such as an alkali metal hydroxide) in a solvent such as dichloromethane.

8) Preparation of Compounds of Formula (X)

a) A compound of formula (X) wherein J is —OH, may be prepared by diazotizing a compound of formula (III) under standard conditions such as those described above in 2(ii) above followed by heating the resulting compound in dilute sulphuric acid.
b) A compound of formula (X), wherein J is —SH, may be prepared by reacting a compound of formula (XIV) where L is a leaving group (for example chloro) with an excess of methanethiol in the presence of sodium hydride.

9) Preparation of Compounds of Formula (XI)

A compound of formula (XI) wherein K is chloro, in which Y—Z is $OCH_2$, $SCH_2$, $NHCH_2$ or —NHC(O)— may be prepared by
1) either
  a) coupling a compound of formula (XXVI)

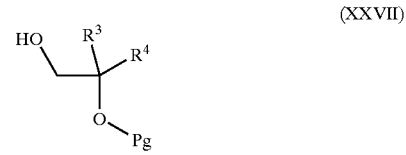

(XXVI)

wherein J is —OH, —SH or $NH_2$ with a compound of formula (XII) where Y is a leaving group for example mesylate; in the presence of a base such as an alkali metal hydride (e.g. sodium hydride), in a solvent such as tetrahydrofuran, N,N-dimethylformamide, dimethyl sulphoxide, or 1,3-Dimethyl-3,4,5,6tetrahydro-2(1H)-pyrimidinone, and at a temperature of 20° C. to reflux; or b) where Y—Z is —NHC(O)— coupling with a compound of formula (XXVI) where J is $NH_2$ with a compound of formula (IV), following a method analogous to that of process (b) for preparation of a compound of formula (I) above.

Route a or b is then followed by:
2) treatment with chlorosulphonic acid.

10) Preparation of Compounds of Formula (XII)

A compound of formula (XII), wherein Y is mesylate may be prepared by reacting a compound of formula (XXVII):

$$\underset{Pg}{\overset{HO\quad R^3\quad R^4}{\diagdown\diagup}}$$

(XXVII)

with methanesulphonicacid chloride in the presence of a base such as triethylamine, in a solvent such as dichloromethane, and at a temperature of about −78 to 25° C.

Compounds of formula (XXVII) are prepared by reducing a compound of formula (XIII) with a suitable reducing agent such as lithium aluminium hydride in a solvent such as diethyl ether or THF and at a temperature of about 0 to about 25° C.

It is noted that many of the starting materials for synthetic methods as described above are commercially available and/or widely reported in the scientific literature, or could be made from commercially available compounds using adaptations of processes reported in the scientific literature.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In cases where compounds of formula (I) are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulphonate, acetate, tartrate, citrate, succinate, benzoate, ascorbate, α-ketoglutarate, and α-glycerophosphate. Suitable inorganic salts may also be formed such as sulphate, nitrate, and hydrochloride.

Pharmaceutically acceptable salts may be obtained using standard procedures well known in the art, for example by reacting a sufficiently basic compound of formula (I) (or its ester) with a suitable acid affording a physiologically acceptable anion. It is also possible with most compounds of the invention to make a corresponding alkali metal (e.g. sodium, potassium, or lithium) or alkaline earth metal (e.g. calcium) salt by treating a compound of formula (I) (and in some cases the ester) with one equivalent of an alkali metal or alkaline earth metal hydroxide or alkoxide (e.g. the ethoxide or methoxide) in aqueous medium followed by conventional purification techniques.

In vivo cleavable esters of compounds of the invention may be made by coupling with a pharmaceutically acceptable carboxylic acid or an activated derivative thereof. For example, the coupling may be carried out by treating a compound of formula (I) with an appropriate acid chloride (for example, acetyl chloride, propionyl chloride, or benzoyl chloride) or acid anhydride (for example, acetic anhydride, propionic anhydride, or benzoic anhydride) in the presence of a suitable base such as triethylamine. Those skilled in the art will appreciate that other suitable carboxylic acids (including their activated derivatives) for the formation of in vivo cleavable esters are known to the art and these are also intended to be included within the scope of the invention. Catalysts such as 4-dimethylaminopyridine may also be usefully employed.

Many of the intermediates defined herein are novel and these are provided as a further feature of the invention.

The identification of compounds which elevate PDH activity is the subject of the present invention. These properties may be assessed, for example, using one or more of the procedures set out below:

(a) In vitro Elevation of PDH Activity

This assay determines the ability of a test compound to elevate PDH activity. cDNA encoding PDH kinase may be obtained by Polymerase Chain Reaction (PCR) and subsequent cloning. This may be expressed in a suitable expression system to obtain polypeptide with PDH kinase activity. For example rat PDHkinaseII (rPDHKII) obtained by expression of recombinant protein in *Escherichia coli* (*E. Coli*), was found to display PDH kinase activity.

In the case of the rPDHKII (Genbank accession number U10357) a 1.3 kb fragment encoding the protein was isolated by PCR from rat liver cDNA and cloned into a vector (for example pQE32—Quiagen Ltd.). The recombinant construct was transformed into *E. coli* (for example M15pRep4—Quiagen Ltd.). Recombinant clones were identified, plasmid DNA was isolated and subjected to DNA sequence analysis. One clone which had the expected nucleic acid sequence was selected for the expression work. Details of the methods for the assembly of recombinant DNA molecules and the expression of recombinant proteins in bacterial systems can be found in standard texts for example Sambrook et al, 1989, Molecular Cloning—A Laboratory Manual, $2^{nd}$ edition, Cold Spring Harbour Laboratory Press. Other known PDH kinases for use in assays, may be cloned and expressed in a similar manner.

For expression of rPDHKII activity, *E. coli* strain M15pRep4 cells were transformed with the pQE32 vector containing rPDHKII cDNA. This vector incorporates a 6-His tag onto the protein at its N-terminus. *E. coli* were grown to an optical density of 0.6 (600 nM) and protein expression was induced by the addition of 10 μM isopropylthio-β-galactosidase. Cells were grown for 18 hours at 18° C. and harvested by centrifugation. The resuspended cell paste was lysed by homogenisation and insoluble material removed by centrifugation at 24000×g for 1 hour. The 6-His tagged protein was removed from the supernatant using a nickel chelating nitrilotriacetic acid resin (Ni-NTA: Quiagen Ltd.) matrix (Quiagen) which was washed with 20 mM tris(hydroxymethyl)aminomethane-hydrogen chloride, 20 mM imidazole, 0.5 M sodium chloride pH 8.0, prior to elution of bound protein using a buffer containing 20 mM tris(hydroxymethyl)aminomethane-hydrogen chloride, 200 mM imidazole, 0.15 M sodium chloride pH 8.0. Eluted fractions containing 6-His protein were pooled and stored in aliquots at −80° C. in 10% glycerol.

Each new batch of stock enzyme was titrated in the assay to determine a concentration giving approximately 90% inhibition of PDH in the conditions of the assay. For a typical batch, stock enzyme was diluted to 7.5 μg/ml.

For assay of the activity of novel compounds, compounds were diluted with 10% dimethylsulphoxide (DMSO) and 10 μl transferred to individual wells of 96-well assay plates. Control wells contained 20 μl 10% DMSO instead of compound. 40 μl Buffer containing 50 mM potassium phosphate buffer pH 7.0, 10 mM ethylene glycol-bis(β-aminoethyl ether)-N,N,N,N-tetracetic acid (EGTA), 1 mM benzamidine, 1 mM phenylmethylsulphonyl fluoride (PMSF), 0.3 mM tosyl-L-lysine chloromethyl ketone (TLCK), 2 mM dithiothreitol (DTT), recombinant rPDHKII and compounds were incubated in the presence of PDH kinase at room temperature for 45 minutes. In order to determine the maximum rate of the PDH reaction a second series of control wells were included containing 10% DMSO instead of compound and omitting rPDHKII. PDH kinase activity was then initiated by the addition of 5 μM ATP, 2 mM magnesium chloride and 0.04 U/ml PDH (porcine heart PDH Sigma P7032) in a total volume of 50 μl and plates incubated at ambient temperature for a further 45 minutes. The residual activity of the PDH was then determined by the addition of substrates (2.5 mM coenzyme A, 2.5 mM thiamine pyrophosphate (cocarboxylase), 2.5 mM sodium pyruvate, 6 mM NAD in a total volume of 80 μl and the plates incubated for 90 minutes at ambient temperature. The production of reduced NAD (NADH) was established by measured optical density at 340 nm using a plate reading spectrophotometer. The $ED_{50}$ for a test compound was determined in the usual way using results from 12 concentrations of the compound.

(b) In vitro Elevation of PDH Activity in Isolated Primary Cells

This assay determines the ability of compounds to stimulate pyruvate oxidation in primary rat hepatocytes.

Hepatocytes were isolated by the two-step collagenase digestion procedure described by Seglen (Methods Cell Biol. (1976) 13, 29–33) and plated out in 6-well culture plates (Falcon Primaria) at 600000 viable cells per well in Dulbecco's Modified Eagles Medium (DMEM, Gibco BRL) containing 10% foetal calf serum (FCS), 10% penicillin/streptomycin (Gibco BRL) and 10% non-essential amino acids (NEAA, Gibco BRL). After 4 hours incubation at 37° C. in 5% $CO_2$, the medium was replaced with Minimum Essential Medium (MEM, Gibco BRL) containing NEAA and penicillin/streptomycin as above in addition to 10 nM dexanethasone and 10 nM insulin.

The following day cells were washed with phosphate buffered saline (PBS) and medium replaced with 1 ml HEPES-buffered Krebs solution (25 mM HEPES, 0.1 SM sodium chloride, 25 mM sodium hydrogen carbonate, 5 mM potassium chloride, 2 mM calcium chloride, 1 mM magnesium sulphate, 1 mM potassium dihydrogen phosphate) containing the compound to be tested at the required concentration in 0.1% DMSO. Control wells contained 0.1% DMSO only and a maximum response was determined using a 10 μM treatment of a known active compound. After a preincubation period of 40 minutes at 37° C. in 5% $CO_2$, cells were pulsed with sodium pyruvate to a final concentration of 0.5 mM (containing 1-$^{4}$C sodium pyruvate (Amersham product CFA85) 0.18 Ci/mmole) for 12 minutes. The medium was then removed and transferred to a tube which was immediately sealed with a bung containing a suspended centre well. Absorbent within the centre well was saturated with 50% phenylethylamine, and $CO_2$ in the medium released by the addition of 0.2 μl 60% (w/v) perchloric acid (PCA). Released $^{14}CO_2$ trapped in the absorbent was determined by liquid scintillation counting. The $ED_{50}$ for a test compound was determined in the usual way using results from 7 concentrations of the compound.

(c) In vivo Elevation of PDH Activity

The capacity of compounds to increase the activity of PDH in relevant tissues of rats may be measured using the test described hereinafter. Typically an increase in the proportion of PDH in its active, nonphosphorylated form may be detected in muscle, heart, liver and adipose tissue after a single administration of an active compound. This may be expected to lead to a decrease in blood glucose after repeated administration of the compound. For example a single administration of DCA, a compound known to activate PDH by inhibition of PDH kinase (Whitehouse, Cooper and Randle (1974) Biochem. J. 141, 761–774) 150 mg/kg, intraperitoneally, increased the proportion of PDH in its active form (Vary et al. (1988) Circ. Shock 24, 3–18) and after repeated administration resulted in a significant decrease in plasma glucose (Evans and Stacpoole (1982) Biochem. Pharmacol. 31, 1295–1300).

Groups of rats (weight range 140–180 g) are treated with a single dose or multiple doses of the compound of interest by oral gavage in an appropriate vehicle. A control group of rats is treated with vehicle only. At a fixed time after the final administration of compound, animals are terminally anaesthetised, tissues are removed and frozen in liquid nitrogen. For determination of PDH activity, muscle samples are disrupted under liquid nitrogen prior to homogenisation by one thirty-second burst in a Polytron homogenizer in 4 volumes of a buffer containing 40 mM potassium phosphate pH 7.0, 5 mM EDTA, 2 mM DTT, 1% Triton X-100, 10 mM sodium pyruvate, 10 μM phenylmethylsulphonyl chloride (PMSF) and 2 μg/ml each of leupeptin, pepstain A and aprotinin. Extracts are centrifuged before assay. A portion of the extract is treated with PDH phosphatase prepared from pig hearts by the method of Siess and Wieland (Eur. J. Biochem (1972) 26, 96): 20 μl extract, 40 μl phosphatase (1:20 dilution), in a final volume of 125 μl containing 25 mM magnesium chloride, 1 mM calcium chloride. The activity of the untreated sample is compared with the activity of the dephosphorylated extract thus prepared PDH activity is assayed by the method of Stansbie et al., (Biochem. J. (1976) 154, 225). 50 μl Extract is incubated with 0.75 mM NAD, 0.2 mM CoA, 1.5 mM thiamine pyrophosphate (TPP) and 1.5 mM sodium pyruvate in the presence of 20 μg/ml p-(p-amino-phenylazo) benzene sulphonic acid (AABS) and 50 mU/ml arylamine transferase (AAT) in a buffer containing 100 mM tris(hydroxymethyl)aminomethane, 0.5 mM EDTA, 50 mM sodium fluoride, 5 mM 2-mercaptoethanol and 1 mM magnesium chloride pH 7.8. AAT is prepared from pigeon livers by the method of Tabor et al. (J. Biol. Chem. (1953) 204, 127). The rate of acetyl CoA formation is determined by the rate of reduction of AABS which is indicated by a decrease in optical density at 460 nm.

Liver samples are prepared by an essentially similar method, except that sodium pyruvate is excluded from the extraction buffer and added to the phosphatase incubation to a final concentration of 5 mM.

Treatment of an animal with an active compound results in an increase in the activity of PDH complex in tissues. This is indicated by an increase in the amount of active PDH (determined by the activity of untreated extract as a percentage of the total PDH activity in the same extract after treatment with phosphatase).

According to a further aspect of the invention there is provided a pharmaceutical composition which comprises a compound of the formula (I) as defined hereinbefore or a pharmaceutically acceptable salt or an in vivo hydrolysable ester thereof, in association with a pharmaceutically acceptable excipient or carrier.

According to a further aspect of the invention there is provided a pharmaceutical composition which comprises a compound of the formula (I) which is selected from:

i) a compound of the formula (I) wherein $R^3$ and $R^4$ are both methyl, $R^5$ is hydrogen, fluoro or chloro, Y—Z is ethynylene, X is phenyl and one of $R^1$ and $R^2$ is hydrogen and the other is pyrimidyl-NH—C(O)— or triazinyl-NH—C(O)— (wherein said triazine or pyrimidine is substituted by methyl, methoxy or dimethylamino) and the —$SO_2NR^1R^2$ moiety is ortho to Y—Z;

ii) 4-(3-hydroxy-3-methyl-1-butynyl)-N-(3-methyl-2-pyridinyl)-benzenesulphonamide;

iii) N-{4-[N,N-bis-(sec-butyl)aminosulphonyl]phenyl}-2-hydroxy-2-methyl-3,3,3-trifluoropropanamide; or iv) N-{4-[N,N-bis-(iso-butyl)aminosulphonyl]phenyl}-2-hydroxy-2-methyl-3,3,3-trifluoropropanamide;

or a pharmaceutically acceptable salt or an in vivo hydrolysable ester thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula (I) or a pharmaceutically acceptable salt or an in vivo hydrolysable ester thereof as defined hereinbefore for use in a method of treatment of the human or animal body by therapy.

We have found that compounds of the present invention elevate PDH activity and are therefore of interest for their blood glucose-lowering effects.

A further feature of the present invention is a compound of formula (I) and pharmaceutically acceptable salts or in vivo hydrolysable esters thereof for use as a medicament.

Conveniently this is a compound of formula (I), or a pharmaceutically acceptable salt or an in vivo hydrolysable ester thereof, for use as a medicament for producing an elevation of PDH activity in a warm-blooded animal such as a human being.

Thus according to a further aspect of the invention there is provided the use of a compound of the formula (I), or a pharmaceutically acceptable salt or an in vivo hydrolysable ester thereof in the manufacture of a medicament for use in the production of an elevation of PDH activity in a warm-blooded animal such as a human being.

According to a further feature of the invention there is provided a method for producing an elevation of PDH activity in a warm-blooded animal, such as a human being, in need of such treatment which comprises administering to said animal an effective amount of a compound of formula (I) or a pharmaceutically acceptable salt or an in vivo-hydrolysable ester thereof as defined hereinbefore.

For the avoidance of doubt, in aspects of the invention concerning the use of compounds of formula (I) or pharmaceutically acceptable salts or in vivo hydrolysable esters thereof in medicine, the definition of compounds includes compounds selected from:
  i) a compound of the formula (I) wherein $R^3$ and $R^1$ are both methyl, $R^5$ is hydrogen, fluoro or chloro, Y—Z is ethynylene, X is phenyl and one of $R^1$ and $R^2$ is hydrogen and the other is pyrimidyl-NH—C(O)— or triazinyl-NH—C(O)— (wherein said triazine or pyrimidine is substituted by methyl, methoxy or dimethylamino) and the —$SO_2NR^1R^2$ moiety is ortho to Y—Z;
  ii) 4-(3-hydroxy-3-methyl-1-butynyl)-N-(3-methyl-2-pyridinyl)-benzenesulphonamide;
  iii) N-{4-[N,N-bis-(sec-butyl)aminosulphonyl]phenyl}-2-hydroxy-2-methyl-3,3,3-trifluoropropanamide; or
  iv) N-{4-[N,N-bis-(iso-butyl)aminosulphonyl]phenyl}-2-hydroxy-2-methyl-3,3,3-trifluoropropanamide;
and their pharmaceutically acceptable salts and in vivo hydrolysable esters.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The elevation of PDH activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. For example in the treatment of diabetes mellitus chemotherapy may include the following main categories of treatment:
  i) insulin;
  ii) insulin secretagogue agents designed to stimulate insulin secretion (for example glibenclamide, tolbutamide, other sulphonylureas);
  iii) oral hypoglycaemic agents such as metformin, thiazolidinediones;
  iv) agents designed to reduce the absorption of glucose from the intestine (for example acarbose);
  v) agents designed to treat complications of prolonged hyperglycaemia;
  vi) other agents used to treat lactic acidaemia;
  vii) inhibitors of fatty acid oxidation;
  viii) lipid lowering agents;
  ix) agents used to treat coronary heart disease and peripheral vascular disease such as aspirin, pentoxifylline, cilostazol; and/or
  x) thiamine.

As stated above the compounds defined in the present invention are of interest for their ability to elevate the activity of PDH. Such compounds of the invention may therefore be useful in a range of disease states including diabetes mellitus, peripheral vascular disease, (including intermittent claudication), cardiac failure and certain cardiac myopathies, myocardial ischaemia, cerebral ischaemia and reperfusion, muscle weakness, hyperlipidaemias, Alzheimers disease and/or atherosclerosis.

In addition to their use in therapeutic medicine, the compounds of formula (I) and their pharmaceutically acceptable salts are also useful as pharmacological tools in the development and standardisation of in vitro and in vivo test systems for the evaluation of the effects of elevators of PDH activity in laboratory animals such as cats, dogs, rabbits, monkeys, rats and mice, as part of the search for new therapeutic agents.

The invention will now be illustrated by the following non-limiting examples in which, unless stated otherwise:
  (i) temperatures are given in degrees Celsius (° C.); operations were carried out at room or ambient temperature, that is, at a temperature in the range of 18–25° C.;
  (ii) organic solutions were dried over anhydrous magnesium sulphate; evaporation of solvent was carried out using a rotary evaporator under reduced pressure (600–4000 Pascals; 4.5–30 mm Hg) with a bath temperature of up to 60° C.;

(iii) chromatography unless otherwise stated means flash chromatography on silica gel; thin layer chromatography (TLC) was carried out on silica gel plates; where a "Bond Elut" column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI"

(iv) in general, the course of reactions was followed by TLC and reaction times are given for illustration only;

(v) yields are given for illustration only and are not necessarily those which can be obtained by diligent process development; preparations were repeated if more material was required;

(vi) when given, $^1$H NMR data is quoted and is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as the solvent unless otherwise stated; coupling constants (J) are given in Hz;

(vii) chemical symbols have their usual meanings; SI units and symbols are used;

(viii) solvent ratios are given in percentage by volume;

(ix) mass spectra (MS) were run with an electron energy of 70 electron volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the negative mass ion —(M—H)—; and (x) the following abbreviations are used:

| | |
|---|---|
| DMSO | dimethyl sulphoxide; |
| DMF | N,N dimethylformamide; |
| DCM | dichloromethane; and |
| EtOAc | ethyl acetate. |

EXAMPLE 1

N-[2-Chloro-4-(morpholinosulphonyl)phenyl]-2-hydroxy-2-methylpropanamide

2-Acetoxyisobutyryl chloride (660 mg, 3.6 mmol) was added to a stirred mixture of 2-chloro-4-(morpholinosulphonyl)anilino (Method A) (1.0 g, 3.6 mmol) and pyridine (0.34 ml, 4.2 mmol) in DCM (10 ml). The resultant mixture was stirred at ambient temperature overnight, then washed with 1M aqueous hydrochloric acid and brine, dried and evaporated to dryness. The residue was dissolved in 1% aqueous ethanol (10 ml) and lithium hydroxide monohydrate was added (300 mg, 7.5 mmol). The mixture was stirred for 2h at ambient temperature, then EtOAc (25 ml) was added and the resulting organic layer was washed with water, dried and evaporated to dryness to yield the title compound (226 mg, 0.6 mmol). NMR: 1.4 (s, 6H), 2.9 (m, 4H), 3.6 (m, 4H), 6.3 (s, 1H), 7.7 (d, 1H), 7.8 (m, 1H), 8.6 (d, 1H), 9.8 (s, 1H); MS: 363 (M+H)$^+$.

EXAMPLE 2

N-[2-Chloro-4-(piperidinosulphonyl)phenyl]-2-hydroxy-2-methylpropanamide

A solution of N-[2-chloro-4-(fluorosulphonyl)phenyl]-2-acetoxy-2-methylpropanamide (Method B) (340 mg, 1 mmol), 4-dimethylaminopyridine (10 mg, 0.08 mmol) and piperidine (0.1 ml, 1 mmol) in acetonitrile (5 ml) was heated under reflux for 18 h. After evaporation to dryness, the residue was dissolved in 1% aqueous ethanol (10 ml) and lithium hydroxide monohydrate (84 mg, 2 mmol) was added. The mixture was stirred for 2 h at ambient temperature, then EtOAc (25 ml) was added. The resulting solution was washed with water, dried and evaporated to dryness. The residue was purified by column chromatography using 50% EtOAc/isohexane to yield the title compound as an oil (226 mg, 0.6 mmol). NMR: 1.4 (s, 6H), 1.5 (m, 6H), 2.9 (m, 4H), 6.2 (d, 1H), 7.7 (d, 1H), 7.8 (m, 1H), 8.6 (d, 1H), 9.8 (s, 1H); MS: 361 (M+H)$^+$.

EXAMPLES 3–21

The procedures described in Examples 1 and 2 were repeated using the appropriate amine to replace the morpholine or piperidine to obtain the compounds described below in yields of 30–65%. "Meth" refers to whether the Example was made by the procedure of Example 1 or 2.

| Ex | Compound | MS | NMR | Meth |
|---|---|---|---|---|
| 3 | N-[2-Chloro-4-(methylaminosulphonyl)phenyl]-2-hydroxy-2-methylpropanamide | 305 | 1.4(s,6H), 2.5(d,3H), 6.2(s,1H), 7.3 (m,1H), 7.7(m,1H), 7.8(d,1H), 8.5(d, 1H), 9.7(s,1H). | 1 |
| 4 | N-[2-Chloro-4-(dimethylaminosulphonyl)phenyl]-2-hydroxy-2-methylpropanamide | 319 | 1.4(s,6H), 2.6(m,6H), 6.2(s,1H), 7.7 (m,1H), 7.8(d,1H), 8.6(d,1H), 9.8(s, 1H). | 1 |
| 5 | N-[2-Chloro-4-(allylaminosulphonyl)phenyl]-2-hydroxy-2-methylpropanamide | 331 | 1.4(s,6H), 3.2(m,2H), 5.1(m,2H), 5.6(m,1H), 6.2(br,1H), 7.7(m,1H), 7.8(m,1H), 7.85(1H,m), 8.5(d,1H), 9.7(s,1H). | 2 |
| 6 | N-[2-Chloro-4-(isopropylaminosulphonyl)phenyl]-2-hydroxy-2-methylpropanamide | 333 | 0.9(d,6H), 1.4(s,6H), 2.7(m,1H), 6.2 (s,1H), 7.6(m,1H), 7.8(m,1H), 7.9(d, 1H), 8.6(d,1H), 9.8(s,1H). | 2 |
| 7 | N-[2-Chloro-4-(n-butylaminosulphonyl)phenyl]-2-hydroxy-2-methylpropanamide phenyl]-2- | 347 | 0.8(m,3H), 1.2(m,4H), 1.4(s,6H), 2.7(m,2H), 6.2(s,1H), 7.6(m,1H), 7.8(m,1H), 7.9(d,1H), 8.6(d,1H), 9.8 (s,1H). | 2 |

-continued

| Ex | Compound | MS | NMR | Meth |
|---|---|---|---|---|
| 8 | N-[2-Chloro-4-(t-butylamino-sulphonyl)phenyl]-2-hydroxy-2-methylpropanamide | 347 | 1.0(s,9H), 1.4(s,6H), 6.2(s,1H), 7.6 (m,1H), 7.8(m,1H), 7.9(d,1H), 8.6(d,1H), 9.8(s,1H). | 2 |
| 9 | N-[2-Chloro-4-(n-pentyl-aminosulphonyl)phenyl]-2-hydroxy-2-methylpropanamide | 361 | 0.8(m,3H), 1.2(m,6H), 1.4(s,6H), 2.7(m,2H), 6.2(s,1H), 7.6(m,1H), 7.8(m,1H), 7.9(d,1H), 8.5(d,1H), 9.8(s,1H). | 2 |
| 10 | N-[2-Chloro-4-(cyclohexyl-aminosulphonyl]phenyl]-2-hydroxy-2-methylpropanamide | 373 | 1.0–1.2(m,10H), 1.4(s,6H), 2.7(m,1H), 6.2(s,1H), 7.6(m,1H), 7.8(m,1H), 7.9(d,1H), 8.5(d,1H), 9.8(s,1H). | 2 |
| 11 | N-[2-Chloro-4-benzylamino-sulphonyl)phenyl]-2-hydroxy-2-methylpropanamide | 381 | 1.4(s,6H), 4.0(s,2H), 6.2(br,1H), 7.2 (m,5H), 7.7(m,1H), 7.8(m,1H), 8.2 (br,1H), 8.4(d,1H), 9.7(s,1H) | 2 |
| 12 | N-[2-Chloro-4-(pyrid-3-yl-methylaminosulphonyl)phenyl]-2-hydroxy-2-methylpropanamide | 382 | 1.4(s,6H), 3.9(m,1H), 4.0(d,2H), 6.2 (s,1H), 7.3(br,1H), 7.4(m,1H), 7.6(d,1H), 7.8(m,1H), 8.3(m,1H), 8.4(m,2H), 9.7(m,1H) | 1 |
| 13 | N-(2-Chloro-4-anilino-sulphonylphenyl]-2-hydroxy-2-methylpropanamide | 367 | 1.4(s,6H), 6.2(s,1H), 7.0(m,3H), 7.2 (m,3H), 7.7(q,1H), 7.8(d,1H), 8.4(d,1H), 9.7(s,1H). | 1 |
| 14 | N-[2-Chloro-4-(2-chloroanilino-sulphonyl)phenyl]-2-hydroxy-2-methylpropanamide | 401 | 1.4(s,6H), 6.2(s,1H), 7.2(m,3H), 7.4 (m,2H), 7.6(q,1H), 7.8(d,1H), 8.4(d,1H), 9.8(s,1H). | 1 |
| 15 | N-[2-Chloro-4(3-iodoanilino-sulphonyl)phenyl]-2-hydroxy-2-methylpropanamide | 493 | 1.4(s,6H), 6.2(s,1H), 7.1(m,2H), 7.4 (m,3H), 7.7(q,1H), 7.8(s,1H), 8.4(d,1H), 9.8(s,1H). | 1 |
| 16 | N-[2-Chloro-4-(4-chloroanilino-sulphonyl)phenyl]-2-hydroxy-2-methylpropanamide | 401 | 1.4(s,6H), 6.2(s,1H), 7.1(d,2H), 7.3 (d,2H), 7.7(m,2H), 7.8(d,1H), 8.4(d,1H), 9.7(s,1H). | 1 |
| 17 | N-[2-Chloro-4-(4-methoxy-anilinosulphonyl)phenyl]-2-hydroxy-2-methylpropanamide | 397 | 1.4(s,6H), 3.6(s,3H), 6.2(br,1H), 6.8 (d,2H), 7.0(d,2H), 7.6(m,2H), 7.7(d,1H), 8.4(d,1H), 9.7(s,1H). | 1 |
| 18 | N-[2-Chloro-4-(2-chloro-4-iodoanilinosulphonyl)phenyl]-2-hydroxy-2-methylpropanamide | 527 | 1.4(s,6H), 6.3(s,1H), 7.0(d,1H), 7.6 (m,3H), 7.8(d,2H), 8.4(d,1H), 9.8(s,1H). | 1 |
| 19 | N-[2-Chloro-4-(2-fluoro-4-iodoanilinosulphonyl)phenyl]-2-hydroxy-2-methylpropanamide | 511 | 1.4(s,6H), 6.3(s,1H), 7.0(m,1H), 7.5 (m,1H), 7.6(m,2H), 7.8(m,2H), 8.5 (m,1H), 9.8(s,1H). | 1 |
| 20 | N-[2-Chloro-4-(2,4-dibromo-anilinosulphonyl)phenyl]-2-hydroxy-2-methylpropanamide | 523/525 | 1.4(s,6H), 6.2(s,1H), 7.6(m,3H), 7.8 (m,2H), 8.2(d,2H), 9.6(s,1H). | 1 |
| 21 | N-[2-Chloro-4-(3-bromo-4-chloroanilinosulphonyl)phenyl]-2-hydroxy-2-methylpropanamide | 479/481 | 1.4(s,6H), 6.2(s,1H), 7.1(m,1H), 7.5 (m,3H), 7.8(m,2H), 8.3(m,1H), 9.8 (m,1H) | 1 |

EXAMPLE 22

R/S-N-2-Chloro-4-(3-bromo-4-chloroanilinosulphonyl)phenyl]-3,3,3-trifluoro-2-hydroxy-2-methylpropanamide A solution of R/S-3,3,3-trifluoro-2-hydroxy-2-methylpropanoylchloride (Method E1) (110 mg, 0.62 mmol) in DCM (5 ml) was added to a stirred mixture of 2-chloro-4-(3-bromo-4-chloroanilinosulphonyl)aniline (Method C) (270 mg, 0.68 mmol) in DCM (10 ml). The resultant mixture was stirred at ambient temperature overnight and then washed with aqueous sodium hydrogen carbonate solution and water, dried and evaporated to dryness. The residue was purified by column chromatography using 50% EtOAc/isohexane to yield the title compound as a foam (100 mg, 0.19 mmol). NMR: 1.9 (s, 3H), 6.2 (s, 1H), 7.1 (m, 1H), 7.5 (m, 3H), 7.8 (m, 2H), 8.4 (d, 1H), 9.6 (s, 1H); MS: 533/535.

EXAMPLE 23

R-N-[2-Chloro-4-(4-methoxyanilinosulphonyl) phenyl]-3.3.3-trifluoro-2-hydroxy-2-methylpropanamide A solution of S-3,3,3-trifluoro-2-hydroxy-2-methylpropanoylchloride (Method P) (446 mg, 2.5 mmol) in DCM (15 ml) was added to a stirred mixture of 2-chloro-4 (4-methoxyanilino-sulphonyl)aniline (Method D) (650 mg, 2.1 mmol) and 2,6-di-t-butylpyridine (0.56 ml, 2.5 mmol) in DCM (50 ml). The resultant mixture was stirred at ambient temperature overnight and then washed with 1M aqueous hydrochloric acid, aqueous sodium hydrogen carbonate solution and brine, dried and evaporated to dryness. The residue was purified by column chromatography using 5% EtOAc in DCM to yield the title compound as a foam (680 mg, 1.5 mmol). EA: found: C, 45.1; H, 3.8; N, 5.8%; $C_{17}H_{16}N_2F_3ClSO_5$ requires: C, 45.1; H, 3.5; N, 6.2%; NMR ($CDCl_3$): 1.9 (s, 3H), 3.75 (s, 3H), 3.8 (s, 1H), 6.4 (s, 1H), 6.8 (d, 2H), 7.0 (d, 2H), 7.6 (dd, 1H), 7.8 (d, 1H), 8.5 (d, 1H), 9.3 (s, 1H); MS: 451.

EXAMPLES 24–105

The procedure described in Example 23 was repeated using the appropriate 4-aminobenzenesulphonamide to replace the 2-chloro-4-[(4-methoxyanilino)sulphonyl] aniline to obtain the compounds described below. "Meth" refers to the Method (see section on Starting Materials below) used to make said appropriate sulphonamide.

| Ex | Compound | MS | NMR | Meth |
|---|---|---|---|---|
| 24 | R-N-[2-Chloro-4-(allylamino-sulphonyl)phenyl]-3,3,3-trifluoro-2-hydroxy-2-methylpropanamide | 385 | (CDCl$_3$): 1.8(s,3H), 3.6(m,2H), 3.7 (s,1H), 4.6(t,1H), 5.2–5.5(m,2H), 5.7–5.8(m,1H), 7.8(dd,1H), 7.9(d, 1H), 8.6(d,1H), 9.3(s,1H) | E |
| 25 | R-N-[2-Chloro-4-(thien-2-yl-methylaminosulphonyl)phenyl]-3,3,3-trifluoro-2-hydroxy-2-methyl-propanamide* | 441 | 1.6(s,3H), 4.2(d,2H), 6.9(m,1H), 7.1(m,1H), 7.4(m,1H), 7.7(d,1H), 7.9(s,1H), 8.0(s,1H), 8.2(d,1H), 8.4 (m,1H), 9.8(s,1H) | F |
| 26 | R-N-[2-Chloro-4-(2-chloro-anilinosulphonyl)phenyl]-3,3,3-trifluoro-2-hydroxy-2-methylpropanamide | 455 | (CDCl$_3$): 1.8(s,3H), 3.65(s,1H), 7.0 (s,1H), 7.1(m,1H), 7.3(m,2H), 7.6 (d,2H), 7.8(d,1H), 8.5(d,1H), 9.3(s, 1H). | D |
| 27 | R-N-[2-Chloro-4-(methylamino-sulphonyl)phenyl]-3,3,3-trifluoro-2-hydroxy-2-methylpropanamide | 359 | (CDCl$_3$): 1.8(s,3H), 2.7(d,3H), 3.6 (s,1H), 4.4(m,1H), 7.8(dd,1H), 7.9 (d,1H), 8.6(d,1H), 9.3(s,1H). | E |
| 28 | R-N-[2-Chloro-4-(dimethyl-aminosulphonyl)phenyl]-3,3,3-trifluoro-2-hydroxy-2-methylpropanamide | 373 | (CDCl$_3$): 1.8(s,3H), 2.7(s,6H), 3.8(s, 1H), 7.7(dd,1H), 7.9(d,1H), 8.6(d, 1H), 9.3(s,1H). | E |
| 29 | R-N-[2-Chloro-4-(morpholino-sulphonyl)phenyl]-3,3,3-trifluoro-2-hydroxy-2-methylpropanamide | 415 | (CDCl$_3$): 1.8(s,3H), 3.0(m,4H), 3.6 (s,1H), 3.8(m,4H), 7.7(dd,1H), 7.9 (d,1H), 8.6(d,1H), 9.3(s,1H). | E |
| 30 | R-N-[2-Chloro-4-(diethylamino-sulphonyl)phenyl]-3,3,3-trifluoro-2-hydroxy-2-methylpropanamide | 401 | (CDCl$_3$): 1.2(t,6H), 1.8(s,3H), 3.2(q, 4H), 3.8(s,1H), 7.7(dd,1H), 7.9(d, 1H), 8.6(d,1H), 9.3(s,1H). | E |
| 31 | R-N-[2-Chloro-4-(4-t-butyl-anilinosulphonyl)phenyl]-3,3,3-trifluoro-2-hydroxy-2-methyl-propanamide* | 477 | 1.1(s,9H), 1.6(s,3H), 7.0(d,2H), 7.3 (d,2H), 7.7(dd,1H), 7.9(s,1H), 8.2(d, 1H), 9.8(s,1H). | F |
| 32 | R-N-[2-Chloro-4-(anilino sulphonyl)phenyl]-3,3,3-trifluoro-2-hydroxy-2-methylpropanamide* | 421 | 1.6(s,3H), 7.0(m,2H), 7.2(m,3H), 7.7(m,1H), 7.9(m,1H), 8.2(d,1H), 9.8(s,1H). | F |
| 33 | R-N-[2-Chloro-4-(4-fluoro-anilinosulphonyl)phenyl]-3,3,3-trifluoro-2-hydroxy-2-methyl-propanamide* | 439 | 1.6(s,3H), 7.1(m,4H), 7.7(m,1H), 7.9(s,1H); 8.2(d,1H), 9.8(d,1H). | F |
| 34 | R-N-[2-Chloro-4-(4-acetamido-anilinosulphonyl)phenyl]-3,3,3 trifluoro-2-hydroxy-2-methyl-propanamide* | 478 | 1.6(s,3H), 2.0(s,3H), 7.0(m,2H), 7.4(m,2H), 7.7(m,1H), 7.9(s,1H), 8.2(d,1H), 9.8(d,1H). | F |
| 35 | R-N-[2-Chloro-4-(4-mesylanilino sulphonyl)phenyl]-3,3,3-trifluoro-2-hydroxy-2-methyl propanamide* | 499 | 1.6(s,3H), 3.1(s,3H), 7.3(d,2H), 7.8 (d,2H), 7.85(dd,1H), 7.95(d,1H), 8.2 (d,1H). | F |
| 36 | R-N-[2-Chloro-4-(4-sulphamoyl-anilinosulphonyl)phenyl]-3,3,3-trifluoro-2-hydroxy-2-methyl propanamide* | 500 | 1.6(s,3H), 7.2(s,2H), 7.3(d,2H), 7.7 (d,2H), 7.8(dd,1H), 7.95(d,1H), 8.2 (d,1H). | F |
| 37 | R-N-[2-Chloro-4-(3-iodoanilino-sulphonyl)phenyl]-3,3,3-trifluoro 2-hydroxy-2-methylpropanamide* | 547 | 1.6(s,3H), 7.0(m,2H), 7.4(m,2H), 7.7(m,1H), 7.9(s,1H), 8.2(d,1H), 9.8(s,1H). | F |
| 38 | R-N-[2-Chloro-4-(4-methylthio-anilinosulphonyl)phenyl]-3,3,3-trifluoro-2-hydroxy-2-methyl-propanamide | 467 | 1.6(s,3H), 2.4(s,3H), 7.0(d,2H), 7.2 (d,2H), 7.7(dd,1H), 7.8(d,1H), 8.2 (d,1H). | D |
| 39 | R-N-[2-Chloro-4-(4-benzyloxy-anilinosulphonyl)phenyl]-3,3,3-trifluoro-2-hydroxy-2-methyl-propanamide | 527 | 1.6(s,3H), 5.0(s,2H), 6.85(d,2H), 7.0(d,2H), 7.4(m,5H), 7.6(dd,1H), 7.8(d,1H), 8.5(d,1H). | D |
| 40 | R-N-2-Chloro-4-sulphamoyl-phenyl)-3,3,3-trifluoro-2-hydroxy-2-methylpropanamide | 345 | 1.6(s,3H), 7.4(s,2H), 7.8(dd,1H), 7.9(d,1H), 8.2(d,1H). | D |
| 41 | R-N-{2-Chloro-4-[N,N-bis-(2-hydroxyethyl)aminosulphonyl] phenyl}-3,3,3-trifluoro-2-hydroxy-2-methyl-propanamide | 433 | 1.6(s,3H), 3.2(t,4H), 3.5(m,4H), 4.8 (t,2H), 7.8(dd,1H), 7.9(d,1H), 825 (d,1H). | D |
| 42 | R-N-(2-Chloro-4-{4-[N,N-bis-(2-hydroxyethyl)aminosulphonyl] anilinosulphonyl}phenyl)-3,3,3-trifluoro-2-hydroxy-2-methyl-propanamide | 588 | 1.6(s,3H), 3.1(t,4H), 3.5(m,4H), 4.8 (t,2H), 7.25(d,2H), 7.7(d,2H), 7.8 (dd,1H), 7.9(d,1H), 8.2(d,1H). | D |
| 43 | R-N-{2-Chloro-4-[4-(morpholino-sulphonyl)anilinosulphonyl]phenyl}-3,3,3-trifluoro-2-hydroxy-2-methylpropanamide | 570 | 1.6(s,3H), 2.95(m,4H), 3.75(m,4H), 7.2(d,2H), 7.7(d,2H), 7.8(dd,1H), 7.9(d,1H), 8.6(d,1H). | D# |

-continued

| Ex | Compound | MS | NMR | Meth |
|---|---|---|---|---|
| 44 | R-N-[2-Chloro-4-(R,S-2,3-dihydroxy-propylaminosulphonyl)phenyl]-3,3,3-trifluoro-2-hydroxy-2-methylpropanamide | 419 | 1.6(s,3H), 2.6(m,1H), 2.9(m,1H), 3.2(m,2H), 3.5(m,1H), 4.5(t,1H), 4.75(d,1H), 7.8(dd,1H), 7.9(d,1H), 8.2(d,1H). | D |
| 45 | R-N-[2-Fluoro-4-2-fluoro-anilinosulphonyl)phenyl]-3,3,3-trifluoro-2-hydroxy-2-methyl-propanamide† | 423 | CDCl$_3$: 1.75(s,3H), 6.75(s,1H), 6.9–7.0(m,1H), 7.1–7.2(m,2H), 7.5–7.6(m,3H), 8.5(t,1H), 8.9(s,1H). | G |
| 46 | R-N-[2-Fluoro-4-(2-methoxy-anilinosulphonyl)phenyl]-3,3,3-trifluoro-2-hydroxy-2-methyl-propanamide† | 435 | CDCl$_3$: 1.75(s,3H), 3.7(s,3H), 6.8(d, 1H), 6.9(t,1H), 7.0(s,1H), 7.05(t, 1H), 7.5–7.6(m,3H), 8.5(t,1H), 8.8 (s,1H). | G |
| 47 | R-N-[2-Fluoro-4-(2-methylthio-anilinosulphonyl)phenyl]-3,3,3-trifluoro-2-hydroxy-2-methyl-propanamide† | 451 | CDCl$_3$: 1.75(s,3H), 2.25(s,3H), 3.4 (s,1H), 7.1(t,1H), 7.25(t,1H), 7.35 (d,1H), 7.5–7.6(m,3H), 8.5(t,1H), 8.8(s,1H). | G |
| 48 | R-N-[2-Fluoro-4-(3-fluoroanilino-sulphonyl)phenyl]-3,3,3-trifluoro-2-hydroxy-2-methyl propanamide† | 423 | CDCl$_3$: 1.75(s,3H), 6.7(s,1H), 6.8–6.95(m,3H), 7.15–7.25(m,1H), 7.5–7.6(m,2H), 8.5(t,1H), 8.8(br s,1H). | G |
| 49 | R-N-[2-Fluoro-4-(3-methoxy-anilinosulphonyl)phenyl]-3,3,3-trifluoro-2-hydroxy-2-methyl-propanamide† | 435 | CDCl$_3$: 1.75(s,3H), 3.75(s,3H), 6.5 (s,1H), 6.6(d,1H), 6.65–6.7(m,2H), 7.15(t,1H), 7.5–7.65(m,2H), 8.5(t, 1H), 8.8(s,1H). | G |
| 50 | R-N-[2-Fluoro-4-(3-methylthio-anilinosulphonyl)phenyl]-3,3,3-trifluoro-2-hydroxy-2-methyl-propanamide† | 451 | CDCl$_3$: 1.75(s,3H), 2.45(s,3H), 6.5 (s,1H), 6.8(d,1H), 6.9–7.05(m,2H), 7.15(t,1H), 7.5–7.6(m,2H), 8.5(t, 1H), 8.8(s,1H). | G |
| 51 | R-N-[2-Fluoro-4-(4-fluoroanilino-sulphonyl)phenyl]-3,3,3-trifluoro-2-hydroxy-2-methyl-propanamide† | 423 | 1.6(s,3H), 7.0–7.1(m,4H), 7.5–7.6 (m,2H), 7.7(s,1H), 7.9(t,1H), 9.8(s, 1H), 10.3(br s,1H). | G |
| 52 | R-N-[2-Fluoro-4-(4-methoxy-anilinosulphonyl)phenyl]-3,3,3-trifluoro-2-hydroxy-2-methyl-propanamide† | 435 | CDCl$_3$: 1.75(s,3H), 3.8(s,3H), 6.4(s, 1H), 6.6(d,2H), 7.0(d,2H), 7.4–7.6 (m,2H), 8.5(t,1H), 8.9(br s,1H). | G |
| 53 | R-N-[2-Fluoro-4-(4-benzyloxy-anilinosulphonyl)phenyl]-3,3,3-trifluoro-2-hydroxy-2-methyl-propanamide† | 511 | CDCl$_3$: 1.75(s,3H), 5.0(s,2H), 6.25 (s,1H), 6.8–6.9(m,2H), 6.9–7.0(m, 2H), 7.3–7.5(m,7H), 8.5(t,1H), 8.85 (br s,1H). | G |
| 54 | R-N-{2-Fluoro-4-[1-(t-butyloxy-carbonyl)piperazin-4-ylsulphonyl]phenyl}-3,3,3-trifluoro-2-hydroxy-2-methylpropanamide† | 498 | 1.3(s,9H), 1.6(s,3H), 2.8–2.9(m, 4H), 3.3–3.4(m,4H), 7.6(d,1H), 7.65 (d,1H), 7.8(s,1H), 8.1(t,1H), 9.85(s, 1H). | G |
| 55 | R-N-[2-Fluoro-4-(2-sulphamoyl-anilinosulphonyl)phenyl}-3,3,3-trifluoro-2-hydroxy-2-methyl-propanamide† | 484 | 1.6(s,3H), 7.25(t,1H), 7.45–7.55(m, 2H), 7.7–7.9(m,5H), 8.0(t,1H), 9.35 (br s,1H), 9.8(s,1H). | G |
| 56 | R-N-[2-Fluoro-(4-sulphamoyl-anilinosulphonyl)phenyl]-3,3,3-trifluoro-2-hydroxy-2-methyl propanamide† | 484 | 1.6(s,3H), 7.15–7.25(m,5H), 7.6–7.8 (m,5H), 7.9(s,1H), 9.8(s,1H). | G |
| 57 | R-N-[2-Fluoro-4-(3-benzyloxy-anilinosulphonyl)phenyl]-3,3,3-trifluoro-2-hydroxy-2-methyl-propanamide† | 511 | CDCl$_3$: 1.8(s,3H), 5.0(s,2H), 6.6(d, 1H), 6.65(s,1H), 6.7–6.8(m,2H), 7.1 (t,1H), 7.3–7.4(m,5H), 7.5–7.6(m, 2H), 8.5(t,1H), 8.9(s,1H). | G |
| 58 | R-N-(2-Fluoro-4-(4-methylthio-anilinosulphonyl)phenyl]-3,3,3-trifluoro-2-hydroxy-2-methyl-propanamide† | 451 | 1.6(s,3H), 2.4(s,3H), 7.05(d,2H), 7.1(d,2H), 7.5–7.6(m,2H), 7.7(s, 1H), 7.9(t,1H), 9.8(s,1H), 10.25(br s,1H). | G |
| 59 | R-N-{2-Methyl-4-[1-(t-butyloxy-carbonyl)piperazin-4-ylsulphonyl]phenyl}-3,3,3-trifluoro-2-hydroxy 2-methylpropanamide† | 494 | CDCl$_3$: 1.4(s,9H), 1.7(s,3H), 2.35(s, 3H), 2.9–3.0(m,4H), 3.4–3.6(m,4H), 4.4(s,1H), 7.5(s,1H), 7.6(d,1H), 8.3 (d,1H), 8.7(br s,1H). | J |
| 60 | R-N-[2-Methyl-4-(methylthio-anilinosulphonyl)phenyl)-3,3,3-trifluoro-2-hydroxy-2-methyl-propanamide† | 447 | CDCl$_3$: 1.7(s,3H), 2.25(s,3H), 2.4(s, 3H), 6.6(s,1H), 7.0(d,2H), 7.15(d, 2H), 7.55–7.65(m,2H), 8.2(d,1H), 8.5(s,1H). | J |

| Ex | Compound | MS | Meth |
|---|---|---|---|
| 61 | R-N-[2-Chloro-(2-chloro-4-iodoanilinosulphonyl)phenyl]-3,3,3-trifluoro-2-hydroxy-2-methyl-propanamide* | 581 | F |
| 62 | R-N-[2-Chloro-4-(4-carbamoylanilinosulphonyl)phenyl]-3,3,3-trifluoro-2-hydroxy-2-methyl-propanamide* | 464 | F |
| 63 | R-N-[2-Chloro-4-(3,5-ditrifluoromethylanilinosulphonyl)phenyl]-3,3,3-trifluoro-2-hydroxy-2-methylpropanamide* | 557 | F |
| 64 | R-N-[2-Chloro-4-(2-fluoro-4-iodoanilinosulphonyl)phenyl]-3,3,3-trifluoro-2-hydroxy-2-methyl-propanamide* | 565 | F |

-continued

| | | | |
|---|---|---|---|
| 65 | R-N-[2-Chloro-4-(1,3-benzodioxol-5-ylmethylaminosulphonyl)phenyl]-3,3,3-trifluoro-2-hydroxy-2-methylpropanamide* | 479 | F |
| 66 | R-N-[2-Chloro-4-(pyrid-2-ylmethylaminosulphonyl)phenyl]-3,3,3-trifluoro-2-hydroxy-2-methylpropanamide* | 436 | F |
| 67 | R-N-[2-Chloro-4-(pyrid-3-ylmethylaminosulphonyl)phenyl]-3,3,3-trifluoro-2-hydroxy-2-methylpropanamide* | 436 | F |
| 68 | R-N-[2-Chloro-4-(pyrid-4-ylmethylaminosulphonyl)phenyl]-3,3,3-trifluoro-2-hydroxy-2-methylpropanamide* | 436 | F |
| 69 | R-N-[2-Chloro-4-(3-nitro-4-trifluoromethylanilinosulphonyl)phenyl]-3,3,3-trifluoro-2-hydroxy-2-methylpropanamide* | 534 | F |
| 70 | R-N-[2-Chloro-4-(2,4-dichloroanilinosulphonyl)phenyl]-3,3,3-trifluoro-2-hydroxy-2-methyl-propanamide* | 489 | F |
| 71 | R-N-[2-Chloro-4-(2-nitroanilinosulphonyl)phenyl]-3,3,3-trifluoro-2-hydroxy-2-methylpropanamide* | 466 | F |
| 72 | R-N-[2-Chloro-4-(3-bromoanilinosulphonyl)phenyl]-3,3,3-trifluoro-2-hydroxy-2-methyl-propanamide* | 501 | F |
| 73 | R-N-(2-Chloro-4-(3-chloroanilinosulphonyl)phenyl]-3,3,3-trifluoro-2-hydroxy-2-methyl-propanamide* | 455 | F |
| 74 | R-N-(2-Chloro-4-(3,4-dichloroanilinosulphonyl)phenyl]-3,3,3-trifluoro-2-hydroxy-2-methyl-propanamide* | 489 | F |
| 75 | R-N-(2-Chloro-4-(3,5-dichloroanilinosulphonyl)phenyl]-3,3,3-trifluoro-2-hydroxy-2-methyl-propanamide* | 489 | F |
| 76 | R-N-(2-Chloro-4-(3-trifluoromethylanilinosulphonyl)phenyl]-3,3,3-trifluoro-2-hydroxy-2-methylpropanamide* | 489 | F |
| 77 | R-N-(2-Chloro-4-(3,4-dimethylanilinosulphonyl)phenyl]-3,3,3-trifluoro-2 hydroxy-2-methyl-propanamide* | 449 | F |
| 78 | R-N-(2-Chloro-4-(4-cyanoanilinosulphonyl)phenyl]-3,3,3-trifluoro-2-hydroxy-2-methyl-propanamide* | 446 | F |
| 79 | R-N-(2-Chloro-4-(4-chloroanilinosulphonyl)phenyl]-3,3,3-trifluoro-2-hydroxy-2-methyl-propanamide* | 455 | F |
| 80 | R-N-(2-Chloro-4-(4-nitroanilinosulphonyl)phenyl]-3,3,3-trifluoro-2-hydroxy-2-methyl-propanamide* | 466 | F |
| 81 | R-N-(2-Chloro-4-(4-acetylanilinosulphonyl)phenyl]-3,3,3-trifluoro-2-hydroxy-2-methyl-propanamide* | 463 | F |
| 82 | R-N-(2-Chloro-4-(4-methylanilinosulphonyl)phenyl]-3,3,3-trifluoro-2-hydroxy-2-methyl-propanamide* | 435 | F |
| 83 | R-N-[2-Chloro-4-(benzylaminosulphonyl)phenyl]-3,3,3-trifluoro-2-hydroxy-2-methylpropanamide* | 435 | F |
| 84 | R-N-[2-Chloro-4-(3,4-dichlorobenzylaminosulphonyl)phenyl]-3,3,3-trifluoro-2-hydroxy-2-methyl-propanamide* | 503 | F |
| 85 | R-N-[2-Chloro-4-(4-trifluoromethylanilinosulphonyl)phenyl]-3,3,3-trifluoro-2-hydroxy-2-methyl-propanamide* | 489 | F |
| 86 | R-N-(2-Chloro-4-(3,4-dimethoxyanilinosulphonyl)phenyl]-3,3,3-trifluoro-2-hydroxy-2-methylpropanamide* | 481 | F |
| 87 | R-N-[2-Chloro-4-(2,4-difluorobenzylaminosulphonyl)phenyl]-3,3,3-trifluoro-2-hydroxy-2-methyl-propanamide* | 471 | F |
| 88 | R-N-(2-Chloro-4-(3-methylanilinosulphonyl)phenyl]-3,3,3-trifluoro-2-hydroxy-2-methylpropanamide* | 435 | F |
| 89 | R-N-[2-Chloro-4-(4-fluorobenzylaminosulphonyl)phenyl]-3,3,3-trifluoro-2-hydroxy-2-methyl-propanamide* | 453 | F |
| 90 | R-N-[2-Chloro-4-(4-trifluoromethoxybenzylaminosulphonyl)phenyl]-3,3,3-trifluoro-2-hydroxy-2-methylpropanamide* | 519 | F |
| 91 | R-N-[2-Chloro-4-(4-chlorobenzylaminosulphonyl)phenyl]-3,3,3-trifluoro-2-hydroxy-2-methylpropanamide* | 470 | F |
| 92 | R-N-{2-Chloro4[4-(1,2,3-thiadiazol-4-yl)benzylaminosulphonyl]phenyl}-3,3,3-trifluoro-2-hydroxy-2-methylpropanamide* | 519 | F |
| 93 | R-N-[2-Chloro-4-(2-fluoro-4-trifluoromethylbenzylaminosulphonyl)phenyl]-3,3,3-trifluoro-2-hydroxy-2-methylpropanamide* | 521 | F |
| 94 | R-N-(2-Chloro-4-(4-chloro-3-trifluoromethylanilinosulphonyl)phenyl]-3,3,3-trifluoro-2-hydroxy-2-methylpropanamide* | 523 | F |
| 95 | R-N-[2-Chloro-4-(2-chloro-5-methylanilinosulphonyl)phenyl]-3,3,3-trifluoro-2-hydroxy-2-methylpropanamide† | 469 | D |
| 96 | R-N-[2-Chloro-4-(N-methylanilinosulphonyl)phenyl]-3,3,3-trifluoro-2-hydroxy-2-methyl-propanamide† | 435 | D |
| 97 | R-N-[2-Chloro-4-(N-methyl-4-methoxyanilinosulphonyl)phenyl]-3,3,3-trifluoro-2-hydroxy-2-methylpropanamide† | 465 | D |
| 98 | R-N-(2-Chloro-4-(indolin-1-ylsulphonyl)phenyl]-3,3,3-trifluoro-2-hydroxy-2-methylpropanamide† | 447 | D |
| 99 | R-N-(2-Chloro-4-(N-ethylanilinosulphonyl)phenyl]-3,3,3-trifluoro-2-hydroxy-2-methyl-propanamide | 449 | D |
| 100 | R-N-[2-Fluoro-4-(2-chloro-6-methylanilinosulphonyl)phenyl]-3,3,3-trifluoro-2-hydroxy-2-methyl-propanamide† | 453 | G |
| 101 | R-N-[2-Fluoro-4-(indolen-1-ylsulphonyl)phenyl]-3,3,3-trifluoro-2-hydroxy-2-methylpropanamide† | 431 | G |
| 102 | R-N-[2-Fluoro-4-(N-methylanilinosulphonyl)phenyl]-3,3,3-trifluoro-2-hydroxy-2-methylpropanamide† | 419 | G |
| 103 | R-N-[2-Fluoro-4-(N-ethylanilinosulphonyl)phenyl]-3,3,3-trifluoro-2-hydroxy-2-methyl propanamide† | 433 | G |

-continued

| | | | |
|---|---|---|---|
| 104 | R-N-[2-Fluoro-4-(N-methyl-4-methoxyanilinosulphonyl)phenyl]-3,3,3-trifluoro-2-hydroxy-2-methyl-propanamide† | 449 | G |
| 105 | R-N-[2-Methyl-4-(indolin-1-ylsulphonyl)phenyl]-3,3,3-trifluoro-2-hydroxy-2-methylpropanamide† | 427 | J |

*indicates that no 2,6-di-t-butylpyridine was used in the reaction.
†indicates that no aqueous work-up was used during the final step; instead the reaction mixture was concentrated, DCM(5 ml) was added and the solution loaded onto a Bond Elut column. This was then eluted with iso-hexane (50 ml) followed by 10% EtOAc/DCM to yield the product.
indicates that this sulphonamide was obtained as a by-product from preparation of Example 42

EXAMPLE 106

R-N-[2-Fluoro-4-(3-hydroxyanilinosulphonyl)phenyl]-3,3,3-trifluoro-2-hydroxy-2-methylpropanamide A solution of R-N-[2-fluoro-4-(3-benzyloxyanilinosulphonyl)phenyl]-3,3,3-trifluoro-2-hydroxy-2-methylpropanamide (Example 57) (0.36 g, 0.7 mmol) in ethanol (15 ml) was hydrogenated over 10% Pd/C for 4 h at ambient temperature. The catalyst was removed by filtration and the ethanol evaporated to yield the title compound as a solid (0.18 g, 0.4 mmol).

NMR: 1.6 (s, 3H), 6.4 (d, 1H), 6.5 (d, 1H), 6.6 (s, 1H), 7.0 (t, 1H), 7.6 (d, 2H), 7.7 (s, 1H), 7.95 (t, 1H), 9.45 (s, 1H), 9.8 (s, 1H); MS: 421.

EXAMPLE 107

R-N-[2-Fluoro-4-(4-hydroxyanilinosulphonyl)phenyl]-3.3.3-trifluoro-2-hydroxy-2-methylpropanamide The procedure of Example 106 was repeated using R-N-[2-fluoro-4-(4-benzyloxyanilinosulphonyl)phenyl]-3,3,3-trifluoro-2-hydroxy-2-methylpropanamide (Example 53) (0.39 g, 0.8 mmol) as the starting material to yield the title compound, as a solid (0.26 g, 0.6 mmol). NMR: 1.6 (s, 3H), 6.6 (d, 2H), 6.85 (d, 2H), 7.05–7.15 (m, 1H), 7.4–7.5 (m, 2H) 7.7 (s, 1H), 7.9 (t, 1H), 9.2 (s, 1H), 9.8 (s, 1H); MS: 421.

EXAMPLE 108

R-N-[2-Fluoro-4-3-mesylanilinosulphonyl)phenyl]-3.3.3-trifluoro-2-hydroxy-2-methylpropanamide A solution of R-N-[2-fluoro-4-(3-methylthioanilinosulphonyl)phenyl]-3,3,3-trifluoro-2-hydroxy-2-methylpropanamide (Example 50) (360 mg, 0.8 mmol) and 70% 3-chloroperoxybenzoic acid (390 mg, 1.6 mmol) in DCM (20 ml) was stirred at ambient temperature overnight and then evaporated to dryness and the residue treated with aqueous sodium hydrogen carbonate solution (25 ml). The aqueous solution was extracted with EtOAc, the EtOAc extracts were washed with brine, dried and evaporated to yield the title compound as a solid (0.1 g, 0.2 mmol).

NMR: 1.6 (s, 3H), 3.05 (s, 3H), 7.2–7.7 (m, 8H), 7.95 (t, 1H), 9.8 (s, 1H); MS: 483.

EXAMPLE 109

R-N-[2-Fluoro-4-(2-mesylanilinosulphonyl)phenyl]-3.3.3-trifluoro-2-hydroxy-2-methylpropanamide The procedure of Example 108 was repeated using R-N-[2-fluoro-4-(2-methylthioanilinosulphonyl)phenyl]-3,3,3-trifluoro-2-hydroxy-2-methylpropanamide (Example 47) (290 mg, 0.6 mmol) as the starting material to yield the title compound as a solid (100 mg, 0.2 mmol). NMR: 1.6 (s, 3H), 3.25 (s, 3H), 7.25 (d, 1H), 7.4 (t, 1H), 7.5 (t, 1H), 7.6–7.8 (m, 3H), 7.85–7.95 (m, 2H), 8.05 (t, 1H), 9.85 (s, 1H); MS: 483.

EXAMPLE 110

R-N-{2-Chloro-4-[4-(2-hydroxyethylthio)anilinosulphonyl]phenyl}-3,3,3-trifluoro-2-hydroxy-2-methyloroanamide A solution of S-3,3,3-trifluoro-2-hydroxy-2-methylpropanoyl chloride (Method P) (700 mg, 3.92 mmol) in DCM (25 ml) was added to a stirred mixture of 2-chloro-4-[4-(2-hydroxyethylthio)anilinosulphonyl]aniline (Method R) (630 mg, 1.76 mmol) and 2,6-di-t-butylpyridine (0.9 ml, 4.0 mmol) in DCM (50 ml). The resultant mixture was stirred at ambient temperature overnight and then washed with 1M aqueous hydrochloric acid, aqueous sodium hydrogen carbonate solution and brine then dried and evaporated to dryness. The residue was purified by column chromatography using 20% EtOAc in DCM to yield the title compound as a foam (330 mg, 0.66 mmol). NMR: 1.6 (s, 3H), 2.9 (t, 2H), 3.5 (m, 2H), 4.8 (t, 1H), 7.0 (d, 2H), 7.2 (d, 2H), 7.7 (dd, 1H), 7.8 (d, 1H), 8.2 (d, 1H); MS: 497.

EXAMPLE 111

R-N-{2-Chloro-4-[4-(2-hydroxyethylsulphonyl)anilinosulphonyl]phenyl}-3,3,3-trifluoro-2-hydroxy-2-methylpropanamide A solution of R-N-{2-chloro-4-[4-(2-hydroxyethylthio)anilinosulphonyl]phenyl}-3,3,3-trifluoro-2-hydroxy-2-methylpropanamide (Example 110) (270 mg, 0.54 mmol) and 55% 3-chloroperoxybenzoic acid (340 mg, 1.08 mmol) in DCM (25 ml) was stirred at ambient temperature overnight and then evaporated to dryness and the residue treated with aqueous sodium hydrogen carbonate solution (25 ml). The aqueous solution was extracted with EtOAc, the EtOAc extracts were washed with brine, dried and evaporated. The residue was purified by column chromatography using 50% EtOAc in DCM to yield the title compound as a foam (144 mg, 0.27 mmol). NMR: 1.6 (s, 3H), 3.35 (t, 2H), 3.6 (m, 2H), 4.8 (t, 1H), 7.3 (d, 2H), 7.75 (d, 2H), 7.85 (dd, 1H), 7.95 (d, 1H), 8.25 (d, 1H); MS: 529.

EXAMPLE 112

R-N-{2-Chloro-4-[4-(2-ethoxyethylthio)anilinosulphonyl]phenyl}-3,3,3-trifluoro-2-hydroxy-2-methylpropanamide A solution of S-3,3,3-trifluoro-2-hydroxy-2-methylpropanoyl chloride (Method P) (393 mg, 2.2 mmol) in DCM (25 ml) was added to a stirred mixture of 2-chloro- 4-[4-2-ethoxyethylthio)anilinosulphonyl]aniline (Method S) (770 mg, 2.0 mmol) and 2,6-di-t-butylpyridine (0.51 ml, 2.2 mmol) in DCM (25 ml). The resultant mixture was stirred at ambient temperature for 6 h and then washed with 1M aqueous hydrochloric acid and brine, dried and evaporated to dryness. The residue was purified by column chromatography using 10% EtOAc in DCM to yield the title compound as a foam (520 mg, 0.99 mmol). NMR: 1.0 (t, 3H), 1.6 (s, 3H), 3.0 (t, 2H), 3.3–3.5 (m, 4H), 7.0 (d, 2H), 7.2 (d, 2H), 7.7 (dd, 1H), 7.8 (d, 1H), 8.2 (d, 1H); MS: 525.

EXAMPLE 113

R-N-{2-Chloro-4-[4-(2-ethoxyethylsulphonyl) anilinosulphonyl]phenyl}-3,3,3-trifluoro-2-hydroxy-2-methylpropanamide The procedure of Example 111 was repeated using R-N-{2-chloro-4-[4-(2-ethoxyethylthio)anilinosulphonyl] phenyl}-3,3,3-trifluoro-2-hydroxy-2-methylpropanamide (Example 112) (460 mg, 0.87 mmol) as the starting material to obtain the title compound as a foam (260 mg, 0.46 mmol). NMR: 0.7 (t, 3H), 1.6 (s, 3H), 3.1 (t, 2H), 3.45 (t, 2H), 3.55 (t, 2H), 7.3 (d, 2H), 7.75 (d, 2H), 7.85 (dd, 1H), 8.0 (d, 1H), 8.3 (d, 1H); 557.

EXAMPLE 114

R-N-[2-Chloro-4-(4-methoxycarbonylanilinosulphonyl)phenyl]-3,3,3-trifluoro-2-hydroxy-2-methylpropanamide A solution of S-3,3,3-trifluoro-2-hydroxy-2-methylpropanoyl chloride (Method P) (8.24 g, 46.2 mmol) in DCM (200 ml) was added to a stirred mixture of 2-chloro-4-(4-methoxycarbonylanilinosulphonyl)aniline (Method T) (13.6 g, 40.0 mmol) and 2,6-di-t-butylpyridine (10.3 ml, 46.2 mmol) in DCM (200 ml). The resultant mixture was stirred at ambient temperature overnight and then washed with 1M aqueous hydrochloric acid, aqueous sodium hydrogen carbonate solution and brine, dried and evaporated to dryness. The residue was purified by column chromatography using 10% EtOAc in DCM to yield the title compound as a solid (16.6 g, 34.5 mmol). NMR: 1.6 (s, 3H), 3.8 (s, 3H), 7.2 (d, 2H), 7.8 (dd, 1H), 7.85 (d, 2H), 7.9 (d, 1H), 8.2 (d, 1H); MS: 479.

EXAMPLE 115

R-N-[2-Chloro-4-(4-carboxyanilinosulphonyl) phenyl]-3,3,3-trifluoro-2-hydroxy-2-methylpropanamide A solution of lithium hydroxide (428 mg, 11.6 mmol) in water (10 ml) was added to a solution of R-N-[²-chloro-4-(4-methoxycarbonylanilinosulphonyl)phenyl]-3,3,3-trifluoro-2-hydroxy-2-methylpropanamide (Example 114) (610 mg, 1.27 mmol) in methanol (20 ml). The resultant mixture was stirred at ambient temperature overnight and evaporated to dryness. The residue was dissolved in 1M aqueous hydrochloric acid (15 ml), the aqueous solution was extracted with EtOAc, the EtOAc extracts were washed with brine, dried and evaporated to yield the title compound as a foam (560 mg, 1.2 mmol); microanalysis found: C, 43.8; H, 3.0; N, 5.7%; $C_{17}H_{14}N_2F_3ClSO_6$ requires: C, 43.7; H, 3.0; N, 6.0%; NMR: 1.6 (s, 3H), 7.2 (d, 2H), 7.8 (d, 2H), 7.8 (dd, 1H), 7.95 (d, 1H), 8.2 (d, 1H); MS: 465.

EXAMPLE 116

R-N-[2-Chloro-4-(piperazin-1-ylsulphonyl)phenyl]-3,3,3-trifluoro-2-hydroxy-2-methylpropanamide A solution of S-3,3,3-trifluoro-2-hydroxy-2-methylpropanoyl chloride (Method P) (5.6 g, 31.2 mmol) in DCM (250 ml) was added to a stirred mixture of 2-chloro-4-[1-(t-butoxycarbonyl)piperazin-4-ylsulphonyl]aniline (Method U) (10.7 g, 28.4 mmol) and 2,6-di-t-butylpyridine (7.1 ml, 31.2 mmol) in EtOAc (750 ml). The resultant mixture was stirred at ambient temperature overnight, the DCM evaporated and the EtOAc layer washed with aqueous sodium hydrogen carbonate solution and brine, dried and evaporated to dryness. The residue was dissolved in 3M hydrogen chloride in EtOAc (70 ml), stirred at ambient temperature overnight and evaporated to dryness. The residue was treated with saturated sodium hydrogen carbonate solution, the aqueous solution was extracted with EtOAc, the EtOAc extracts were washed with brine, dried and evaporated. The residue was crystallised from EtOAc to yield the title compound as a solid (7.5 g, 18.0 mmol). NMR: 1.6 (s, 3H), 2.7 (m, 4H), 2.8 (m, 4H), 7.7 (dd, 1H), 7.85 (d, 1H), 8.3 (d, 1H); MS: 414.

EXAMPLE 117

R-N-[2-Chloro-4-(1-acetylpiperazin-4-ylsulphonyl) phenyl]-3,3,3-trifluoro-2-hydroxy-2-methylpropanamide A solution of R-N-[2-chloro-4-(piperazin-1-ylsulphonyl) phenyl]-3,3,3-trifluoro-2-hydroxy-2-methylpropanamide (Example 116) (330 mg, 0.8 mmol) and triethylamine (0.33 ml) in DCM (20 ml) was added to a stirred solution of acetyl chloride (0.13 ml, 1.8 mmol) in DCM (15 ml). The resultant mixture was stirred at ambient temperature overnight and evaporated to dryness. The residue was dissolved in methanol (10 ml) and added to a stirred solution of lithium hydroxide (150 mg, 3.75 mmol) in water (5 ml). The resultant mixture was stirred at ambient temperature for 4 h and then evaporated to dryness and the residue treated with 1M aqueous hydrochloric acid (15 ml). The aqueous solution was extracted with EtOAc, the EtOAc extracts were washed with brine, dried and evaporated to yield the title compound as a foam (81 mg, 0.18 mmol). NMR: 1.6 (s, 3H), 2.0 (s, 3H), 3.0 (m, 4H), 3.6 (m, 4H), 7.8 (dd, 1H), 7.9 (d, 1H), 8.4 (d, 1H); MS: 456.

EXAMPLES 118–125

The procedure of Example 117 was repeated using the appropriate acid chloride or sulphonyl chloride to replace the acetyl chloride to obtain the compounds described below.

| Ex | Compound | MS | $^1$H NMR |
|---|---|---|---|
| 118 | R-N-[2-Chloro-4-(1-mesylpiperazin-4-yl-sulphonyl)phenyl]-3,3,3-trifluoro-2-hydroxy-2-methylpropanamide | 492 | 1.6(s, 3H), 2.9(s, 3H), 3.0(m, 4H), 3.2(m, 4H), 7.8(dd, 1H), 7.9(d, 1H), 8.4(d, 1H). |
| 119 | R-N-{2-Chloro-4-[1-(4-mesylphenyl-sulphonyl)piperazin-4-ylsulphonyl]phenyl}-3,3,3-trifluoro-2-hydroxy-2-methyl-propanamide | 632 | 1.6(s, 3H), 3.0(m, 8H), 3.3(s, 3H), 7.7(dd, 1H), 7.8(d, 1H), 7.95(d, 2H), 8.15(d, 2H), 8.4(d, 1H). |

-continued

| Ex | Compound | MS | $^1$H NMR |
|---|---|---|---|
| 120 | R-N-{2-Chloro-4-[1-(methoxyacetyl)-piperazin-4-ylsulphonyl]phenyl}-3,3,3-trifluoro-2-hydroxy-2-methylpropanamide | 486 | 1.6(s, 3H), 2.95(m, 4H), 3.2(s, 3H), 3.5(m, 4H), 4.0(s, 2H), 7.8(dd, 1H), 7.9(d, 1H), 8.4(d, 1H). |
| 121 | R-N-{2-Chloro-4-[1-(methoxypropionyl)-piperazin-4-ylsulphonyl]phenyl}-3,3,3-trifluoro-2-hydroxy-2-methylpropanamide | 500 | 1.6(s, 3H), 2.5(t, 2H), 2.95(m, 4H), 3.2(s, 3H), 3.5(m, 4H), 3.6(t, 2H), 7.8(dd, 1H), 7.9(d, 1H), 8.4(d, 1H). |
| 122 | RN-{2-Chloro-4-[1-(acetamidoacetyl)-piperazin-4-ylsulphonyl]phenyl}-3,3,3-trifluoro-2-hydroxy-2-methylpropanamide | 513 | 1.6(s, 3H), 1.9(s, 3H), 3.0(m, 4H), 3.6(m, 4H), 3.9.(d, 2H), 7.8(dd, 1H), 7.9(d, 1H), 8.4(d, 1H). |
| 123 | R-N-{2-Chloro-4-[1-(hydroxyacetyl)-piperazin-4-ylsulphonyl]phenyl}-3,3,3-trifluoro-2-hydroxy-2-methylpropanamide | 472 | 1.6(s, 3H), 2.8(m, 2H), 3.0(m, 4H), 3.45–3.6(m, 4H), 7.8(dd. 1H), 7.9(d, 1H), 8.4(d, 1H). |
| 124 | R-N-{2-Chloro-4-[1-(R,S-tetrahydrofuran-3-ylcarbonyl)piperazin-4-ylsulphonyl]phenyl}-3,3,3-trifluoro-2-hydroxy-2-methyl-propanamide | 512 | 1.6(s, 3H), 1.9(m, 2H), 3.0(m, 4H), 3.2(m, 1H), 3.5–3.6 (m, 8H), 7.8(dd, 1H), 7.9(d, 1H), 8.4(d, 1H). |
| 125 | R-N-{2-Chloro-4-[1-(morpholinocarbonyl)piperazin-4-ylsulphonyl)phenyl}3,3,3-trifluoro-2-hydroxy-2-methylpropanamide | 527 | 1.6(s, 3H), 2.9(m, 4H), 3.1(m, 4H), 3.2(m, 4H), 3.5(m, 4H), 7.8(dd, 1H), 7.9(d, 1H), 8.4(d, 1H). |

EXAMPLE 126

R-N-{2-Chloro-4-[(1-aminoacetylpiperazin-4-yl) sulphonyl]phenyl}-3,3,3-trifluoro-2-hydroxy-2-methylpropanamide A solution of R-N-[2-chloro-4-(piperazin-1-ylsulphonyl) phenyl]-3,3,3-trifluoro-2-hydroxy-2-methylpropanamide (Example 116) (330 mg, 0.8 mmol) in tetrahydrofuran (3 ml) was added to a stirred solution of (t-butoxycarbonyl)glycine (149 mg, 0.85 mmol) and carbonyldiimidazole (139 mg, 0.85 mmol) in tetrahydrofuran (8 ml). The resultant mixture was stirred at ambient temperature overnight and evaporated to dryness. The residue was dissolved in 0.7M aqueous citric acid (30 ml); the aqueous solution was extracted with EtOAc, the EtOAc extracts were washed with saturated aqueous sodium hydrogen carbonate solution and brine, dried and evaporated to dryness. The residue was dissolved in 3M hydrogen chloride in EtOAc (10 ml), stirred at ambient temperature for 3 h and evaporated to dryness. The residue was treated with saturated sodium hydrogen carbonate solution, the aqueous solution was extracted with EtOAc, the EtOAc extracts were washed with brine, dried and evaporated to yield the title compound as a foam (230 mg, 0.49 mmol). NMR: 1.6 (s, 3H), 3.0 (m, 4H), 3.4 (m, 2H), 3.45–3.6 (m, 4H), 7.8 (dd, 1H), 7.9 (d, 1H), 8.4 (d, 1H); MS: 471.

EXAMPLE 127

R-N-[2-Chloro-4-(N-acetylsulphamoyl)phenyl]-3,3,3-trifluoro-2-hydroxy-2-methylpropanamide A solution of R-N-(2-chloro-4-sulphamoylphenyl)-3,3,3-trifluoro-2-hydroxy-2-methylpropanamide (Example 40) (150 mg, 0.43 mmol), acetic acid (62.4 mg, 1.04 mmol) and 4-dimethylaminopyridine (380 mg, 3.12 mmol) in DCM (25 ml) was stirred over 4A molecular sieve at ambient temperature for 3 h. 1-(3-dimethylaminopropyl)-3-ethyl carbodiimide hydrochloride (300 mg, 1.57 mmol) was then added to this mixture. The resultant mixture was stirred at ambient temperature overnight and then filtered, washed with 1M aqueous hydrochloric acid, dried and evaporated to dryness. The residue was dissolved in methanol (10 ml) and added to a stirred solution of lithium hydroxide (92 mg, 2.3 mmol) in water (5 ml). The resultant mixture was stirred at ambient temperature for 4 h and then evaporated to dryness and the residue treated with 1M aqueous hydrochloric acid (15 ml). The aqueous solution was extracted with EtOAc, the EtOAc extracts were washed with brine, dried and evaporated to yield the title compound as a foam (118 mg, 0.3 mmol); microanalysis found: C, 38.5; H, 3.6; N, 6.6%; $C_{12}H_{12}N_2F_3ClSO_5$, 0.5 EtOAc requires: C, 38.8; H, 3.7; N, 6.5%; NMR (CDCl$_3$): 1.8 (s. 3H), 2.1 (s, 3H), 7.9 (dd, 1H), 8.2 (d, 1H), 8.7 (s, 1H); MS: 387.

EXAMPLES 128–138

The procedure described in Example 127 was repeated using the appropriate acid to replace the acetic acid to obtain the compounds described below.

| Ex | Example | MS |
|---|---|---|
| 128 | R-N-[2-Chloro-4-(N-benzoylsulphamoyl)phenyl]-3,3,3-trifluoro-2-hydroxy-2-methylpropanamide | 449 |
| 129 | R-N-{2-Chloro-4-[N-(2-chlorobenzoyl)sulphamoyl]phenyl}-3,3,3-trifluoro-2-hydroxy-2-methylpropanamide | 483 |
| 130 | R-N-{2-Chloro-4-[N-(3-iodobenzoyl)sulphamoyl]phenyl}-3,3,3-trifluoro-2-hydroxy-2-methylpropanamide | 575 |
| 131 | R-N-{2-Chloro-4-[N-(4-methylthiobenzoyl)sulphamoyl]phenyl}-3,3,3-trifluoro-2-hydroxy-2-methylpropanamide | 495 |
| 132 | R-N-{2-Chloro-4-[N-(4-cyanobenzoyl)sulphamoyl]phenyl}-3,3,3-trifluoro-2-hydroxy-2-methylpropanamide | 474 |
| 133 | R-N-{2-Chloro-4-[N-(4-benzyloxybenzoyl)sulphamoyl]phenyl}-3,3,3-trifluoro-2-hydroxy-2-methylpropanamide | 555 |
| 134 | R-N-{2-Chloro-4-[N-(4-methoxybenzoyl)sulphamoyl]phenyl}-3,3,3-trifluoro-2-hydroxy-2-methylpropanamide | 479 |
| 135 | R-N-{2-Chloro-4-[N-(4-trifluoromethylbenzoyl)sulphamoyl]phenyl}-3,3,3-trifluoro-2-hydroxy-2-methylpropanamide | 517 |
| 136 | R-N-{2-Chloro-4-[N-(2-chlorobenzylcarbonyl)sulphamoyl]phenyl}-3,3,3-trifluoro-2-hydroxy-2-methylpropanamide | 497 |
| 137 | R-N-{2-Chloro-4-[N-(4-dimethylaminosulphonylbenzoyl)sulphamoyl]phenyl}-3,3,3-trifluoro-2-hydroxy-2-methylpropanamide | 556 |
| 138 | R-N-{2-Chloro-4-(N-(4-mesylbenzoyl)sulphamoyl]phenyl}-3,3,3-trifluoro-2-hydroxy-2-methylpropanamide | 527 |

EXAMPLE 139

R-N-{2-Chloro-4-[N-(aminoacetyl)sulphamoyl] phenyl}-3,3,3-trifluoro-2-hydroxy-2-methylpropanamide Hydrochloride A solution of R-N-(2-chloro-4-sulphamoylphenyl)-3,3,3-trifluoro-2-hydroxy-2-methylpropanamide (Example 40) (345 mg, 1.0 mmol), (tert-butoxycarbonyl)glycine (420 mg, 2.4 mmol) and 4-dimethylaminopyridine (878 mg, 7.2 mmol) in DCM (35 ml) was stirred over 4A molecular sieve at ambient temperature for 3 h. 1-(3-dimethylaminopropyl)-3-ethyl carbodiimide hydrochloride (688 mg, 3.6 mmol) was then added to this mixture. The resultant mixture was stirred at ambient temperature overnight and then filtered, washed with 0.7M aqueous citric acid and brine, dried and evaporated to dryness. The residue was dissolved in methanol (20 ml) and added to a stirred solution of lithium hydroxide (125 mg, 3.0 mmol) in water (10 ml). The resultant mixture was stirred at ambient temperature for 4 h and then evaporated to dryness and the residue treated with 0.7M aqueous citric acid (15 ml). The aqueous solution was extracted with EtOAc, the EtOAc extracts were washed with brine, dried and evaporated. The residue was dissolved in 3M hydrogen chloride in EtOAc (5 ml), stirred at ambient temperature overnight and the solid filtered off to give the title compound (245 mg, 0.6 mmol); MS: 402.

EXAMPLE 140

R-N-{2-Chloro-4-[N-(4-hydroxybenzoyl)sulphamoyl]phenyl}-3,3,3-trifluoro-2-hydroxy-2-methylpropanamide A solution of R-N-{2-chloro-4-[N-(4-benzyloxybenzoyl)sulphamoyl]phenyl}-3,3,3-trifluoro-2-hydroxy-2-methylpropanamide (Example 133) (750 mg, 1.35 mmol) in EtOAc (40 ml) was hydrogenated over 10% Pd/C for 4 h at ambient temperature. The catalyst was removed by filtration and the EtOAc evaporated to yield the title compound as a foam (480 mg, 1.03 mmol). NMR: 1.6 (s, 3H), 6.7 (d, 2H), 7.7 (d, 2H), 7.8 (dd, 1H), 7.9 (d, 1H), 8.1 (d, 1H); MS: 465.

EXAMPLE 141

R-N-[2-Chloro-4-(pyrrol-1-ylsulphonyl)phenyl]-3,3,3-trifluoro-2-hydroxy-2-methylpropanamide A solution of R-N-(2-chloro-4-sulphamoylphenyl)-3,3,3-trifluoro-2-hydroxy-2-methylpropanamide (Example 40) (345 mg, 1.0 mmol), 2,5-diethoxytetrahydrofuran (320 mg, 2.0 mmol) and 4-toluenesulphonic acid (190 mg, 1.0 mmol) in toluene (15 ml) was heated at 100° C. overnight and evaporated to dryness. The residue was dissolved in EtOAc (50 ml) and washed with saturated sodium hydrogen carbonate solution and brine, dried and evaporated to dryness. The residue was purified by column chromatography using 30% EtOAc in hexane to yield the title compound as a solid, (200 mg, 0.5 mmol). NMR: 1.6 (s, 3H), 6.35 (s, 2H), 7.35 (s, 2H), 7.9 (dd, 1H), 8.2 (d, 1H), 8.3 (d, 1H); MS: 395.

EXAMPLE 142

R-N-{2-Chloro-4-[(2-morpholinoethylamino)sulphonyl]phenyl)-3,3,3-trifluoro-2-hydroxy-2-methylpropanamide A solution of R-N-[2-chloro-4-(chlorosulphonyl)phenyl]-3,3,3-trifluoro-2-hydroxy-2-methylpropanamide (Method Y) (366 mg, 1.0 mmol) in DCM (10 ml) was added to a stirred solution of 4-(2-aminoethyl)morpholine (286 mg, 2.2 mmol) in DCM (15 ml). The resultant mixture was stirred at ambient temperature overnight and then washed with aqueous sodium hydrogen carbonate solution and brine, dried and evaporated to dryness. The residue was purified by column chromatography using EtOAc to yield the title compound as a foam (384 mg, 0.84 mmol). NMR: 1.6 (s, 3H), 2.3 (m, 6H), 2.9 (m, 2H), 3.5 (m, 4H), 7.8 (dd, 1H), 7.9 (d, 1H); MS: 458.

EXAMPLES 143–208

The procedure described in Example 142 was repeated using the appropriate amine to replace the 4-(2-aminoethyl)morpholine using DCM or EtOAc as solvent to obtain the compounds described below.

| Ex | Compound | MS | NMR |
|---|---|---|---|
| 143 | R-N-[2-Chloro-4-(4-hydroxypiperidino-sulphonyl)phenyl]-3,3,3-trifluoro-2-hydroxy-2-methylpropanamide | 429 | 1.4(m, 2H), 1.6(s, 3H), 1.75(m, 2H), 2.8(m, 2H), 3.2(m, 2H), 3.5(m, 1H), 4.6(d, 1H), 7.8(dd, 1H), 7.9(d, 1H), 8.35(d, 1H). |
| 144 | R-N-[2-Chloro-4-(2-hydroxyethylamino-sulphonyl)phenyl]-3,3,3-trifluoro-2-hydroxy-2-methylpropanamide | 389 | 1.6(s, 3H), 2.8(m, 2H), 3.4(m, 2H), 4.7(t, 1H), 7.7(t, 1H), 7.8(dd, 1H), 8.0(d, 1H), 8.2(d, 1H). |
| 145 | R-N-[2-Chloro-4-(2-R,S-hydroxypropyl-aminosulphonyl)phenyl]-3,3,3-trifluoro-2-hydroxy-2-methylpropanamide‡¹ | 403 | 1.0(d, 3H), 1.6(s, 3H), 2.65(m, 2H), 3.6(m, 1H), 4.65(d, 1H), 7.7(t, 1H), 7.8(dd, 1H), 7.95(d, 1H), 8.2(d, 1H). |
| 146 | R-N-[2-Chloro-4-(2-R-hydroxypropylamino-sulphonyl)phenyl]-3,3,3-trifluoro-2-hydroxy-2-methylpropanamide‡² | 403 | 1.0(d, 3H), 1.6(s, 3H), 2.65(m, 2H), 3.6(m, 1H), 4.65 (d, 1H), 7.7(t, 1H), 7.8(dd, 1H), 7.95(d, 1H), 8.2(d, 1H). |
| 147 | R-N-[2-Chloro-4-(2-S-hydroxypropylamino-sulphonyl)phenyl]-3,3,3-trifluoro-2-hydroxy-2-methylpropanamide‡³ | 403 | 1.0(d, 3H), 1.6(s, 3H), 2.65(m, 2H), 3.6(m, 1H), 4.65(d, 1H), 7.7(t, 1H), 7.8(dd, 1H), 7.95(d, 1H), 8.2(d, 1H). |
| 148 | R-N-[2-Chloro-4-(2-piperidinoethyl-aminosulphonyl)phenyl]-3,3,3-trifluoro-2-hydroxy-2-methylpropanamide | 456 | 1.3(m, 2H), 1.4(m, 4H), 1.6(s, 3H), 2.2(m, 4H), 2.3(t, 2H), 2.85(t, 2H), 7.8(dd, 1H), 7.9(d, 1H), 8.3(d, 1H). |
| 149 | R-N-[2-Chloro-4-(1-methylpiperazin-4-yl-sulphonyl)phenyl]-3,3,3-trifluoro-2-hydroxy-2-methylpropanamide | 428 | 1.6(s, 3H), 2.15(s, 3H), 2.45(m, 4H), 2.95(m, 4H), 7.75(dd, 1H), 7.85(d, 1H), 8.35(d, 1H). |
| 150 | R-N-[2-Chloro-4-(trans/cis-4-hydroxy-cyclohexylaminosulphonyl)phenyl]-3,3,3-trifluoro-2-hydroxy-2-methylpropanamide | 443 | 1.1–1.5(m, 8H), 1.6(s, 3H), 3.0(m, 1H), 4.4(m, 1H), 7.75(dd, 1H), 7.85(d, 1H), 8.35(d, 1H). |

| Ex | Compound | MS |
|---|---|---|
| 151 | R-N-[2-Chloro-4-(ethylaminosulphonyl)phenyl]-3,3,3-trifluoro-2-hydroxy-2-methyl-propanamide | 373 |
| 152 | R-N-[2-Chloro-4-(n-propylaminosulphonyl)phenyl]-3,3,3-trifluoro-2-hydroxy-2-methylpropanamide | 387 |
| 153 | R-N-[2-Chloro-4-(N-methyl-N-n-propylaminosulphonyl)phenyl]-3,3,3-trifluoro-2-hydroxy-2-methylpropanamide | 401 |
| 154 | R-N-[2-Chloro-4-(2-methoxyethylaminosulphonyl)phenyl]-3,3,3-trifluoro-2-hydroxy-2-methylpropanamide | 403 |
| 155 | R-N-[2-Chloro-4-(3-methoxypropylaminosulphonyl)phenyl]-3,3,3-trifluoro-2-hydroxy-2-methylpropanamide | 417 |
| 156 | R-N-[2-Chloro-4-(3-hydroxypropylaminosulphonyl)phenyl]-3,3,3-trifluoro-2-hydroxy-2-methylpropanamide | 403 |
| 157 | R-N-{2-Chloro-4-[(ethoxycarbonylmethylaminocarbonylmethylamino)sulphonyl]phenyl}-3,3,3-trifluoro-2-hydroxy-2-methyl-propanamide | 488 |
| 158 | R-N-[2-Chloro-4-(methoxycarbonylethylaminosulphonyl)phenyl]-3,3,3-trifluoro-2-hydroxy-2-methylpropanamide | 431 |
| 159 | R-N-[2-Chloro-4-(ethoxycarbonylpropylaminosulphonyl)phenyl]-3,3,3-trifluoro-2-hydroxy-2-methylpropanamide | 459 |

-continued

| | | |
|---|---|---|
| 160 | R-N-[2-Chloro-4-(2-acetamidoethylaminosulphonyl)phenyl]-3,3,3-trifluoro-2-hydroxy-2-methylpropanamide | 430 |
| 161 | R-N-[2-Chloro-4-(3-morpholinopropylaminosulphonyl)phenyl]-3,3,3-trifluoro-2-hydroxy-2-methylpropanamide | 472 |
| 162 | R-N-[2-Chloro-4-(N-methyl-N-allylaminosulphonyl)phenyl]-3,3,3-trifluoro-2-hydroxy-2-methylpropanamide | 399 |
| 163 | R-N-[2-Chloro-4-(4-dimethylaminobutylaminosulphonyl)phenyl]-3,3,3-trifluoro-2-hydroxy-2-methylpropanamide | 444 |
| 164 | R-N-[2-Chloro-4-(4-sulphamoylphenethylaminosulphonyl)phenyl]-3,3,3-trifluoro-2-hydroxy-2-methylpropanamide | 528 |
| 165 | R-N-[2-Chloro-4-(2-methylthioethylaminosulphonyl)phenyl]-3,3,3-trifluoro-2-hydroxy-2-methylpropanamide | 419 |
| 166 | R-N-[2-Chloro-4-(cyclopropylaminosulphonyl)phenyl]-3,3,3-trifluoro-2-hydroxy-2-methylpropanamide | 385 |
| 167 | R-N-[2-Chloro-4-(cyclobutylaminosulphonyl)phenyl]-3,3,3-trifluoro-2-hydroxy-2-methylpropanamide | 399 |
| 168 | R-N-{2-Chloro-4-[N,N-bis-(R,S-2-hydroxypropyl)aminosulphonyl]phenyl}-3,3,3-trifluoro-2-hydroxy-2-methylpropanamide | 461 |
| 169 | R-N-{2-Chloro-4-[N-methyl-N-(2-hydroxyethyl)aminosulphonyl]phenyl}-3,3,3-trifluoro-2-hydroxy-2-methylpropanamide | 403 |
| 170 | R-N-[2-Chloro-4-(thiazolidin-3-ylsulphonyl)phenyl]-3,3,3-trifluoro-2-hydroxy-2-methylpropanamide | 417 |
| 171 | R-N-[2-Chloro-4-pyrrolidin-1-ylsulphonyl)phenyl]-3,3,3-trifluoro-2-hydroxy-2-methylpropanamide | 399 |
| 172 | R-N-{2-Chloro-4-[(R,S-1-hydroxymethyl-3-methylbutyl)aminosulphonyl]phenyl}-3,3,3-trifluoro-2-hydroxy-2-methylpropanamide | 445 |
| 173 | R-N-[2-Chloro-4-(R,S-tetrahydrofuran-2-yl-methylaniosulphonyl)phenyl]-3,3,3-trifluoro-2-hydroxy-2-methylpropanamide | 429 |
| 174 | R-N-[2-Chloro-4-(R,S-3-hydroxymethylpiperidinosulphonyl)phenyl]-3,3,3-trifluoro-2-hydroxy-2-methylpropanamide | 443 |
| 175 | R-N-[2-Chloro-4-(thiomorpholinosulphonyl)phenyl]-3,3,3-trifluoro-2-hydroxy-2-methylpropanamide | 431 |
| 176 | R-N-[2-Chloro-4-(R,S-2-hydroxymethylpiperidinosulphonyl)phenyl]-3,3,3-trifluoro-2-hydroxy-2-methylpropanamide | 443 |
| 177 | R-N-{2-Chloro-4-[R,S-2-(2-hydroxyethyl)piperidinosulphonyl]phenyl}-3,3,3-trifluoro-2-hydroxy-2-methylpropanamide | 457 |
| 178 | R-N-[2-Chloro-4-pyrid-2-ylethylaminosulphonyl)phenyl]-3,3,3-trifluoro-2-hydroxy-2-methylpropanamide | 450 |
| 179 | R-N-[2-Chloro-4-(R,S-1-phenyl-2-hydroxyethylaminosulphonyl)phenyl]-3,3,3-trifluoro-2-hydroxy-2-methylpropanamide | 465 |
| 180 | R-N-[2-Chloro-4-(R,S-1-phenylethylaminosulphonyl)phenyl]-3,3,3-trifluoro-2-hydroxy-2-methylpropanamide | 449 |
| 181 | R-N-[2-Chloro-4-(isopropylaminosulphonyl)phenyl]-3,3,3-trifluoro-2-hydroxy-2-methylpropanamide | 387 |
| 182 | R-N-[2-Chloro-4-(R,S-1-methyl-2-hydroxyethylaminosulphonyl)phenyl]-3,3,3-trifluoro-2-hydroxy-2-methylpropanamide | 403 |
| 183 | R-N-[2-Chloro-4-(R,S-1-ethyl-2-hydroxyethylaminosulphonyl)phenyl]-3,3,3-trifluoro-2-hydroxy-2-methylpropanamide | 417 |
| 184 | R-N-(2-Chloro-4-(2-fluoroethylaminosulphonyl)phenyl]-3,3,3-trifluoro-2-hydroxy-2-methylpropanamide | 391 |
| 185 | R-N-{2-Chloro-4-[2-(2-hydroxyethoxy)ethylaminosulphonyl]phenyl}-3,3,3-trifluoro-2-hydroxy-2-methylpropanamide | 433 |
| 186 | R-N-[2-Chloro-4-(3-ethoxypropylaminosulphonyl)phenyl]-3,3,3-trifluoro-2-hydroxy-2-methylpropanamide | 431 |
| 187 | R-N-[2-Chloro-4-(3-thiomethylpropylaminosulphonyl)phenyl]-3,3,3-trifluoro-2-hydroxy-2-methylpropanamide | 433 |
| 188 | R-N-{2-Chloro-4-[(3-pyrrolin-1-yl)sulphonyl]phenyl}-3,3,3-trifluoro-2-hydroxy-2-methylpropanamide | 397 |
| 189 | R-N-[2-Chloro-4-(R,S-1-hydroxymethyl-2-methylpropylaminosulphonyl)phenyl]-3,3,3-trifluoro-2-hydroxy-2-methylpropanamide | 431 |
| 190 | R-N-[2-Chloro-4-(R,S-1-methyl-2-methoxyethylaminosulphonyl)phenyl]-3,3,3-trifluoro-2-hydroxy-2-methylpropanamide | 417 |
| 191 | R-N-{2-Chloro-4-[N,N-bis-(2-methoxyethyl)aminosulphonyl]phenyl}-3,3,3-trifluoro-2-hydroxy-2-methylpropanamide | 461 |
| 192 | R-N-[2-Chloro-4-(R,S-3-hydroxypyrrolidin-1-ylsulphonyl)phenyl]-3,3,3-trifluoro-2-hydroxy-2-methylpropanamide | 415 |
| 193 | R-N-{2-Chloro-4-[(R,S-1-hydroxymethyl-3-methylthiopropyl)aminosulphonyl]phenyl}-3,3,3-trifluoro-2-hydroxy-2-methylpropanamide | 463 |
| 194 | R-N-{2-Chloro-4-[4-(pyrrolidin-1-yl)piperidinosulphonyl]phenyl}-3,3,3-trifluoro-2-hydroxy-2-methylpropanamide | 482 |
| 195 | R-N-[2-Chloro-4-(4-hydroxymethylpiperidinosulphonyl)phenyl]-3,3,3-trifluoro-2-hydroxy-2-methylpropanamide | 443 |
| 196 | R-N-{2-Chloro-4-[N-methyl-N-(2-methoxyethyl)aminosulphonyl]phenyl}-3,3,3-trifluoro-2-hydroxy-2-methylpropanamide | 417 |
| 197 | R-N-[2-Chloro-4-(1-hydroxyethylpiperazin-4-ylsulphonyl)phenyl]-3,3,3-trifluoro-2-hydroxy-2-methylpropanamide | 458 |
| 198 | R-N-[2-Chloro-4-(3-imidazol-1-ylpropylaminosulphonyl)phenyl]-3,3,3-trifluoro-2-hydroxy-2-methylpropanamide | 453 |
| 199 | R-N-{2-Chloro-4-[N-isopropyl-N-(2-hydroxyethyl)aminosulphonyl]phenyl}-3,3,3-trifluoro-2-hydroxy-2-methylpropanamide | 431 |
| 200 | R-N-{2-Chloro-4-[N-(3-hydroxypropyl)-N-(2-hydroxyethyl)aminosulphonyl]phenyl}-3,3,3-trifluoro-2-hydroxy-2-methylpropanamide | 447 |
| 201 | R-N-[2-Chloro-4-(N-methyl-N-R,S-tetrahydrofur-2-ylaminosulphonyl)phenyl]-3,3,3-trifluoro-2-hydroxy-2-methylpropanamide | 429 |
| 202 | R-N-[2-Chloro-4-(R,S-1-ethylpiperidin-3-ylaminosulphonyl)phenyl]-3,3,3-trifluoro-2-hydroxy-2-methylpropanamide | 456 |
| 203 | R-N-[2-Chloro-4-(3-dimethylaminopropylaminosulphonyl)phenyl]-3,3,3-trifluoro-2-hydroxy-2-methylpropanamide | 430 |
| 204 | R-N-[2-Chloro-4-(5-hydroxypentylaminosulphonyl)phenyl]-3,3,3-trifluoro-2-hydroxy-2-methylpropanamide | 431 |
| 205 | R-N-[2-Chloro-4-(4-hydroxybutylaminosulphonyl)phenyl]-3,3,3-trifluoro-2-hydroxy-2-methylpropanamide | 417 |
| 206 | R-N-{2-Chloro-4-[N-methyl-N-(3-dimethylaminopropyl)aminosulphonyl]phenyl}-3,3,3-trifluoro-2-hydroxy-2-methylpropanamide | 444 |
| 207 | R-N-{2-Chloro-4-[N-methyl-N-(2-dimethylaminoethyl)aminosulphonyl]phenyl}-3,3,3-trifluoro-2-hydroxy-2-methylpropanamide | 430 |
| 208 | R-N-[2-Chloro-4-(1-methylhomopiperazin-4-ylsulphonyl)phenyl]-3,3,3-trifluoro-2-hydroxy-2-methylpropanamide | 442 |

‡[1]The melting point for Example 145 was 117–118° C. and the [α]$_D^{20}$ + 1.46° (c, 10.2 in EtOH).
‡[2]The melting point for Example 146 was 110–111° C. and the [α]$_D^{20}$ + 0.85° (c, 10.0 in EtOH).
‡[3]The melting point for Example 147 was 134–135° C. and the [α]$_D^{20}$ + 1.75° (c, 10.7 in EtOH).

EXAMPLE 209

R-N-[2-Chloro-4-(2-aminoethylaminosulphonyl)phenyl]-3,3,3-trifluoro-2-hydroxy-2-methylpropanamide Hydrochloride A solution of R-N-[2-chloro-4-(chlorosulphonyl)phenyl]-3,3,3-trifluoro-2-hydroxy-2-methylpropanamide (Method Y) (366 mg, 1.0 mmol) in DCM (15 ml) was added to a stirred solution of N-t-butoxycarbonyl ethylenediamine (350 mg, 2.2 mmol) in DCM (10 ml). The resultant mixture was stirred at ambient temperature for 4 h, washed with 1M aqueous citric acid, saturated sodium hydrogen carbonate solution and brine, dried and evaporated to dryness. The residue was dissolved in 3M hydrogen chloride in EtOAc (5 ml) and stirred at ambient temperature overnight. The precipitated solid was filtered off, washed with EtOAc (5 ml) and dried to yield the title compound as a solid (362 mg, 0.63 mmol). NMR: 1.6 (s, 3H), 2.85 (m, 2H), 3.0 (m, 2H), 7.8 (dd, 1H), 8.0 (d, 1H), 8.3 (d, 1H); MS: 388.

EXAMPLE 210

R-N-[2-Chloro-4-(2-dimethylaminoethylaminosulphonyl)phenyl]-3,3,3-trifluoro-2-hydroxy-2-methylpropanamide Hydrochloride A solution of R-N-[2-chloro-4-(chlorosulphonyl)phenyl]-3,3,3-trifluoro-2-hydroxy-2-methylpropanamide (Method Y) (366 mg, 1.0 mmol) in DCM (10 ml) was added to a stirred solution of N,N-dimethylaminoethylamine (194 mg, 2.2 mmol) in DCM (15 ml). The resultant mixture was stirred at ambient temperature overnight and then washed with aqueous sodium hydrogen carbonate solution and brine, dried and evaporated to dryness. The residue was purified by conversion to the hydrochloride salt and recrystallization from EtOAc to yield the title compound (300 mg, 0.72 mmol). NMR: 1.6 (s, 3H), 2.75 (s, 6H), 3.1 (s, 4H), 7.8 (dd, 1H), 8.0 (d, 1H), 8.3 (d, 1H); MS: 416.

EXAMPLE 211

R-N-[2-Chloro-4-(4-aminoanilinosulphonyl)phenyl]-3,3,3-trifluoro-2-hydroxy-2-methylpropanamide A solution of R-N-[2-chloro-4-(chlorosulphonyl)phenyl]-3,3,3-trifluoro-2-hydroxy-2-methylpropanamide (Method Y) (275 mg, 0.75 mmol) in DCM (15 ml) was added to a stirred solution of N-t-butoxycarbonyl-1,4-phenylenediamine (156 mg, 0.75 mmol) and pyridine (0.18 ml, 2.2 mmol) in DCM (10 ml). The resultant mixture was stirred at ambient temperature for 4 h, washed with 1M aqueous citric acid, saturated sodium hydrogen carbonate solution and brine then dried and evaporated to dryness. The residue was dissolved in 3M hydrogen chloride in EtOAc (12 ml), stirred at ambient temperature overnight and evaporated to dryness. The residue was treated with saturated sodium hydrogen carbonate solution, the aqueous solution was extracted with EtOAc, the EtOAc extracts were washed with brine, dried and evaporated. The residue was purified by column chromatography using 25% EtOAc in DCM to yield the title compound as a foam (275 mg, 0.63 mmol). NMR: 1.6 (s, 3H), 5.0 (s, 2H), 6.4 (d, 2H), 6.7 (d, 2H), 7.6 (dd, 1H), 7.7 (d, 1H), 8.2 (d, 1H); MS: 436.

EXAMPLE 212

R-N-[2-Chloro-4-(4-formylanilinosulphonyl) phenyl]-3,3,3-trifluoro-2-hydroxy-2-methylpropanamide A solution of R-N-[2-chloro-4-(chlorosulphonyl)phenyl]-3,3,3-trifluoro-2-hydroxy-2-methylpropanamide (Method Y) (1.2 g, 3.28 mmol) in EtOAc (20 ml) was added to a stirred solution of 2-(4-aminophenyl)-1,3-dioxolane (Method V) (800 mg, 4.85 mmol) and pyridine (0.4 ml, 4.8 mmol) in EtOAc (80 ml). The resultant mixture was stirred at ambient temperature overnight, washed with 1M aqueous hydrochloric acid and brine, dried and evaporated to dryness. The residue was purified by column chromatography using 10% EtOAc in DCM to yield the title compound as a solid (1.1 g, 2.5 mmol). NMR: 1.6 (s, 3H), 7.3 (d, 2H), 7.8 (d, 2H), 7.85 (dd, 1H), 7.95 (d, 1H), 8.2 (d, 1H), 9.8 (s, 1H); MS: 449.

EXAMPLES 213

R-N-[2-Chloro-4-(4-hydroxymethylanilinosulphonyl)phenyl]-3,3,3-trifluoro-2-hydroxy-2-methylpropanamide Sodium borohydride (38 mg, 1.0 mmol) was added to a solution of R-N-[2-chloro-4-(4-formylanilinosulphonyl) phenyl]-3,3,3-trifluoro-2-hydroxy-2-methylpropanamide (Example 212) (225 mg, 0.5 mmol) in ethanol (15 ml). The resultant mixture was stirred at ambient temperature overnight and evaporated to dryness. The residue was dissolved in 1M aqueous hydrochloric acid (15 ml), the aqueous solution was extracted with EtOAc, the EtOAc extracts were washed with brine, dried and evaporated to yield the title compound as a foam (220 mg, 0.5 mmol). NMR: 1.6 (s, 3H), 4.4 (s, 2H), 7.0 (d, 2H), 7.2 (d, 2H), 7.7 (dd, 1H), 7.85 (d, 1H) and 8.2 (d, 1H); MS: 451.

EXAMPLE 214

R-N-{2-Chloro-4-[N-(2-hydroxyethyl)-N-(4-aminophenyl)aminosulphonyl]phenyl}3,3,3-trifluoro-2-hydroxy-2-methylpropanamide A solution of R-N-[2-chloro-4-(chlorosulphonyl)phenyl]-3,3,3-trifluoro-2-hydroxy-2-methylpropanamide (Method Y) (580 mg, 1.58 mmol) in DCM (15 ml) was added to a stirred solution of 4-(2-hydroxyethylamino)aniline (Method W) (285 mg, 1.9 mmol) and pyridine (0.31 ml, 3.7 mmol) in DCM (15 ml). The resultant mixture was stirred at ambient temperature overnight, washed with 1M aqueous hydrochloric acid, dried and evaporated to dryness. The residue was dissolved in methanol (20 ml) and added to a stirred solution of lithium hydroxide (332 mg, 8.0 mmol) in water (10 ml). The resultant mixture was stirred at ambient temperature overnight and then evaporated to dryness and the residue treated with 1M aqueous hydrochloric acid to pH 7.0. The aqueous solution was extracted with EtOAc, the EtOAc extracts were washed with brine, dried and evaporated. The residue was purified by column chromatography using 50% EtOAc in DCM to yield the title compound as a foam (156 mg, 0.3 mmol). NMR: 1.6 (s, 3H), 3.35 (t, 2H), 3.5 (t, 2H), 4.7 (t, 1H), 5.2 (s, 2H), 6.4 (d, 2H), 6.7 (d, 2H), 7.6 (dd, 1H), 7.65 (d, 1H), 8.3 (d, 1H); MS: 480.

EXAMPLE 215

R-N-{-Chloro-4-[4-(2-hydroxyethylamino) anilinosulphonyl]phenyl}-3,3,3-trifluoro-2-hydroxy-2-methylpropanamide A solution of R-N-[2-chloro-4-(chlorosulphonyl)phenyl]-3,3,3-trifluoro-2-hydroxy-2-methylpropanamide (Method Y) (770 mg, 2.1 mmol) in DCM (20 ml) was added to a stirred solution of 4-(N-2-tetrahydropyranyloxyethyl-t-butoxycarbonylamino)aniline (Method X) (620 mg, 1.85 mmol) and pyridine (0.34 ml, 4.08 mmol) in DCM (20 ml). The resultant mixture was stirred at ambient temperature overnight, washed with 1M aqueous citric acid, saturated sodium hydrogen carbonate solution and brine, dried and evaporated to dryness. The residue was dissolved in 3M hydrogen chloride in EtOAc (12 ml), stirred at ambient temperature for 4 h and evaporated to dryness. The residue was treated with saturated sodium hydrogen carbonate solution, the aqueous solution was extracted with EtOAc, the EtOAc extracts were washed with brine, dried and evaporated. The residue was purified by column chromatography using 25% EtOAc in DCM to yield the title compound as a foam (260 mg, 0.45 mmol). NMR: 1.6 (s, 3H), 3.0 (m, 2H), 3.5 (m, 2H), 4.6 (t, 1H), 5.4 (t, 1H), 6.4 (d, 2H), 6.7 (d, 2H), 7.6 (dd, 1H, 7.7 (d, 1H), 8.2 (d, 1H); MS: 480.

EXAMPLE 216

R-N-{2-Chloro-4-[4-(acetamidosulphonyl) anilinosulphonyl]phenyl}-3,3,3-trifluoro-2-hydroxy-2-methylpropanamide A solution of R-N-[2-chloro-4-(4-sulphamoylanilinosulphonyl)phenyl]-3,3,3-trifluoro-2- hydroxy-2-methylpropanamide (Example 36) (175 mg, 0.35 mmol), acetic acid (50 mg, 0.84 mmol) and 4-dimethylaminopyridine (306 mg, 2.51 mmol) in DCM (25 ml) was stirred over 4A molecular sieve at ambient temperature for 3 h. To this mixture was added 1-(3-dimethylaminopropyl)-3-ethyl carbodiimide hydrochloride (242 mg, 1.26 mmol). The resultant mixture was stirred at ambient temperature overnight and then filtered, washed with 1M aqueous hydrochloric acid, dried and evaporated to dryness. The residue was dissolved in methanol (10 ml) and added to a stirred solution of lithium hydroxide (147 mg, 3.5 mmol) in water (5 ml). The resultant mixture was stirred at ambient temperature for 4 h, evaporated to dryness and the residue treated with 1M aqueous hydrochloric acid (15 ml). The aqueous solution was extracted with EtOAc, the EtOAc extracts were washed with brine, dried and evaporated to yield the title compound as a foam (140 mg, 0.26 mmol). NMR: 1.6 (s, 3H), 1.9 (s, 3H), 7.3 (d, 2H), 7.75 (d, 2H), 7.85 (dd, 1H), 7.95 (d, 1H), 8.25 (d, 1H); MS: 542.

EXAMPLE 217

R-N-{2-Chloro-4-[4-(mesylaminocarbonyl) anilinosulphonyl]phenyl}-3,3,3-trifluoro-2-hydroxy-2-methylpropanamide 1-(3-Dimethylaminopropyl)3-ethyl carbodiimide hydrochloride (195 mg, 1.02 mmol) was added to a solution of R-N-[2-chloro-4-(4-carboxyanilinosulphonyl)phenyl]-3,3,3-trifluoro-2-hydroxy-2-methylpropanamide (Example 115) (320 mg, 0.69 mmol), methane sulphonamide (79 mg, 0.82 mmol) and 4-dimethylaminopyridine (250 mg, 2.06 mmol) in DCM (25 ml). The resultant mixture was stirred at ambient temperature overnight, evaporated to dryness and the residue treated with 1M aqueous hydrochloric acid (15 ml). The aqueous solution was extracted with EtOAc, the EtOAc extracts were washed with brine, dried and evaporated to yield the title compound as a foam (130 mg, 0.24 mmol). NMR: 1.6 (s, 3H), 2.8 (s, 3H), 7.0 (d, 2H), 7.7 (d, 2H), 7.8 (dd, 1H), 7.9 (d, 1H), 8.2 (d, 1H); MS: 542.

EXAMPLE 218

R-N-{2-Chloro-4-[4-(1-methylpiperazin-4-ylcarbonyl)anilinosulphonyl]phenyl}-3,3,3-trifluoro-2-hydroxy-2-methylpropanamide Oxalyl chloride (0.07 ml, 0.8 mmol) was added to a solution of R-N-[2-chloro-4-(4-carboxyanilinosulphonyl) phenyl]-3,3,3-trifluoro-2-hydroxy-2-methylpropanamide (Example 115) (314 mg, 0.67 mmol) in DCM (15 ml). The resultant mixture was stirred at ambient temperature overnight and evaporated to dryness. The residue was dissolved in EtOAc (5 ml) and added to a solution of 1-methylpiperazine (150 mg, 1.5 mmol) in EtOAc (5 ml). The resultant mixture was stirred at ambient temperature overnight, washed with 1M aqueous hydrochloric acid, saturated sodium hydrogen carbonate solution and brine, dried and evaporated to yield the title compound as a foam (355 mg, 0.65 mmol); MS: 547.

EXAMPLES 219–238

The procedure of Example 218 was repeated using the appropriate amine to replace the 1-methylpiperazine to obtain the compounds described below.

| Ex | Compound | MS |
|---|---|---|
| 219 | R-N-{2-Chloro-4-[4-(methylaminocarbonyl) anilinosulphonyl]phenyl}-3,3,3-trifluoro-2-hydroxy-2-methylpropanamide | 478 |
| 220 | R-N-{2-Chloro-4-[4-(ethylaminocarbonyl)anilinosulphonyl] phenyl}-3,3,3-trifluoro-2-hydroxy-2-methylpropanamide | 492 |
| 221 | R-N-{2-Chloro-4-[4-(n-propylaminocarbonyl) anilinosulphonyl]phenyl}-3,3,3-trifluoro-2-hydroxy-2-methylpropanamide | 506 |
| 222 | R-N-{2-Chloro-4-[4-(isobutylaminocarbonyl) anilinosulphonyl]phenyl}-3,3,3-trifluoro-2-hydroxy-2-methylpropanamide | 520 |
| 223 | R-N-{2-Chloro-4-[4-(allylaminocarbonyl)anilinosulphonyl] phenyl}-3,3,3-trifluoro-2-hydroxy-2-methylpropanamide | 504 |
| 224 | R-N-{2-Chloro-4-[4-(dimethylaminocarbonyl) anilinosulphonyl]phenyl}-3,3,3-trifluoro-2-hydroxy-2-methylpropanamide | 492 |
| 225 | R-N-{2-Chloro-4-[4-(2-methoxyethylaminocarbonyl) anilinosulphonyl]phenyl}-3,3,3-trifluoro-2-hydroxy-2-methyl-propanamide | 522 |
| 226 | R-N-{2-Chloro-4-[4-(2-dimethylaminoethylaminocarbonyl) anilinosulphonyl]phenyl}-3,3,3-trifluoro-2-hydroxy-2-methylpropanamide | 535 |
| 227 | R-N-{2-Chloro-4-[4-(3-dimethylaminopropylamino-carbonyl)anilinosulphonyl]phenyl}-3,3,3-trifluoro-2-hydroxy-2-methylpropanamide | 549 |

| Ex | Compound | MS | NMR |
|---|---|---|---|
| 228 | R-N-{2-Chloro-4-[4-(2-hydroxy-ethylaminocarbonyl)anilino-sulphonyl]phenyl}-3,3,3-trifluoro-2-hydroxy-2-methyl-propanamide | 508 | 1.6(s, 3H), 3.4(m, 2H), 3.5(m, 2H), 7.2(d, 2H), 7.8(d, 2H), 7.85(dd, 1H), 8.0(d, 1H), 8.3(d, 1H). |
| 229 | R-N-{2-Chloro-4-[4-(morpho-linocarbonyl)anilinosulphonyl] phenyl}-3,3,3-trifluoro-2-hydroxy-2-methylpropanamide | 534 | 1.6(s, 3H), 3.4(m, 4H), 3.6(m, 4H), 7.2(d, 2H), 7.5(d, 2H), 7.85(dd, 1H), 7.95(d, 1H), 8.3(d, 1H). |
| 230 | R-N-{2-Chloro-4-[4-(R,S-2-hydroxypropylaminocarbonyl) anilinosulphonyl]phenyl}-3,3,3-trifluoro-2-hydroxy-2-methyl-propanamide | 522 | 1.1(d, 3H), 1.6(s, 3H), 3.2(m, 2H), 3.8(m, 1H), 7.2(d, 2H), 7.8(d, 2H), 7.85(dd, 1H), 8.0(d, 1H), 8.3(d, 1H). |
| 231 | R-N-{2-Chloro-4-[4-(R,S-2-3-dihydroxypropylaminocarbonyl) anilinosulphonyl]phenyl}-3,3,3-trifluoro-2-hydroxy-2-methylpropanamide | 538 | 1.6(s, 3H), 3.4(m, 4H). 3.6(m, 1H), 7.2(d, 2H), 7.8(d, 2H), 7.85(dd, 1H), 8.0(d, 1H), 8.3(d, 1H). |
| 232 | R-N-{2-Chloro-4-[4-(bis-2-hydroxyethylaminocarbonyl) anilinosulphonyl]phenyl}-3,3,3-trifluoro-2-hydroxy-2-methylpropanamide | 552 | 1.6(s, 3H), 3.4(m, 4H), 3.5(m, 4H), 7.2(d, 2H), 7.8(d, 2H), 7.85(dd, 1H), 8.0(d, 1H), 8.3(d, 1H). |
| 233 | R-N-{2-Chloro-4-[4-(trans/cis-4-hydroxycyclohexylamino-carbonyl)anilinosulphonyl] phenyl}-3,3,3-trifluoro-2-hydroxy-2-methyl-propanamide | 562 | 1.6(s, 3H), 1.3–1.9(m, 8H), 3.8(m, 2H), 7.2(d, 2H), 7.8(d, 2H), 7.85(dd, 1H), 8.0(d, 1H), 8.3(d, 1H). |
| 234 | R-N-{2-Chloro-4-[4-(R,S-tetra-hydrofur-2-ylmethylamino-carbonyl)anilinosulphonyl] phenyl}-3,3,3-trifluoro-2-hydroxy-2-methylpropanamide | 548 | 1.6(s, 3H), 1.8(m, 4H), 3.25(t, 2H), 3.6(m, 1H), 3.75(m, 1H), 3.9(m, 1H), 7.2(d, 2H), 7.8(d, 2H), 7.85(dd, 2H), 8.0(d, 1H), 8.3(d, 1H). |
| 235 | R-N-(2-Chloro-4-[4-(R,S-1-methyl-2-hydroxyethylamino-carbonyl)anilinosulphonyl] phenyl}-3,3,3-trifluoro-2-hydroxy-2-methylpropanamide | 522 | 1.1(d, 3H), 1.6(s, 3H), 3.4(m, 2H), 3.9(m, 1H), 7.2(d, 2H), 7.8(d, 2H), 7.85(dd, 1H), 8.0(d, 1H), 8.3(d, 1H). |
| 236 | R-N-{2-Chloro-4-[4-(R,S-1-methyl-2-methoxyethylamino-carbonyl)anilinosulphonyl] phenyl}-3,3,3-trifluoro-2-hydroxy-2-methylpropanamide | 536 | 1.1(d, 3H), 1.6(s, 3H), 3.2(s, 3H), 3.4(m, 2H), 4.1(m, 1H), 7.2(d, 2H), 7.8(d, 2H), 7.85(dd, 1H). 8.0(d, 1H), 8.3(d, 1H). |

-continued

| | | | |
|---|---|---|---|
| 237 | R-N-(2-Chloro-4-{4-[N-methyl-N-(2-hydroxyethyl)amino-carbonyl]anilinosulphonyl}phenyl)-3,3,3-trifluoro-2-hydroxy-2-methylpropanamide | 522 | 1.6(s, 3H), 2.9(s, 3H), 3.4(m, 2H), 3.5(m, 2H), 7.2(d, 2H), 7.8(d, 2H), 7.85(dd, 1H), 8.0(d, 1H), 8.3(d, 1H). |
| 238 | R-N-(2-Chloro-4-{4-[N-methyl-N-(2-methoxyethyl)amino-carbonyl]anilinosulphonyl} phenyl)-3,3,3-trifluoro-2-hydroxy-2-methylpropanamide | 536 | 1.6(s, 3H), 2.9(s, 3H), 3.3(s, 3H), 3.4(m, 2H), 3.5(m, 2H). 7.2(d, 2H), 7.8(d, 2H), 7.85(dd, 1H). 8.0(d, 1H), 8.3(d, 1H). |

EXAMPLE 239

R-N-{2-Chloro-4-[4-(2-hydroxyethylaminosulphonyl)anilinosulphonyl]phenyl}-3,3,3-trifluoro-2-hydroxy-2-methylpropanamide A solution of R-N-[2-chloro-4-(4-fluorosulphonylanilinosulphonyl)phenyl]-3,3,3-trifluoro-2-hydroxy-2-methylpropananide (Method O) (250 mg, 0.5 mmol), ethanolamine (92 mg, 1.5 mmol) and 4-dimethylaminopyridine (10 mg, 0.08 mmol) in ethanol (25 ml) was heated at 78° C. overnight and evaporated to dryness. The residue was treated with 1M aqueous hydrochloric acid (10 ml). The aqueous solution was extracted with EtOAc, the EtOAc extracts were washed with brine, dried and evaporated to yield the title compound as a foam (200 mg, 0.37 mmol). NMR: 1.6 (s, 3H), 2.8 (m, 2H), 3.3 (m, 2H), 4.6 (t, 1H), 7.3 (d, 2H), 7.7 (d, 2H), 7.8 (dd, 1H), 7.9 (d, 1H), 8.2 (d, 1H); MS: 544.

EXAMPLES 240–248

The procedure of Example 239 was repeated using the appropriate amine to replace the ethanolamine to obtain the compounds described below.

| Ex | Compound | MS | NMR |
|---|---|---|---|
| 240 | R-N-{2-Chloro-4-[4-R,S-2-3-dihydroxy-propylaminosulphonyl)anilinosulphonyl]phenyl}-3,3,3-trifluoro-2-hydroxy-2-methyl-propanamide | 574 | 1.6(s, 3H), 2.8(m, 1H), 3.2(m, 2H), 3.4(m, 2H), 7.3(d, 2H). 7.6(d, 2H), 7.8(dd, 1H), 7.9(d, 1H), 8.2(d, 1H). |
| 241 | R-N-{2-Chloro-4-[4-(R,S-2-hydroxypropyl-aminosulphonyl)anilinosulphonyl]phenyl}-3,3,3-trifluoro-2-hydroxy-2-methyl-propanamide | 558 | 1.1(d, 3H), 1.6(s, 3H), 2.6(m, 2H), 3.5(m, 1H), 7.3(d, 2H), 7.6(d, 2H), 7.8(dd, 1H), 7.9(d, 1H), 8.2(d, 1H). |
| 242 | R-N-{2-Chloro-4-[4-(2-dimethylamino-ethylaminosulphonyl)anilinosulphonyl]phenyl}-3,3,3-trifluoro-2-hydroxy-2-methylpropanamide hydrochloride | 571 | 1.6(s, 3H), 2.7(s, 6H), 3.1(m, 4H), 7.3(d, 2H), 7.6(d, 2H), 7.8(dd, 1H), 7.9(d, 1H), 8.2(d, 1H). |
| 243 | R-N-{2-Chloro-4-[4-(ethylaminosulphonyl)anilinosulphonyl]phenyl}-3,3,3-trifluoro-2-hydroxy-2-methylpropanamide | 528 | 0.9(t, 3H), 1.6(s, 3H), 2.7(q, 2H), 7.3(d, 2H), 7.6(d, 2H), 7.8(dd, 1H), 7.9(d, 1H), 8.2(d, 1H). |
| 244 | R-N-{2-Chloro-4-[4-(methylamino-sulphonyl)anilinosulphonyl]phenyl}-3,3,3-trifluoro-2-hydroxy-2-methylpropanamide | 514 | 1.6(s, 3H), 2.3(d, 3H), 7.3(d, 2H), 7.6(d, 2H), 7.8(dd, 1H), 7.9(d, 1H), 8.2(d, 1H). |
| 245 | R-N-{2-Chloro-4-[4-(allylaminosulphonyl)anilinosulphonyl]phenyl}-3,3,3-trifluoro-2-hydroxy-2-methylpropanamide | 540 | 1.6(s, 3H), 3.4(d, 2H), 5.0–5.2(m, 2H), 5.65(m, 1H), 7.3(d, 2H), 7.6(d, 2H), 7.8(dd, 1H), 7.9(d, 1H), 8.2(d, 1H). |
| 246 | R-N-{2-Chloro-4-[4-(dimethylamino-sulphonyl)anilinosulphonyl)phenyl}-3,3,3-trifluoro-2-hydroxy-2-methylpropanamide | 528 | 1.6(s, 3H), 2.5(s, 6H), 7.3(d, 2H), 7.6(d, 2H), 7.8(dd, 1H), 7.9(d, 1H), 8.2(d, 1H). |
| 247 | R-N-{2-Chloro-4-[4-(R,S-3-hydroxy-pyrrolidin-1-ylsulphonyl)anilinosulphonyl]phenyl}-3,3,3-trifluoro-2-hydroxy-2-methyl-propanamide | 570 | 1.6(s, 3H), 1.65(m, 2H), 2.9(d, 1H), 3.2(m, 3H), 4.1(m, 1H), 7.3(d, 2H), 7.6(d, 2H), 7.8(dd. 1H). 7.9(d, 1H), 8.2(d, 1H). |
| 248 | R-N-{2-Chloro-4-[4-(trans/cis-4-hydroxy-cyclohexylaminosulphonyl)anilino-sulphonyl]phenyl}-3,3,3-trifluoro-2-hydroxy-2-methyl-propanamide | 598 | 1.1–1.5(m, 8H), 1.6(s, 3H), 2.9(d, 1H), 4.5(m, 1H), 7.3(d, 2H), 7.7(d, 2H), 7.9(dd, 1H), 8.1(d, 1H), 8.3(d, 1H). |

-continued

| | | | |
|---|---|---|---|
| | phenyl)-3,3,3-trifluoro-2-hydroxy-2-methylpropanamide | | 7.8(d, 2H), 7.85(dd, 1H). 8.0(d, 1H), 8.3(d, 1H). |

EXAMPLES 249

R-N-[2-Chloro-4-(5-trifluoromethylpyrid-2-ylaminosulphonyl)phenyl]3,3,3-trifluoro-2-hydroxy-2-methylpropanamide R-N-(2-chloro-4-chlorosulphonylphenyl)-3,3,3-trifluoro-2-hydroxy-2-methylpropanamide (Method M) (293 mg, 0.80 mmol) and 2-amino-5-trifluoromethylpyridine (130 mg, 0.80 mmol) were dissolved in pyridine (2 ml). The resulting mixture was stirred at 85° C. for 20 h. The mixture was then cooled to room temperature and concentrated under vacuum to yield an oil, which was purified on a Bond Elut column to yield the title compound as a solid (285 mg, 0.58 mmol). NMR: 1.55 (s, 3H), 7.15 (d, 1H), 7.90 (m, 2H), 8.02 (m, 2H), 8.21 (d, 1H), 8.51 (s, 1H), 9.84 (s, 1H), 12.09 (br s, 1H); MS: 490.

EXAMPLES 250–264

The procedure of Example 249 was repeated using the appropriate aminoheterocycle to replace the 2-amino-5-trifluoromethyl pyridine to obtain the compounds described below, in yields of 18–92%.

| Ex | Example | MS | NMR |
|---|---|---|---|
| 250 | R-N-[2-Chloro-4-(pyrid-4-ylamino-sulphonyl)phenyl]-3,3,3-trifluoro-2-hydroxy-2-methylpropanamide | 422 | 1.59(s, 3H), 6.91(d, 2H), 7.76(d, 1H), 7.84(s, 1H), 7.90(brs, 1H), 7.98(d, 2H), 8.10(d, 1H), 9.80(s, 1H). |
| 251 | R-N-[2-Chloro-4-(pyrimidin-2-ylamino-sulphonyl)phenyl]-3,3,3-trifluoro-2-hydroxy-2-methylpropanamide | 423 | 1.53(s, 3H), 7.00(t, 1H), 7.89(s, 1H), 7.93(d, 1H), 8.00(d, 1H), 8.18(d, 1H), 8.47(d, 2H), 9.80(s, 1H), 12.0(brs, 1H). |
| 252 | R-N-[2-Chloro-4-(5-methylpyrid-2-yl-aminosulphonyl)phenyl]-3,3,3-trifluoro-2-hydroxy-2-methylpropanamide | 436 | 1.47(s, 3H), 2.02(s, 3H), 7.02(d, 1H), 7.51(dd, 1H), 7.68–7.91(m, 4H), 8.05(d, 1H), 9.73(brs, 1H). |
| 253 | R-N-[2-Chloro-4-(5-chloropyrid-2-yl-aminosulphonyl)phenyl]-3,3,3-trifluoro-2-hydroxy-2-methylpropanamide | 456 | 1.65(s, 3H), 7.13(d, 1H), 7.85(d, 1H), 7.94(d, 1H), 8.01(s, 1H), 8.08(s, 1H), 8.32(m, 2H), 9.91(s, 1H), 11.5(brs, 1H). |
| 254 | R-N-[2-Chloro-4-(pyrid-2-ylamino-sulphonyl)phenyl]-3,3,3-trifluoro-2-hydroxy-2-methylpropanamide | 422 | 1.58(s, 3H), 6.85(t, 1H), 7.20(d, 1H), 7.75(t, 1H), 7.86(d, 1H), 7.94(m, 3H), 8.16(d, 1H), 9.81(s, 1H). |
| 255 | R-N-[2-Chloro-4-(2-carbamoylthien-2-yl-aminosulphonyl)phenyl]-3,3,3-trifluoro-2-hydroxy-2-methylpropanamide[†1] | 470 | 1.58(s, 3H), 7.19(d, 1H), 7.65–7.87(m, 4H), 7.95(s, 1H), 8.00(s, 1H), 8.24(d, 1H), 9.85(s, 1H), 11.2(brs, 1H). |
| 256 | R-N-[2-Chloro-4-(4,6-dimethylpyrid-2-yl aminosulphonyl)phenyl]-3,3,3-trifluoro-2-hydroxy-2-methyl-propanamide | 450 | 1.60(s, 3H), 2.23(s, 3H), 2.28(s, 3H), 6.53(s, 1H), 6.92(brs, 1H) 7.75–7.96(m, 3H), 8.13(d, 1H), 9.82(s, 1H). |
| 257 | R-N-[2-Chloro-4-(3,5-dichloropyrid-2-yl-aminosulphonyl)phenyl]-3,3,3-trifluoro-2-hydroxy-2-methyl-propanamide | 490 | |
| 258 | R-N-[2-Chloro-4-(pyrid-3-ylamino-sulphonyl)phenyl]-3,3,3-trifluoro-2-hydroxy-2-methylpropanamide | 422 | 1.58(s, 3H), 7.30(m, 1H), 7.50(d, 1H), 7.73(d, 1H), 7.88(s, 1H), 7.95(s, 1H), 8.27(m, 3H), 9.83(s, 1H). |
| 259 | R-N-[2-Chloro-4-(2-chloropyrid-3-yl-aminosulphonyl)phenyl]-3,3,3-trifluoro-2-hydroxy-2-methylpropanamide | 456 | 1.60(s, 3H), 7.40(m, 1H), 7.70(d, 2H), 7.84(s, 1H), 7.99(s, 1H), 8.26(m, 2H), 9.86(s, 1H), 10.44(s, 1H). |
| 260 | R-N-[2-Chloro-4-(4-dimethylamino-6-methylpyrimidin-2-ylaminosulphonyl) phenyl]-3,3,3-trifluoro-2-hydroxy-2-methylpropanamide[†2] | 480 | 1.59(s, 3H); 2.10(s, 3H), 2.95(s, 6H), 6.02(s, 1H), 7.71(d, 1H), 7.86(s, 2H), 8.04(d, 1H), 9.79(s, 1H), 11.88(brs, 1H). |
| 261 | R-N-[2-Chloro-4-(2,3-dimethylpyrazin-5-ylaminosulphonyl)phenyl]-3,3,3-trifluoro-2-hydroxy-2-methyl-propanamide[†3] | 451 | 1.58(s, 3H), 2.32(s, 6H). 7.94(m, 2H), 8.05(s, 1H), 8.10(s, 1H). 8.22(d, 1H), 9.88(s, 1H), 11.31(brs, 1H). |
| 262 | R-N-[2-Chloro-4-(3,5-dimethylisoxazol-4-ylaminosulphonyl)phenyl]-3,3,3-trifluoro-2-hydroxy-2-methyl-propanamide[†4] | 440 | 1.60(s, 3H), 1.83(s, 3H), 1.96(s, 3H), 7.67(dd, 1H), 7.78(s, 1H), 8.23(d, 1H). |
| 263 | R-N-[2-Chloro-4-(4,6-dimethyl-pyrimidin-2-ylaminosulphonyl)phenyl]-3,3,3-trifluoro-2-hydroxy-2-methyl-propanamide | 451 | 1.59(s, 3H), 2.25(s, 6H). 6.72(s, 1H), 7.91(m, 2H), 8.12(s, 1H), 8.17(d, 1H), 9.83(s, 1H). |
| 264 | R-N-[2-Chloro-4-(pyrazin-2-ylamino-sulphonyl)phenyl]-3,3,3-trifluoro-2-hydroxy-2-methylpropanamide | 423 | 1.58(s, 3H), 7.93(m, 2H), 8.08(s, 1H), 8.24(m, 3H), 8.34(s, 1H), 9.87(s, 1H). |

[†1]The starting aminoheterocycle for Example 255, 2-amino-3-carbamoylthiophene, was prepared according to the procedure described in J. Med. Chem., 1996, 39 (8), p1635.
[†2]The starting aminoheterocycle for Example 260, 2-amino-4-dimethylamino-6-methyl-pyrimidine, was prepared according to the procedure described in US patent Application: US 77-769475 770217.
[†3]The starting aminoheterocycle for Example 261, 2-amino-5,6-dimethylpyrazine, was prepared according to the procedure described in Chem. Ber., 1967, 100 (2), p560–563.
[†4]The starting aminoheterocycle for Example 262, 4-amino-3,5-dimethylisoxazole was prepared according to the procedure described in Helv. Chim. Acta, 1991, 74 (3), p531.

EXAMPLE 265

R-N-[2-Chloro-4-(N'-phenylureidosulphonyl) phenyl]-3,3,3-trifluoro-2-hydroxy-2-methylpropnanamide A solution of R-N-(2-chloro-4-sulphamoylphenyl)-3,3,3-trifluoro-2-hydroxy-2-methylpropanamide (Example 40) (345 mg, 1.0 mmol), phenyl isocyanate (122 mg, 1.02 mmol) and copper (I) chloride (5 mg, 0.052 mmol) in DMF (5 ml) was stirred at ambient temperature for 24 h. The solution was poured onto water and this was acidified with 1M aqueous hydrochloric acid (1 ml). The precipitated solid was extracted with diethyl ether (25 ml) and the ether extract dried and evaporated. The residue was purified by column chromatography using 10% EtOAc in DCM to yield the title compound as a solid (70 mg, 0.15 mmol). NMR: 1.9 (s, 3H), 7.0 (t, 1H), 7.3 (t, 2H), 7.5 (m. 4H), 7.6 (d, 1H), 7.8 (dd, 1H), 7.9 (d, 1H); MS: 464.

EXAMPLE 266

R-N-{2-Chloro-4-[N-methyl-N-(pyrazin-2-yl) aminosulphonyl]phenyl}-3,3,3-trifluoro-2-hydroxy-2-methylpropanamide Potassium carbonate (65 mg, 0.47 mmol) and R-N-[2-chloro-4-(pyrazin-2-ylaminosulphonyl)phenyl]-3,3,3-trifluoro-2-hydroxy-2-methylpropanamide (Example 264) (200 mg, 0.47 mmol) were added to acetone (10 ml). Methyl iodide (0.03 ml, 0.48 mmol) was added to the resulting suspension and the mixture was stirred at ambient temperature for 22 h before being concentrated under vacuum. Water (15 ml) was added to the residue, which was acidified with 2M HCl and extracted with DCM (2×40 ml). The combined extracts were washed with brine (25 ml), dried and concentrated under vacuum to leave a foam, which was purified by column chromatography to yield the title compound as a foam (100 mg, 0.23 mmol). NMR: 1.60 (s, 3H), 3.25 (s, 3H), 7.66 (d, 1H), 7.82 (s, 1H), 8.27 (d, 1H), 8.42 (s, 1H), 8.52 (s, 1H), 8.80 (s, 1H); MS: 437.

EXAMPLE 267

R-N-[2-Chloro-4-[-N-methyl-N-(5-trifluoromethylpyrid-2-yl)aminosulphonyl]phenyl}-3,3,3-trifluoro-2-hydroxy-2-methylpropanamide Potassium carbonate (51 mg, 0.52 mmol) and R-N-[2-chloro-4-(5-trifluoromethylpyrid-2-ylaminosulphonyl)phenyl]-3,3,3-trifluoro-2-hydroxy-2-methylpropanamide (Example 249) (180 mg, 0.37 mmol) were added to acetone (10 ml). Methyl iodide (0.023 ml, 0.37 mmol) was then added to the resulting suspension and the mixture was stirred at room temperature for 22 h before being concentrated under vacuum. Water (2 ml) was added to the residue, which was acidified with 2M HCl and DCM (1 ml) was added. The mixture was absorbed onto a Bond Elut column and allorganic components of the mixture were washed off with DCM. This resulting solution was concentrated under vacuum to yield a residue that was purified by column chromatography to yield the title compound as a foam (66 mg, 0.13 mmol). NMR: 1.60 (s, 3H), 3.38 (s. 3H), 7.74 (d, 1H), 7.78 (d, 1H), 7.93 (s, 1H), 8.05 (br s, 1H), 8.26 (d, 1H), 8.29 (d, 1H), 8.73 (s, 1H), 9.90 (br s, 1H); MS: 504.

EXAMPLE 268

R-N-{2-Chloro-4-[N-ethyl-N-(pyrazin-2-yl)aminosulphonyl]phenyl}-3,3,3-trifluoro-2-hydroxy-2-methylpropanamide Potassium carbonate (64 mg, 0.65 mmol) and R-N-[2-chloro-4-(pyrazin-2-ylaminosulphonyl)phenyl]-3,3,3-trifluoro-2-hydroxy-2-methylpropanamide (Example 264) (203 mg, 0.47 mmol) were added to acetone (10 ml). Ethyl iodide (0.078 ml, 0.98 mmol) was added to the resulting suspension and the mixture was stirred at room temperature for 96 h before being concentrated under vacuum. 1M HCl (15 ml) was added to the residue which was then extracted with EtOAc (2×15 ml). The combined extracts were washed with brine (25 ml), dried and concentrated under vacuum to leave a foam which was purified by column chromatography to yield the title compound as a foam (78 mg, 0.17 mmol). NMR: 1.04 (t, 3H), 1.60 (s, 3H), 3.80 (q, 2H), 7.67 (d, 1H), 7.85 (s, 1H), 8.05 (br s, 1H), 8.28 (d, 1H), 8.48 (s, 1H), 8.57 (s, 1H), 8.78 (s, 1H), 9.89 (br s, 1H); MS: 451.

EXAMPLE 269

R-N-{2-Chloro-4-[N-ethyl-N-(5-trifluoromethylpyrid-2-yl)aminosulphonyl]phenyl}-3,3,3-trifluoro-2-hydroxy-2-methylpropanamide Potassium carbonate (74 mg, 0.75 mmol) and R-N-[2-chloro-4-(5-trifluoromethylpyrid-2-ylaminosulphonyl)phenyl]-3,3,3-trifluoro-2-hydroxy-2-methylpropanamide (Example 249) (246 mg, 0.51 mmol) were added to acetone (10 ml). Ethyl iodide (0.045 ml, 0.055 mmol) was added to the resulting suspension and the mixture was stirred at room temperature for 22 h. Ethyl iodide (0.045 ml, 0.055 mol) was added to the mixture which was then stirred at room temperature for a further 46 h before being concentrated under vacuum. 1M HCl (5 ml) and EtOAc (1 ml) were added to the residue, which was absorbed onto a Bond Elut column and all organic components of the mixture were washed off with EtOAc. This resulting solution was concentrated under vacuum to leave a residue that was purified by column chromatography to yield the title compound as a foam (81 mg, 0.16 mmol). NMR: 1.18 (m, 3H), 1.60 (s, 3H), 4.00 (m, 2H), 7.68 (d, 1H), 7.80 (d, 1H), 7.96 (s, 1H), 8.25 (d, 1H), 8.29 (d, 1H), 8.76 (s, 1H), 9.85 (br s, 1H); MS: 518.

EXAMPLE 270

R-N-[2-Chloro-4-(4-hydroxyanilinosulphonyl)phenyl]-3.3.3-trifluoro-2-hydroxy-2-methylpropanamide A solution of R-N-[2-chloro-4-(4-benzyloxyanilinosulphonyl)phenyl]-3,3,3-trifluoro-2-hydroxy-2-methylpropanamide (Example 39) (1.85 g, 3.5 mmol) in EtOAc (200 ml) was hydrogenated over 10% Pd/C for 4 h at ambient temperature. The catalyst was removed by filtration and the EtOAc evaporated. The residue was purified by column chromatography using 10% EtOAc in DCM to yield the title compound as a foam (1.55 g, 3.5 mmol). NMR: 1.6 (s, 3H), 6.6 (d, 2H), 6.8 (d, 2H), 7.6 (dd, 1H), 7.75 (d, 1H), 8.2 (d, 1H); MS: 437.

EXAMPLE 271

S-N-{2-Chloro-4-[(4-sulphamoylanilino)sulphonyl]phenyl}-3,3,3-trifluoro-2-hydroxy-2-methylpropanamide A solution of R-3,3,3-trifluoro-2-hydroxy-2-methylpropanoylchloride (Method C1) (223 mg, 1.25 mmol) in DCM (10 ml) was added to a stirred mixture of 2-chloro-4-[(4-sulphamoylanilino)sulphonyl]aniline (Method A1) (362 mg, 1.0 mmol) and 2,6-di tert butylpyridine (0.28 ml, 1.25 mmol) in EtOAc (25 ml). The resultant mixture was stirred at ambient temperature overnight, evaporated to dryness, the residue dissolved in EtOAc and washed with 1M aqueous hydrochloric acid, aqueous sodium hydrogen carbonate solution and brine, dried and evaporated to dryness. The residue was purified by column chromatography using 25% EtOAc in hexane to give, as a foam, the title compound (270 mg, 0.54 mmol). EA found: C, 39.4; H, 3.4; N, 7.4; S, 11.5%; $C_{16}H_{15}N_3F_3ClS_2O_6$ 0.5 EtOAc requires: C, 39.6; H, 3.5; N, 7.7; S, 11.7%; NMR: 1.6 (s, 3H), 7.2 (s, 2H), 7.25 (d, 2H), 7.65 (d, 2H), 7.8 (dd, 1H), 7.95 (d, 1H), 8.2 (d, 1H); MS: 500.

EXAMPLE 272

R-N-[2-Chloro-5-(2-chloroanilinosulphonyl)phenyl]-3,3,3-trifluoro-2-hydroxy-2-methylpropanamide A solution of S-3,3,3-trifluoro-2-hydroxy-2-methylpropanoylchloride (Method P) (95 mg, 0.53 mmol) in DCM (5 ml) was added to a stirred mixture of 2-chloro-5-(2-chloroanilinosulphonyl)aniline (Method B1) (140 mg, 0.44 mmol) and 2,6-di-t-butylpyridine (0.12 ml, 0.53 mmol) in DCM (10 ml). The resultant mixture was stirred at ambient temperature overnight, evaporated to dryness, the residue dissolved in EtOAc and washed with 1M aqueous hydrochloric acid and brine, dried and evaporated to dryness. The residue was purified by column chromatography using 5% EtOAc in DCM to give, as a foam, the title compound (178 mg, 0.39 mmol). NMR: 1.6 (s, 3H), 7.2 (m, 3H), 7.4 (d, 1H), 7.45 (dd, 1H), 7.75 (d, 1H), 8.4 (d, 1H); MS: 455.

Preparation of Starting Materials

The starting materials for the Examples above are either commercially available or are readily prepared by standard methods from known materials. For example the following reactions (Methods A–B1) are illustrations but not limitations of the preparation of some of the starting materials used in the above reactions.

Method A

2-Chloro-4-(morpholinosulphonyl)anilino

A solution of N-acyl-2-chloro-4-chlorosulphonylaniline (536 mg, 2 mmol), morpholine (0.2 ml, 2.3 mmol), 4-dimethylaminopyridine (10 mg, 0.08 mmol) and pyridine (0.19 ml, 2.3 mmol) in DCM (25 ml) was stirred at ambient temperature for 4 h. The mixture was washed with water and brine, dried and evaporated to dryness. The residue was dissolved in ethanol (25 ml) and 2M aqueous sodium hydroxide (5 ml) was added. The mixture was heated at reflux for 4 h and then cooled to ambient temperature, evaporated to dryness and water (25 ml) was added to the residue. The aqueous solution was extracted with EtOAc; the organic phase was separated then washed with water, dried and evaporated to dryness to yield the title compound (500 mg, 1.8 mmol). MS: 275.

Method B

N-(2-Chloro-4-fluorosulphonylphenyl)-2-acetoxy-2-methylpropanamide

A solution of 2-chloro-4-fluorosulphonylaniline (2.5 g, 12 mmol), 2-acetoxyisobutyryl chloride (2.35 g, 14 mmol) and pyridine (1.2 ml, 14.5 mmol), in DCM (50 ml) was stirred at ambient temperature for 18 h. The mixture was washed with water, dried and evaporated to dryness. The residue was purified by column chromatography using 25% EtOAc/isohexane and the oily product, the title compound (2.0 g, 5.9 mmol), solidified on standing. MS: 336.

Method C

2-Chloro-4-(3-bromo-4-chloroanilinosulphonyl)aniline

A solution of N-acyl-2-chloro-4-chlorosulphonylaniline (370 mg, 1.38 mmol), 3-bromo-4-chloroaniline (250 mg, 1.2 mmol), 4-dimethylaminopyridine (10 mg) and pyridine (0.11 ml, 1.3 mmol) in DCM (10 ml) was stirred at ambient temperature for 4 h. The solution was washed with water and brine, dried and evaporated to dryness. The residue was dissolved in ethanol (25 ml) and 2M aqueous sodium hydroxide (5 ml) was added. The mixture heated at reflux for 4 h and then cooled to ambient temperature, evaporated to dryness and water (25 ml) was added to the residue. The aqueous solution was extracted with EtOAc; the separated organic phase was washed with water, dried and evaporated to dryness to yield the title compound (500 mg, 1.1 mmol). MS: 435.

Method D

2-Chloro-4-(4-methoxyanilinosulphonyl)aniline

A solution of N-acyl-2-chloro-4-chlorosulphonylaniline (536 mg, 2 mmol), 4-methoxyaniline (246 mg, 2 mmol), 4-dimethylaminopyridine (10 mg, 0.08 mmol) and pyridine (0.19 ml, 2.3 mmol) in DCM (25 ml) was stirred at ambient temperature for 4 h. The solution was washed with 1M aqueous hydrochloric acid and brine, dried and evaporated to dryness. The residue was dissolved in ethanol (25 ml) and 2M aqueous sodium hydroxide (5 ml) was added. The mixture heated at reflux for 4 h and then cooled to ambient temperature and evaporated to dryness. Water (25 ml) was added to the residue and the solution was neutralised to pH 7.0 by addition of 1M aqueous hydrochloric acid. The aqueous solution was extracted with EtOAc, the EtOAc extracts were washed with brine, dried and evaporated to dryness to yield the title compound (620 mg, 1.98 mmol). MS: 311.

Method E

2-Chloro-4-(allylaminosulphonyl)aniline

A solution of N-acyl-2-chloro-4-chlorosulphonylaniline (670 mg, 2.5 mmol) and allylamine (342 mg, 5.7 mmol), in DCM (25 ml) was stirred at ambient temperature for 4 h. The mixture was washed with 1M aqueous hydrochloric acid and brine, dried and evaporated to dryness. The residue was dissolved in ethanol (25 ml) and 2M aqueous sodium hydroxide (5 ml) was added. The mixture heated at reflux for 4 h and then cooled to ambient temperature and evaporated to dryness. Water (25 ml) was added to the residue and the solution was neutralised to pH 7.0 by addition of 1M aqueous hydrochloric acid. The aqueous solution was extracted with EtOAc. The EtOAc extracts were washed with brine, dried and evaporated to dryness to yield the title compound (550 mg, 2.2 mmol). MS: 245.

Method F

2-Chloro-4-(thien-2-ylmethylaminosulphonyl)aniline

A solution of N-acyl-2-chloro-4-chlorosulphonylaniline (320 mg, 1.2 mmol), 4-dimethylaminopyridine (10 mg, 0.08 mmol), pyridine (0.1 ml, 1.2 mmol) and 2-thiophenemethylamine (120 mg, 1.08 mmol) in DCM (8 ml) was stirred at ambient temperature for 18 h. The mixture was washed with 1M aqueous hydrochloric acid and then the organic phase was concentrated. The residue was dissolved in ethanol (7 ml), 2M aqueous sodium hydroxide (2 ml) was added and the mixture was heated at 60° C. for 6 h. The solvent was evaporated and the residue dissolved in EtOAc, washed with water, and the solvent phase was concentrated to yield the title compound which was used, without further purification.

Method G

2-Fluoro-4-(2-fluoroanilinosulphonyl)aniline

Method D was followed except that N-acyl-2-fluoro-4-chlorosulphonylaniline (Method H) was used in place of N-acyl-2-chloro-4-chlorosulphonylaniline, 2-fluoroaniline was used in place of 4-methoxyaniline and no 4-dimethylaminopyridine was used to yield the title compound.

Method H

N-Acyl-2-fluoro-4-chlorosulphonylaniline

N-acyl-2-fluoro-4-sulphoaniline tiethylamine salt (1:1) (Method I) (39 g, 0.12 mol) was added portion-wise, over 30 mins, to $POCl_3$ (60 ml) at 0° C. The reaction mixture was stirred at room temperature for 15 h and then poured slowly onto a stirred solution of ice-water. After stirring for 15 mins the mixture was filtered to yield the title compound as a solid (26 g, 0.10 mol). NMR (CDCl$_3$): 2.25 (s, 3H), 7.55 (br s, 1H), 7.7 (dd, 1H), 7.75–7.80 (m, 1H), 8.65 (t, 1H); MS: 190.

Method I

N-Acyl-2-fluoro-4-sulphoaniline Triethylamine Salt (1:1)

2-Fluoroaniline (40 g, 0.36 mol) was added dropwise to a stirred solution of concentrated sulphuric acid (60 ml) and the mixture heated to 190° C. for 15 h. The reaction mixture was then cooled to room temperature and poured slowly onto a stirred solution of ice-water. After stirring for 15 mins the mixture was filtered to yield a solid, 2-fluoro-4-sulphoaniline (41 g). NMR: 7.05 (t, 1H), 7.20–7.30 (m, 2H), 8.1 (br s, 3H); MS: 190 (M–H)$^-$. The 2-fluoro-4-sulphoaniline (41 g) was dissolved in acetic anhydride (70 ml) and stirred in an ice bath. Triethylamine (22 g, 0.22 mol) was added very slowly with vigorous stirring (and concomittant release of heat). The reaction mixture was left to stir for 14 h, at which point a solid formed; this was filtered to yield the title compound (39 g, 0.12 mol). MS: 232.

Method J

1-(t-Butoxycarbonyl)-4-(4-amino-3-methylbenzene)sulphonylpiperazinide

Method D was followed except that N-acyl-2-methyl-4-chlorosulphonylaniline (Method K) was used in place of N-acyl-2-chloro-4-chlorosulphonylaniline, 1-t-butyloxycarbonyl) piperazine was used in place of 4-methoxyaniline and no 4-dimethylaminopyridine was used to yield the title compound.

Method K

N-Acyl-2-methyl-4-chlorosulphonylaniline

N-Acyl-2-methyl-4-sulphoaniline triethylamine salt (1:1) (Method L) (35 g, 0.11 mol) was added portion-wise, over 30mins, to POCl$_3$ (50 ml) at 0° C. The reaction mixture was stirred at room temperature for 15 h and then poured slowly onto a stirred solution of ice-water. After stirring for 15 mins the mixture was filtered to yield the title compound as a solid (25 g, 0.10 mol). MS: 246.

Method L

N-Acyl-2-methyl-4-sulphoaniline Triethylamine Salt (1:1)

2-Methyl-4-sulphoaniline (30 g, 0.16 mol) was dissolved in acetic anhydride (50 ml) and stirred in an ice bath. Triethylamine (23 ml, 0.18 mol) was added very slowly with vigorous stirring (and concomittant release of heat). The reaction mixture was left to stir for 14 h, at which point a solid formed; this was filtered to yield the title compound (35 g, 0.11 mol). NMR: 1.15 (t, 9H), 2.05 (s, 3H), 2.45–2.50 (m, 1H), 3.1 (q, 6H), 7.25–7.40 (m, 2H), 7.85 (t, 1H), 9.7 (br s, 1H); MS: 228.

Method M

R-N-(2-Chloro-4-chlorosulphonylphenyl)-3,3,3-trifluoro-2-hydroxy-2-methylpropanamide R-N-(2-Chlorophenyl)-3,3,3-trifluoro-2-hydroxy-2-methylpropanamide (Method N) (13.8 g, 52 mmol) was added in portions to a cooled (0° C.) solution of chlorosulphonic acid (25 ml) over 15 mins and then the mixture was heated to 85° C. After 4.5 h the reaction mixture was cooled in an ice bath and then poured very slowly onto a stirred ice-water mixture. After stirring for 15 mins, the mixture was extracted with EtOAc (2×100 ml) and the combined organic layer washed with brine, dried and concentrated to yield a brown oil. This oil was purified by flash column chromatography using 10:1, iso-hexane: EtOAc to yield the title compound as a pale yellow solid (11 g, 30 mmol). NMR: 1.6 (s, 3H), 7.55 (dd, 1H), 7.6 (d, 1H), 7.95 (d, 1H), 9.7 (br s, 1H); MS: 364.

Method N

R-N-(2-Chlorophenyl)-3,3,3-trifluoro-2-hydroxy-2-methylpropanamide

Acetyl chloride (11.7 ml, 164 mmol) was added dropwise to a stirred solution of the R-3,3,3-trifluoro-2-hydroxy-2-methylpropanoic acid (10 g, 63 mmol) in toluene (100 ml) cooled in an ice bath. The mixture was then heated to 80° C. and the suspension dissolved to yield a clear solution. After 2 h the reaction mixture was cooled and then concentrated to yield a slight brown oil. This oil was then redissolved in DCM (140 ml) and DMF (4 drops) was added followed by oxalyl chloride (6 ml, 69 mmol). The solution bubbled vigorously and the reaction mixture was left to stir. After 15 h, this reaction mixture was added slowly to a stirred solution of 2-chloroaniline (8.7 g, 68 mmol) and pyridine (5.5 ml, 68 mmol) in DCM (150 ml). After 15 h stirring at room temperature, the resultant mixture was concentrated and the residue dissolved in methanol (500 ml). A solution of lithium hydroxide monohydrate (7.8 g, 0.19 mol) in water (120 ml) was then added and the mixture was stirred for 4 h. The mixture was then concentrated and the residue acidified to pH 2 (by addition of concentrated hydrochloric acid). EtOAc (150 ml) was added and the mixture washed with water (2×100 ml) and brine, dried and evaporated to dryness. The residue was purified by flash column chromatography using 6:1, iso-hexane: EtOAc to yield the title compound as a white solid (13.8 g, 52 mmol). NMR: 1.6 (s, 3H), 7.1–7.25 (m, 1H), 7.3–7.4 (m, 1H), 7.55 (dd, 1H), 7.8 (s, 1H), 8.0 (dd, 1H), 9.7 (br s, 1H); MS: 266.

Method O

R-N-[2-Chloro-4-(4-fluorosulphonylanilinosulphonyl)phenyl]-3,3,3-trifluoro-2-hydroxy-2-methylpropanamide A solution of R-N-(2-chloro-4-chlorosulphonylphenyl)-3,3,3-trifluoro-2-hydroxy-2-methylpropananide (Method M) (3.46 g, 9.45 mmol) in DCM (200 ml) was added to a stirred solution of 4-fluorosulphonylaniline (1.99 g, 11.3 mmol) and pyridine (1.52 ml, 18.2 mmol) in DCM (50 ml). The resultant mixture was stirred at ambient temperature overnight, evaporated to dryness and the residue treated with 1M aqueous hydrochloric acid (50 ml). The aqueous solution was extracted with EtOAc, the EtOAc extracts were washed with brine, dried and evaporated. The residue was purified by column chromatography using 30% EtOAc in DCM to yield the title compound as a foam (4.56 g, 9.05 mmol). NMR: 1.6 (s, 3H), 7.45 (d, 2H), 7.9 (dd, 1H), 8.0 (d, 1H), 8.05 (d, 2H), 8.3 (d, 1H); MS: 504.

Method P

S-3,3,3-Trifluoro-2-hydroxy-2-methylproanoylchloride

Oxalyl chloride (1.07 ml, 12 mmol) was added dropwise to a stirred suspension of (R)-(+)-2-hydroxy-2-methyl-3,3, 3-trifluoropropanoic acid (Method Q) (1.95 g, 12 mmol) in DCM (42 ml) and DMF (0.8 ml). The mixture was stirred at ambient temperature for 2–15 h to yield a solution of the title compound which was used in subsequent reactions without further purification.

Method Q

(R)-(+)-2-Hydroxy-2-methyl-3,3,3-trifluoropropanoic Acid

R/S-2-Hydroxy-2-methyl-3,3,3-trifluoropropanoic acid was resolved according to the resolution method described in European Patent Application No. EP 524781 (described for the preparation of the (S)-(−) acid except that (1S, 2R)-norephedrine was used in place of (1R, 2S)-norephedrine or (S)-(−)-1-phenylethylamine to yield the title compound, $[\alpha]_D^{20}$+18.1° (c, 8.8 in MeOH); NMR analysis of the acid in the presence of (R)(+)-1-phenylethylamine gave an enantiomerical purity of >98%. NMR (CDCl$_3$): 1.27 (s, 3H) for the (R)-enantiomer, 1.21 (s, 3H) for the (S)-enantiomer.

Method R

2-Chloro-4-[4-(2-hydroxyethylthio)anilinosulphonyl]aniline

A solution of 4-acetamidothiophenol (8.35 g, 50.0 mmol), ethylene carbonate (5.5 g, 62.5 mmol) and sodium ethoxide (4.1 g, 60.0 mmol) in ethanol (250 ml) was heated at reflux overnight and then cooled to ambient temperature and evaporated to dryness. The residue was dissolved in diethyl ether (500 ml), washed with 1M aqueous hydrochloric acid and brine, dried and evaporated to dryness. The residue was dissolved in ethanol (120 ml) and 2M aqueous sodium hydroxide (60 ml) was added. The mixture was heated at reflux overnight and then cooled to ambient temperature and evaporated to dryness. Water (25 ml) was added to the residue and the solution was neutralised to pH 7 by the addition of 1M aqueous hydrochloric acid. The aqueous solution was extracted with EtOAc, the EtOAc extracts were washed with brine, dried and evaporated to dryness. The residue was dissolved in DCM (100 ml) and added to a solution of 4-acetamido-3-chlorobenzenesulphonyl chloride (5.5 g, 20.5 mmol), 4-dimethylaminopyridine (50 mg, 0.4 mmol) and pyridine (5.0 ml, 60 mmol) in DCM (100 ml). The mixture was stirred at ambient temperature overnight, the solution was evaporated to dryness, the residue dissolved in diethyl ether (450 ml), washed with 1M aqueous hydrochloric acid and brine, dried and evaporated to dryness. The residue was dissolved in ethanol (100 ml) and 2M aqueous sodium hydroxide (25 ml) was added. The mixture was heated at reflux overnight and then cooled to ambient temperature and evaporated to dryness. Water (25 ml) was added to the residue and the solution was neutralised to pH 7 by the addition of 1M aqueous hydrochloric acid. The aqueous solution was extracted with EtOAc, the EtOAc extracts were washed with brine, dried and evaporated to dryness. The residue was purified by column chromatography using 25% EtOAc in DCM to yield the title compound (630 mg, 1.8 mmol). NMR: 2.9 (t, 2H), 3.5 (m, 2H), 4.8 (t, 1H), 6.2 (s, 2H), 6.75 (d, 1H), 7.0 (d, 2H), 7.2 (d, 2H), 7.3 (dd, 1H), 7.45 (d, 1H); MS: 357.

Method S

2-Chloro-4-[4-(2-ethoxyethylthio)anilinosulphonyl]aniline

A solution of 4-acetamidothiophenol (8.35 g, 50.0 mmol), ethylene carbonate (5.5 g, 62.5 mmol) and sodium ethoxide (4.1 g, 60.0 mmol) in ethanol (250 ml) was heated at reflux overnight and then cooled to ambient temperature and evaporated to dryness. The residue was dissolved in diethyl ether (500 ml), washed with 1M aqueous hydrochloric acid and brine, dried and evaporated to dryness. The residue was dissolved in ethanol (120 ml) and 2M aqueous sodium hydroxide (60 ml) was added. The mixture was heated at reflux overnight and then cooled to ambient temperature and evaporated to dryness. Water (25 ml) was added to the residue and the solution was neutralised to pH 7 by the addition of 1M aqueous hydrochloric acid. The aqueous solution was extracted with EtOAc, the EtOAc extracts were washed with brine, dried and evaporated to dryness. The residue was dissolved in DCM (100 ml) and added to a solution of 4-acetamido-3-chlorobenzenesulphonyl chloride (5.5 g, 20.5 mmol), 4-dimethylaminopyridine (50 mg, 0.4 mmol) and pyridine (5.0 ml, 60 mmol) in DCM (100 ml). The mixture was stirred at ambient temperature overnight, the solution was evaporated to dryness, the residue dissolved in diethyl ether (450 ml), washed with 1M aqueous hydrochloric acid and brine, dried and evaporated to dryness. The residue was dissolved in ethanol (100 ml) and 2M aqueous sodium hydroxide (25 ml) was added. The mixture was heated at reflux overnight and then cooled to ambient temperature and evaporated to dryness. Water (25 ml) was added to the residue and the solution was neutralised to pH 7 by the addition of 1M aqueous hydrochloric acid. The aqueous solution was extracted with EtOAc, the EtOAc extracts were washed with brine, dried and evaporated to dryness. The residue was purified by column chromatography using 10% EtOAc in DCM to yield the title compound (1.53 g, 3.96 mmol). NMR: 1.0 (t, 3H), 3.0 (t, 2H), 3.3–3.5 (m, 4H), 6.2 (s, 2H), 6.75 (d, 1H), 7.0 (d, 2H), 7.2 (d, 2H), 7.3 (dd, 1H), 7.45 (d, 1H); MS: 385.

Method T

2-Chloro-4-[4-(methoxycarbonyl)anilinosulphonyl]aniline

A solution of N-acyl-2-chloro-4-chlorosulphonylaniline (13.4 g, 50.0 mmol), methyl 4-aminobenzoate (7.55 g, 50.0 mmol), 4-dimethylaminopyridine (100 mg, 0.8 mmol) and pyridine (5.0 ml, 60 mmol) in DCM (350 ml) was stirred at ambient temperature for 4 h. The solution was evaporated to dryness, the residue dissolved in EtOAc (1.0 L), washed with 1M aqueous hydrochloric acid and brine, dried and evaporated to dryness. The residue was dissolved in ethanol (600 ml) and 2M aqueous sodium hydroxide (137 ml) was added. The mixture was heated at reflux for 4 h and then cooled to ambient temperature and evaporated to dryness. Water (25 ml) was added to the residue and the solution was acidified to pH 1 by the addition of concentrated aqueous hydrochloric acid. The solution was evaporated to dryness, the residue dissolved in methanol (200 ml), the solution cooled to −35° C. and treated with thionyl chloride (18.0 ml). The mixture was stirred at ambient temperature overnight and evaporated to dryness. The residue was dissolved in saturated sodium hydrogen carbonate solution, the aqueous solution was extracted with EtOAc, the EtOAc extracts were washed with brine, dried and evaporated to dryness to yield the title compound (13.6 g, 40.0 mmol); MS: 339.

Method U

2-Chloro-4-[1-(t-butoxycarbonyl)piperazin-4-ylsulphonyl]aniline

A solution of N-acyl-2-chloro-4-chlorosulphonylaniline (10.0 g, 37.3 mmol), 1-(t butoxycarbonyl)piperazine (7.0 g, 37.6 mmol) and triethylamine (7.77 ml, 56.4 mmol) in DCM (150 ml) was stirred at ambient temperature for 4 h. The solution was evaporated to dryness, the residue dissolved in EtOAc (150 ml), washed with 0.7M aqueous citric acid, saturated aqueous sodium hydrogen carbonate solution and brine, dried and evaporated to dryness. The residue was dissolved in ethanol (100 ml) and 2M aqueous sodium hydroxide (87.5 ml) was added. The mixture was heated at reflux overnight and then cooled to ambient temperature and evaporated to dryness. Water (75 ml) was added to the residue and the mixture was filtered, the solid washed with water, dried and crystallised from EtOAc to yield the title compound as a solid (11.4 g, 30.3 mmol); M.pt. 243–244° C. NMR: 1.35 (s, 9H), 2.8 (m, 4H), 3.4 (m, 4H), 6.35 (s, 2H), 6.9 (d, 1H), 7.35 (dd, 1H), 7.5 (d, 1H); MS: 374.

Method V 2-(4-Aminophenyl)-1,3-dioxolane

To a mixture of 4-nitrobenzaldehyde (7.55 g, 50 mmol) and ethyleneglycol (4.65 g, 75.0 mmol) in toluene (125 ml) was added 4-toluenesulphonic acid (100 mg, 0.5 mmol) and the mixture heated under reflux using a Dean-Stark water separator for 2 h. The solution was evaporated to dryness, the residue dissolved in EtOAc (125 ml), washed with saturated sodium hydrogen carbonate solution, dried and evaporated to dryness. The residue was dissolved in ethanol (200 ml) and hydrogenated over 10% Pd/C for 4 h at ambient temperature. The catalyst was removed by filtration, the ethanol evaporated to yield the title compound which was used without further purification.

Method W 4-(2-Hydroxyethylamino)aniline

A mixture of ethanolamine (2.29 g, 37.5 mmol) and 1-fluoro-4-nitrobenzene (3.53 g, 25.0 mmol) in dimethylsulphoxide (25 ml) was treated with potassium carbonate (6.9 g, 50 mmol) and heated at 90° C. overnight. The mixture was cooled and poured onto water (250 ml), the precipitated solid filtered off, dried, dissolved in ethanol (50 ml) and hydrogenated over 10% Pd/C for 4 h at ambient temperature . The catalyst was removed by filtration, the ethanol evaporated and the residue purified by column chromatography using EtOAc to yield the title compound (740 mg, 5.0 mmol). NMR: 2.95 (t, 2H), 3.5 (t, 2H), 4.1 (s, 2H), 4.4 (s, 1H), 4.55 (t, 1H), 6.4 (m, 4H); MS: 153 (M+H)+.

Method X 4-(N-2-Tetrahydropyranyloxyethyl-t-butoxycarbonylamino)aniline

To a mixture of N-t-butoxycarbonylethanolamine (7.7 ml, 50 mmol) and 3,4-dihydropyran (5.7 ml, 62.5 mmol) in DCM (125 ml) was added 4-toluenesulphonic acid (100 mg, 0.5 mmol) and the mixture stirred at ambient temperature for 3 h. The solution was washed with saturated sodium hydrogen carbonate solution, dried and evaporated to dryness. The residue was filtered through a short pad of basic alumina with 10% EtOAc in hexane, the solvent evaporated to dryness, the residue dissolved in dimethylacetamide (5 ml) and added to a suspension of sodium hydride (400 mg of 50% dispersion in mineral oil, 10 mmol) in dimethylacetamide (5 ml). The mixture was heated at 50° C. for 1 h, cooled to ambient temperature and added to a solution of 1-fluoro-4-nitrobenzene (1.06 g, 7.5 mmol) in dimethylacetamide (5 ml) and heated at 50° C. for 4 h. The cooled mixture was poured onto water (150 ml), the aqueous solution was extracted with EtOAc, the EtOAc extracts were washed with brine, dried and evaporated. The residue was dissolved in ethanol (50 ml) and hydrogenated over 10% Pd/C for 4 h at ambient temperature. The catalyst was removed by filtration, the ethanol evaporated and the residue purified by column chromatography using 30% EtOAc in hexane to yield the title compound (640 mg, 1.9 mmol). NMR: 1.2–1.6 (m, 15H), 3.4–3.8 (m, 6H), 6.6 (d, 2H), 7.0 (d, 2H(; MS: 337 (M+H)+.

Method Y

R-N-(2-Chloro-4-chlorosulphonylphenyl)-3,3,3-trifluoro-2-hydroxy-2-methylpropanamide R-N-(2-chlorophenyl)-3,3,3-trifluoro-2-hydroxy-2-methylpropanamide (Method Z) (4.71 g, 17.6 mmol) was added portion wise to a cooled (ice bath) and stirred solution of chlorosulphonic acid (9 ml). The resulting mixture was heated to 85° C. for 270 mins. The reaction mixture was then cooled to room temperature and poured onto an ice/water slurry. The resulting aqueous mixture was extracted with EtOAc. The combined extracts were washed with brine, dried and were concentrated to yield an oil. Purification by column chromatography yielded the title compound as a solid (4.03 g, 11.0 mmol). NMR (CDCl$_3$): 1.80 (s, 3H), 3.46 (s, 1H), 8.00 (dd, 1H), 8.10 (d, 1H), 8.77 (d, 1H), 9.44 (s, 1H); MS: 364.

Method Z

R-N-(2-Chlorophenyl)-3,3,3-trifluoro-2-hydroxy-2-methylpropanamide

2-Chloroaniline (3.2 ml) and 2,6-di-t-butylpyridine (7.4 ml) were added to a solution of S-3,3,3,-trifluoro-2-hydroxy-2-methylpropanoyl chloride [produced in situ by reaction of R-3,3,3,-trifluoro-2-hydroxy-2-methylpropanoic acid (4.74 g, 30 mmol) with 2M oxalyl chloride (16.5 ml, 33 mmol) in DCM (50 ml)] in DCM. The resulting solution was stirred for 20 h at room temperature. The reaction mixture was then washed with water, brine, dried, evaporated and purified by column chromatography to yield the title compound as a solid (4.76 g, 17.8 mmol). NMR: 1.60 (s, 3H), 7.25 (t, 1H), 7.38 (t, 1H), 7.55 (d, 1H), 7.80 (s, 1H), 8.00 (d, 1H), 9.70 (s, 1H); MS: 266.

Method A1

2-Chloro-4-[(4-sulphamoyl-anilino)sulphonyl]aniline

A solution of 4-acetamido-3-chlorobenzenesulphonyl chloride (2.68 g, 10.0 mmol), sulphanilamide (2.06 g, 12.0 mmol), dimethylaminopyridine (1.22 g, 10.0 mmol) and pyridine (2.40 ml, 10.0 mmol) in EtOAc (150 ml) was stirred at ambient temperature for 3 days. The solution was washed with 1.0M aqueous hydrochloric acid and brine, dried and evaporated to dryness. The residue was dissolved in ethanol (100 ml) and 2M aqueous sodium hydroxide (22.1 ml) was added. The mixture was heated at reflux for 4 hours and then cooled to ambient temperature and evaporated to dryness. Water (25 ml) was added to the residue and the solution was neutralised to pH 7.0 by the addition of 1M aqueous hydrochloric acid. The aqueous solution was extracted with EtOAc, the EtOAc extracts washed with brine, dried and evaporated to give, as a solid, the title compound (2.34 g, 6.5 mmol). M.p. 197°–198°; NMR: 6.3 (s, 2H), 6.8 (d, 1H), 7.2 (s, 2H), 7.25 (d, 2H), 7.4 (dd, 2H), 7.55 (d, 1H), 7.65 (d, 2H); MS: 360.

Method B1

2-Chloro-5-(2-chloroanilino-sulphonyl)aniline

A solution of 3-nitro-4-chlorobenzenesulphonyl chloride (768 mg, 3.0 mmol), 2-chloroaniline (383 mg, 3.0 mmol), 4-dimethylaminopyridine (10 mg, 0.08 mmol) and pyridine (0.30 ml, 3.6 mmol) in DCM (35 ml) was stirred at ambient temperature overnight. The solution was evaporated to dryness, the residue dissolved in EtOAc and washed with 1.0 M aqueous hydrochloric acid and brine, dried and evaporated to dryness. The residue was dissolved in EtOAc (30 ml) and hydrogenated over 10% Pd/C for 4 h at ambient temperature. The catalyst was removed by filtration and the EtOAc evaporated to dryness. The residue was purified by column chromatography on basic alumina using 5% methanol in EtOAc to give, as a solid, the title compound (140 mg, 0.44 mmol). MS: 315.

Method C1

R-3,3,3-Trifluoro-2-hydroxy-2-methylpropanoylchloride

Oxalyl chloride (1.07 ml, 12 mmol) was added dropwise to a stirred suspension of (S)-(−)-2-hydroxy-2-methyl-3,3,3-trifluoropropanoic acid (Method D1) (1.95 g, 12 mmol) in DCM (42 ml) and DMF (0.8 ml). The mixture was stirred at ambient temperature for 2–15 h to yield a solution of the title compound which was used in subsequent reactions without further purification.

Method D1

(S)-(−)-2-Hydroxy-2-methyl-3,3,3-trifluoropropanoic Acid

R/S-2-Hydroxy-2-methyl-3,3,3-trifluoropropanoic acid was resolved according to the resolution method described in European Patent Application No. EP 524781 to yield the title compound, $[\alpha]_D^{20}$ −18.6° (c, 8.8 in MeOH).

Method E1

R/S-3,3,3-Trifluoro-2-hydroxy-2-methylpropanoylchloride

Oxalyl chloride (1.07 ml, 12 mmol) was added dropwise to a stirred suspension of R/S-2-hydroxy-2-methyl-3,3,3-trifluoropropanoic acid (1.95 g, 12 mmol) in DCM (42 ml) and DMF (0.8 ml). The mixture was stirred at ambient temperature for 2–15 h to yield a solution of the title compound which was used in subsequent reactions without further purification.

Example 273

The following illustrate representative pharmaceutical dosage forms containing the compound of formula I, or a pharmaceutically acceptable salt or an in vivo hydrolysable ester thereof (hereafter compound X), for therapeutic or prophylactic use in humans:

| Tablet I | mg/tablet |
|---|---|
| Compound X | 100 |
| Lactose Ph.Eur. | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound X | 50 |
| Lactose Ph.Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound X | 1.0 |
| Lactose Ph.Eur. | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound X | 10 |
| Lactose Ph.Eur. | 488.5 |
| Magnesium stearate | 1.5 |

| Injection I | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection to 100% | |

| Injection II | 10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |

| Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

What is claimed is:

1. A compound of the formula (I):

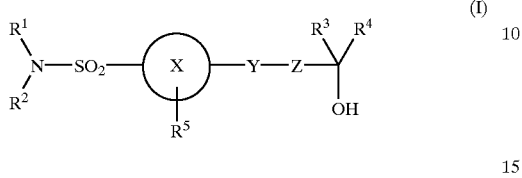

wherein:

Ring X is phenyl;

$R^1$ and $R^2$ are independently as defined in (a) or (b);

$R^3$ and $R^4$ are as defined in (c) or (d);

$R^5$ is as defined in (e) or (f);

Y—Z is as defined in (g) or (h)

wherein:

(a) either $R^1$ and $R^2$ are each selected independently from hydrogen, $C_{1-3}$alkyl, pyridyl and phenyl which is unsubstituted or substituted by one or two substituents selected independently from $C_{1-4}$alkyl, $C_{1-4}$alkoxy, $C_{2-4}$alkenyloxy, hydroxy, halo and cyano, or $R^1$ and $R^2$ together with the nitrogen atom to which they are attached form morpholino, thiomorpholino, piperidinyl, pyrrolidinyl or imidazolyl;

(b) either $R^1$ and $R^2$ are each selected independently from phenyl substituted by one or more P (wherein P is as defined hereinbelow), phenyl substituted by one or more groups selected from $C_{1-4}$alkyl, $C_{1-4}$alkoxy, $C_{2-4}$alkenyloxy, hydroxy, halo and cyano and additionally substituted by one or more groups selected from P, a heterocyclic group other than unsubstituted pyridyl which is optionally substituted on a ring carbon by one or more Q (wherein Q is as defined hereinbelow) and wherein if said heterocyclic group contains an —NH— moiety that nitrogen may be optionally substituted by a group selected from D (wherein D is as defined hereinbelow), naphthyl optionally substituted by one or more Q, $C_{4-6}$alkyl, $C_{3-6}$cycloalkyl optionally substituted with one or more Q, $C_{2-6}$alkenyl, $C_{2-6}$alkynyl, $C_{1-6}$alkyl substituted by one or more V (wherein V is as defined hereinbelow), $R^6$T— (wherein $R^6$ and T are as defined hereinbelow) and $R^7C_{1-6}$alkylT— (where $R^7$ is as defined hereinbelow), or $R^1$ and $R^2$ together with the nitrogen atom to which they are attached form a heterocyclic group other than unsubstituted morpholino, unsubstituted thiomorpholino, unsubstituted piperidinyl, unsubstituted pyrrolidinyl or unsubstituted imidazolyl which is optionally substituted on a ring carbon by one or more Q (wherein Q is as defined hereinbelow) and wherein if said heterocyclic group contains an —NH— moiety that nitrogen may be optionally substituted by a group selected from D (wherein D is as defined hereinbelow);

(c) either $R^3$ and $R^4$ are independently $C_k$alkyl optionally substituted by from 1 to 2k+1 atoms selected from fluoro and chloro wherein k is 1–3, provided that $R^3$ and $R^4$ are not both methyl;

or $R^3$ and $R^4$ together with the carbon atom to which they are attached, form a $C_m$cycloalkyl ring optionally substituted by from 1 to 2m–2 fluorine atoms wherein m is 3–5;

(d) $R^3$ and $R^4$ are both methyl;

(e) $R^5$ is $C_{1-4}$alkyl, haloC$_{1-4}$alkyl, $C_{1-4}$alkoxy, haloC$_{1-4}$alkoxy, cyano, nitro, $C_{2-4}$alkenyloxy or trifluoromethylthio;

(f) $R^5$ is halo, hydroxy, amino, $C_{1-6}$alkylamino, ($C_{1-6}$alkyl)$_2$amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl(N—$C_{1-6}$alkyl)amino, thiol, $C_{1-6}$alkylsulphanyl, $C_{1-6}$alkylsulphinyl, $C_{1-6}$alkylsulphonyl, sulphamoyl, N-($C_{1-6}$alkyl)aminosulphonyl, N-($C_{1-66}$alkyl)$_2$aminosulphonyl, carboxy, carbamoyl, N-($C_{1-6}$alkyl)carbamoyl, N-($C_{1-6}$alkyl)$_2$carbamoyl, $C_{1-6}$alkoxycarbonyl, formyl, $C_{1-6}$alkanoyl, $C_{2-6}$alkenyl, $C_{2-6}$alkynyl, $C_{5-6}$alkyl, haloC$_{5-6}$alkyl, $C_{5-6}$alkoxy, haloC$_{5-6}$alkoxy or $C_{5-6}$alkenyloxy;

(g) Y—Z is —NHC(O)—, —OCH$_2$—, —SCH$_2$—, —NHCH$_2$— or trans-vinylene;

(h) Y—Z is —NHC(S)—;

$R^6$ is selected from $C_{1-6}$alkyl (optionally substituted with one or more $R^8$), $C_{3-6}$cycloalkyl optionally substituted with one or more $R^8$, a heterocyclic group optionally substituted on a ring carbon by one or more $R^8$ and if said heterocyclic group contains an —NH— moiety that nitrogen may be optionally substituted by a group selected from D (wherein D is as defined hereinbelow), phenyl optionally substituted by one or more $R^8$, naphthyl optionally substituted by one or more $R^8$;

$R^7$ is a heterocyclic group optionally substituted on a ring carbon by one or more $R^8$ and if said heterocyclic group contains an —NH— moiety that nitrogen may be optionally substituted by a group selected from D (wherein D is as defined hereinbelow), phenyl optionally substituted by one or more $R^8$, naphthyl optionally substituted by one or more $R^8$;

$R^8$ is trifluoromethyl, $C_{1-6}$alkyl, halo, hydroxy, trifluoromethoxy, cyano, $C_{1-6}$alkoxy, formyl, $C_{1-6}$alkanoyl, $C_{1-6}$alkanoyloxy, amino, $C_{1-6}$alkylamino, ($C_{1-6}$alkyl)$_2$amino, $C_{1-6}$alkanoylamino, $C_{1-6}$alkanoyl(N—$C_{1-6}$alkyl)amino, nitro, carboxy, carbamoyl, $C_{1-6}$alkoxycarbonyl, thiol, $C_{1-6}$alkylsulphanyl, $C_{1-6}$alkylsulphinyl, $C_{1-6}$alkylsulphonyl, sulphamoyl, N-($C_{1-6}$alkyl)aminosulphonyl, N-($C_{1-6}$alkyl)$_2$aminosulphonyl, carbamoylC$_{1-6}$alkyl, N-($C_{1-6}$alkyl)carbamoylC$_{1-6}$alkyl, N-($C_{1-6}$alkyl)$_2$carbamoyl-C$_{1-6}$alkyl, hydroxyC$_{1-6}$alkyl, $C_{1-6}$alkoxyC$_{16}$alkyl, phenylC$_{1-6}$alkyl or phenylC$_{1-6}$alkoxy;

P is selected from $C_{2-6}$alkyl-M— substituted with one or more $R^9$, $C_{2-6}$alkenyl-M— optionally substituted with one or more $R^9$, $C_{2-6}$alkynyl-M— optionally substituted with one or more $R^9$ (with the proviso that in the three previous groups $R^9$ is not a substituent on the carbon atom attached to M), $R^{10}$—CH$_2$—M—, $R^{11}$—M—, thiol, $C_{1-6}$alkylsulphanyl, $C_{1-6}$alkylsulphinyl, $C_{1-6}$alkylsulphonyl, sulphamoyl, nitro, carboxy, $C_{1-6}$alkoxycarbonyl, amino, $C_{1-6}$alkylamino, ($C_{1-6}$alkyl)$_2$amino, carbamoyl, N-($C_{1-6}$alkyl)carbamoyl, N-($C_{1-6}$alkyl)$_2$carbamoyl, $C_{1-6}$alkanoylamino, $C_{1-6}$alkanoyl(N—$C_{1-6}$alkyl)amino, trifluoromethyl, trifluoromethoxy, formyl, $C_{1-6}$alkanoyl, $C_{5-6}$alkyl, $C_{2-6}$alkenyl, $C_{2-6}$alkynyl N-($C_{1-6}$alkyl)aminosulphonyl, hydroxymethyl, hydroxyacetyl, N-($C_{1-6}$alkyl)$_2$aminosulphonyl, $C_{1-6}$alkanoylaminosulphonyl, $C_{1-6}$alkanoyl(N—$C_{1-6}$alkyl)aminosulphonyl, $C_{1-6}$alkylsulphonylaminocarbonyl, $C_{1-6}$alkylsulphonyl(N—$C_{1-6}$alkyl)aminocarbonyl, $C_{5-6}$alkoxy, $C_{5-6}$alkenyloxy, phenyl optionally substituted by one or more $R^8$, naphthyl optionally substituted by one or more $R^8$ and a heterocyclic group optionally substituted on a ring carbon by one or more $R^8$ and if said heterocyclic group contains an —NH— moiety that nitrogen may be optionally substituted by a group selected from D (wherein D is as defined hereinbelow);

Q is selected from any of the values defined for P, $C_{1-4}$alkyl, $C_{1-4}$alkoxy, $C_{2-4}$alkenyloxy, hydroxy, halo and cyano;

V is selected from any of the values defined for Q, phenyl optionally substituted by one or more Q, naphthyl optionally substituted by one or more Q, a heterocyclic group optionally substituted on a ring carbon by one or more Q and if said heterocyclic group contains an —NH— moiety that nitrogen may be optionally substituted by a group selected from D (wherein D is as defined hereinbelow) and $C_{3-6}$cycloalkyl optionally substituted with one or more Q;

T is selected from —O—, —C(O)—, —NH—, —N(N—$C_{1-6}$alkyl)—, —C(O)NH—, —NHC(O)—, —C(O)N(N—$C_{1-6}$alkyl)—, —N(N—$C_{1-6}$alkyl)C(O)—, —SO$_2$—, —C(S)—, —C(S)NH—, —NHC(S)—, —C(S)N(N—$C_{1-6}$alkyl)— and —N(N—$C_{1-6}$alkyl)C(S)—;

M is selected from —O—, —N($R^{12}$)—, —C(O)—, —N($R^{12}$)C(O)—, —C(O)N($R^{12}$)—, —S(Q)$_n$—, —OC(O)—, —C(O)O—, —N($R^{12}$)C(O)O—, —OC(O)N($R^{12}$)—, —C(S)N($R^{12}$)—, —N($R^{12}$)C(S)—, —SO$_2$N($R^{12}$)—, —N($R^{12}$)SO$_2$—, —N($R^{12}$)C(O)N($R^{12}$)—, —N($R^{12}$)C(S)N($R^{12}$)—, —SO$_2$NHC(O)—, —SO$_2$N($R^{12}$)C(O)—, —C(O)NHSO$_2$— and —C(O)N($R^{12}$)SO$_2$—, or M is a direct bond;

D is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)$_2$carbamoyl, benzoyl, (heterocyclic group)carbonyl, phenylsulphonyl, (heterocyclic group)sulphonyl, phenyl and a carbon linked heterocyclic group, and wherein any $C_{1-6}$alkyl group may be optionally substituted by one or more $R^9$, and wherein any phenyl or heterocyclic group may be optionally substituted on a ring carbon by one or more groups selected from $R^8$ and if a heterocyclic group contains an —NH— moiety that nitrogen may be optionally substituted by a group selected from E;

E is selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)$_2$carbamoyl, $C_{1-6}$alkoxy$C_{1-6}$alkanoyl, phenyl$C_{1-6}$alkyl, benzoyl, phenyl$C_{1-6}$alkanoyl, phenyl$C_{1-6}$alkoxycarbonyl and phenylsulphonyl;

$R^9$ is selected from hydroxy, amino, $C_{1-6}$alkylamino, ($C_{1-6}$alkyl)$_2$amino, carboxy, $C_{1-6}$alkoxy, carbamoyl, N-($C_{1-6}$alkyl)carbamoyl, N-($C_{1-6}$alkyl)$_2$carbamoyl, formyl, sulphamoyl, N—$C_{1-6}$alkylaminosulphonyl, N-($C_{1-6}$alkyl)$_2$aminosulphonyl, $C_{1-6}$alkylsulphonylamino, $C_{1-6}$alkanoylamino, a heterocyclic group optionally substituted on a ring carbon by one or more $R^8$ and if said heterocyclic group contains an —NH— moiety that nitrogen may be optionally substituted by a group selected from D (wherein D is as defined hereinabove), phenyl optionally substituted by one or more $R^8$, naphthyl optionally substituted by one or more $R^8$, $C_{1-6}$alkylsulphanyl, $C_{1-6}$alkylsulphinyl and $C_{1-6}$alkylsulphonyl;

$R^{10}$ is carboxy, carbamoyl, N-($C_{1-6}$alkyl)carbamoyl, N-($C_{1-6}$alkyl)$_2$carbamoyl, sulphamoyl, N-($C_{1-6}$alkyl)aminosulphonyl, N-($C_{1-6}$alkyl)$_2$aminosulphonyl, $C_{1-6}$alkylsulphanyl, $C_{1-6}$alkylsulphinyl, $C_{1-6}$alkylsulphonyl, $C_{1-6}$alkoxycarbonyl, $C_{1-6}$alkanoylamino, a heterocyclic group optionally substituted on a ring carbon by one or more $R^8$ and if said heterocyclic group contains an —NH— moiety that nitrogen may be optionally substituted by a group selected from D (wherein D is as defined hereinabove), phenyl optionally substituted by one or more $R^8$ or naphthyl optionally substituted by one or more $R^8$;

$R^{11}$ is a heterocyclic group optionally substituted on a ring carbon by one or more $R^8$ and if said heterocyclic group contains an —NH— moiety that nitrogen may be optionally substituted by a group selected from D (wherein D is as defined hereinabove), phenyl optionally substituted by one or more $R^8$, $C_{3-6}$cycloalkyl optionally substituted by one or more $R^8$, or naphthyl optionally substituted by one or more $R^8$;

$R^{12}$ is hydrogen or $C_{1-6}$alkyl optionally substituted with $R^{13}$ with the proviso that $R^{13}$ is not a substituent on the carbon attached to the nitrogen atom of M;

$R^{13}$ is halo, hydroxy, amino, cyano, nitro, trifluoromethyl, trifluoromethoxy, $C_{1-6}$alkyl, $C_{2-6}$alkenyl, $C_{2-6}$alkynyl, $C_{1-6}$alkylamino, ($C_{1-6}$alkyl)$_2$amino, $C_{1-6}$alkanoylamino, $C_{1-6}$alkanoyl(N—$C_{1-6}$alkyl)amino, $C_{1-6}$alkylsulphonylamino, $C_{1-6}$alkylsulphonyl(N—$C_{1-6}$alkyl)amino, thiol, $C_{1-6}$alkylsulphanyl, $C_{1-6}$alkylsulphinyl, $C_{1-6}$alkylsulphonyl, sulphamoyl, N-($C_{1-6}$alkyl)aminosulphonyl, N-($C_{1-6}$alkyl)$_2$aminosulphonyl, carboxy, carbamoyl, N-($C_{1-6}$alkyl)carbamoyl, N-($C_{1-6}$alkyl)$_2$carbamoyl, $C_{1-6}$alkoxycarbonyl, $C_{1-6}$alkanoyl or formyl;

n is 0–2; and wherein a heterocyclic group is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —CH$_2$— group can optionally be replaced by a —C(O)—, a ring nitrogen atom may optionally bear a $C_{1-6}$alkyl group and form a quaternary compound or a ring nitrogen and/or sulphur atom may be optionally oxidised to form the N-oxide and or the S-oxides;

with the proviso that where $R^1$ and $R^2$ are both as defined in (a), $R^3$ and $R^4$ are both as defined in (c), $R^5$ is as defined in (e) and Ring X is phenyl, then Y—Z must be —NHC(S)—;

or a pharmaceutically acceptable salt thereof, and provided said compound is not 4-(3-hydroxy-3-methyl-1-butynyl)-N-(3-methyl-2-pyridinyl)-benzenesulphonamide, N-{4-[N,N-bis-(sec-butyl)aminosulphonyl]phenyl}-2-hydroxy-2-methyl-3,3,3-trifluoropropanamide or N-{4-[N,N-bis-(iso-butyl)aminosulphonyl]phenyl}-2-hydroxy-2-methyl-3,3,3-trifluoropropanamide.

2. A compound of the formula (I) as claimed in claim 1 wherein $R^3$ and $R^4$ are independently $C_k$alkyl optionally substituted by from 1 to 2k+1 atoms selected from fluoro and chloro wherein k is 1–3.

3. A compound of the formula (I) as claimed in claim 1 or 2 wherein one of $R^3$ and $R^4$ is methyl and the other is trifluoromethyl.

4. A compound of the formula (I) as claimed in claim 1 or 2 wherein $R^5$ is selected from halo, nitro, $C_{1-4}$alkyl, $C_{1-4}$alkoxy, $C_{2-4}$alkenyl; $C_{2-4}$alkynyl, hydroxy, hydrogen, amino, carboxy and sulphamoyl.

5. A compound of the formula (I) as claimed in claim 1 or 2 wherein $R^5$ is selected from fluoro and chloro.

6. A compound of the formula (I) as claimed in claim 1 or 2 wherein Y—Z is —NHC(O)—.

7. A compound of the formula (I) as claimed in claim 1 or 2 wherein $R^1$ and $R^2$ are each independently selected from hydrogen, methyl, cyclopropyl, 4-hydroxycyclohexyl, 2-hydroxyethyl, 2-hydroxypropyl, 2,3-dihydroxypropyl, 4-(morpholinosulphonyl)phenyl, pyrid-3-yl, 2-carbamoylthien-3-yl, 2-chloropyrid-3-yl, 5-chloropyrid-2-yl, 5-methylpyrid-2-yl, pyrimid-2-yl, 4,6-dimethylpyrimid-2-yl or 5,6-dimethylpyrazin-2-yl;

or $R^1$ and $R^2$ together with the nitrogen atom to which they are attached form 4-hydroxypiperidinyl or 1-(hydroxyacetyl)piperazin-4-yl.

8. A compound of formula (Ib):

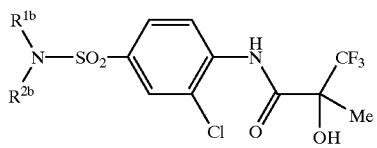

(Ib)

wherein $R^{1b}$ and $R^{2b}$ are independently selected from:
i) hydrogen;
ii) $C_{1-6}$alkyl or $C_{3-6}$cycloalkyl optionally substituted with one or more $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, $C_{1-6}$alkoxycarbonyl, amino, $C_{1-6}$alkylamino, $(C_{1-6}$alkyl$)_2$amino, carbamoyl, N-$(C_{1-6}$alkyl$)$carbamoyl, N-$(C_{1-6}$alkyl$)_2$carbamoyl, $C_{1-6}$alkanoylamino, $C_{1-6}$alkanoyl(N—$C_{1-6}$alkyl)amino, $C_{1-6}$alkanoyl, $C_{2-6}$alkenyl, $C_{2-6}$alkynyl, N-$(C_{1-6}$alkyl)aminosulphonyl, hydroxymethyl, hydroxyacetyl or N-$(C_{1-6}$alkyl$)_2$aminosulphonyl;
iii) a heterocyclic group selected from pyridyl, pyrimidyl, pyridazinyl or pyrazinyl, wherein said heterocyclic group is optionally substituted with one or more $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, C1–6alkoxycarbonyl, amino, $C_{1-6}$alkylamino, $(C_{1-6}$alkyl$)_2$amino, carbamoyl, N-$(C_{1-6}$alkyl$)$carbamoyl, N-$(C_{1-6}$alkyl$)_2$carbamoyl, $C_{1-6}$alkanoylamino, $C_{1-6}$alkanoyl(N—$C_{1-6}$alkyl)amino, trifluoromethyl, trifluoromethoxy, $C_{1-6}$alkanoyl, $C_{2-6}$alkenyl, $C_{2-6}$alkynyl, N-$(C_{1-6}$alkyl)aminosulphonyl, hydroxymethyl, hydroxyacetyl or N-$(C_{1-6}$alkyl$)_2$aminosulphonyl;

or $R^{1b}$ and $R^{2b}$ together with the nitrogen atom to which they are attached form piperidinyl or piperazinyl; wherein said piperidinyl and piperazinyl may be optionally substituted on a ring carbon by one or more groups selected from $C_{1-6}$alkyl, $C_{1-6}$alkoxy, $C_{2-6}$alkenyloxy, hydroxy, halo, cyano, $C_{1-6}$alkylsulphanyl, $C_{1-6}$alkylsulphinyl, $C_{1-6}$alkylsulphonyl, sulphamoyl, carboxy, $C_{1-6}$alkoxycarbonyl, amino, $C_{1-6}$alkylamino, $(C_{1-6}$alkyl$)_2$amino, carbamoyl, N-$(C_{1-6}$alkyl$)$carbamoyl, N-$(C_{1-6}$alkyl$)_2$carbamoyl, $C_{1-6}$alkanoylamino, $C_{1-6}$alkanoyl(N—$C_{1-6}$alkyl)amino, $C_{1-6}$alkanoyl, $C_{2-6}$alkenyl, $C_{2-6}$alkynyl, N-$(C_{1-6}$alkyl)aminosulphonyl, hydroxymethyl, hydroxyacetyl or N-$(C_{1-6}$alkyl$)_2$aminosulphonyl; and said piperazinyl may be optionally substituted on the ring nitrogen by a group selected from $C_{1-6}$alkanoyl, $C_{1-6}$alkylsulphonyl, $C_{1-6}$alkoxycarbonyl, carbamoyl, N-$(C_{1-6}$alkyl)carbamoyl and N,N-$(C_{1-6}$alkyl$)_2$carbamoyl; and wherein any $C_{1-6}$alkyl group may be optionally substituted by one or more groups selected from hydroxy, amino, $C_{1-6}$alkylamino, $(C_{1-6}$alkyl$)_2$amino, carboxy, $C_{1-6}$alkoxy, carbamoyl, N-$(C_{1-6}$alkyl)carbamoyl, N-$(C_{1-6}$alkyl$)_2$carbamoyl, sulphamoyl, N—$C_{1-6}$alkylaminosulphonyl, N-$(C_{1-6}$alkyl$)_2$aminosulphonyl, $C_{1-6}$alkylsulphonylamino, $C_{1-6}$alkanoylamino, $C_{1-6}$alkylsulphanyl, $C_{1-6}$alkylsulphinyl and $C_{1-6}$alkylsulphonyl, and pharmaceutically acceptable salts thereof.

9. A pharmaceutical composition which comprises a compound of the formula (I) or (Ib) as claimed in claim 1 or 8 a pharmaceutically acceptable salt thereof, in association with a pharmaceutically acceptable excipient or carrier.

10. A process for preparing a compound of formula (I) as claimed in claim 1 or a pharmaceutically acceptable salt thereof, which process comprises:

reacting a compound of formula (XI):

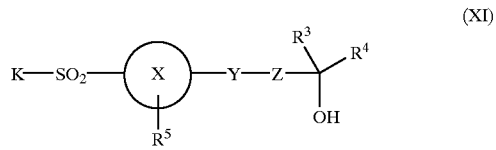

(XI)

where K is a leaving atom or group, and in which Y—Z is $OCH_2$, $SCH_2$ or $NHCH_2$ or —NHC(O)— with an amine of formula $R^1R^2NH$; and thereafter if necessary:
i) converting a compound of the formula (I) into another compound of the formula (I);
ii) removing any protecting groups; or
iii) forming a pharmaceutically acceptable salt.

11. A method of treating diabetes mellitus in a warm blooded animal in need thereof comprising administering to said animal an effective amount of a compound of formula (I) or (Ib) as claimed in claim 1 or 8.

* * * * *